United States Patent
Stephan

(10) Patent No.: US 10,392,446 B2
(45) Date of Patent: Aug. 27, 2019

(54) COMPOSITIONS AND METHODS TO MODIFY CELLS FOR THERAPEUTIC OBJECTIVES

(71) Applicant: Fred Hutchinson Cancer Research Center, Seattle, WA (US)

(72) Inventor: Matthias Stephan, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 15/672,106

(22) Filed: Aug. 8, 2017

(65) Prior Publication Data

US 2018/0030153 A1    Feb. 1, 2018

Related U.S. Application Data

(63) Continuation of application No. 14/776,661, filed as application No. PCT/US2014/029137 on Mar. 14, 2014.

(60) Provisional application No. 61/785,907, filed on Mar. 14, 2013.

(51) Int. Cl.
| | |
|---|---|
| A61K 48/00 | (2006.01) |
| C12N 15/88 | (2006.01) |
| C07K 16/40 | (2006.01) |
| A61K 9/127 | (2006.01) |
| A61K 38/17 | (2006.01) |
| C07K 16/30 | (2006.01) |
| A61K 39/395 | (2006.01) |
| C07K 14/725 | (2006.01) |
| C07K 14/705 | (2006.01) |
| C07K 16/28 | (2006.01) |
| A61K 47/64 | (2017.01) |
| A61K 47/68 | (2017.01) |
| A61K 47/69 | (2017.01) |
| A61K 9/00 | (2006.01) |
| A61K 9/51 | (2006.01) |

(52) U.S. Cl.
CPC .......... *C07K 16/40* (2013.01); *A61K 9/1271* (2013.01); *A61K 38/177* (2013.01); *A61K 38/1774* (2013.01); *A61K 39/3955* (2013.01); *A61K 47/645* (2017.08); *A61K 47/6455* (2017.08); *A61K 47/6849* (2017.08); *A61K 47/6913* (2017.08); *C07K 14/7051* (2013.01); *C07K 14/70521* (2013.01); *C07K 16/2815* (2013.01); *C07K 16/3069* (2013.01); *C12N 15/88* (2013.01); *A61K 9/0019* (2013.01); *A61K 9/5123* (2013.01); *A61K 48/00* (2013.01); *C07K 2317/622* (2013.01); *C07K 2319/03* (2013.01); *C07K 2319/74* (2013.01); *C12N 2810/859* (2013.01)

(58) Field of Classification Search
None
See application file for complete search history.

(56) References Cited

U.S. PATENT DOCUMENTS

| | | | |
|---|---|---|---|
| 2003/0072794 A1 | 4/2003 | Boulikas | |
| 2003/0166601 A1 | 9/2003 | Woodle et al. | |
| 2004/0043401 A1 | 3/2004 | Sadelain et al. | |
| 2005/0142114 A1 | 6/2005 | Gieseler et al. | |
| 2008/0171061 A1 | 7/2008 | Nixon et al. | |
| 2011/0189209 A1 | 8/2011 | Neville et al. | |
| 2011/0229556 A1* | 9/2011 | Irvine | A61K 39/385 424/450 |
| 2012/0156135 A1 | 6/2012 | Farokhzad et al. | |
| 2016/0145348 A1 | 5/2016 | Stephan | |

FOREIGN PATENT DOCUMENTS

| | | |
|---|---|---|
| WO | WO2012079000 | 6/2012 |
| WO | WO2014153114 | 9/2014 |

OTHER PUBLICATIONS

Orcutt et al., Engineering an antibody with picomolar affinity to DOTA chelates of multiple radionuclides for pretargeted radioimmunotherapy and imaging. Nucl Med Biol. Feb. 2011 ; 38(2): 223-233 (Year: 2011).*
Philip et al., In vivo gene delivery. Efficient transfection of T lymphocytes in adult mice. J Biol Chem. Aug. 5, 1993;268(22):16087-90 (Year: 1993).*
Desai, et al., "Interaction of nanoparticles and cell-penetrating peptides with skin for transdermal drug delivery", Mol. Membr. Biol., vol. 27, No. 7, 2010, 19 pages.
Grandjean, et al., "High-level transgene expression by homologous recombination-mediated gene transfer", Nucleic Acids Research, vol. 39, No. 15 e104, 2011, 15 pages.
Kacherovsky, et al., "Combination of Sleeping Beauty transposition and chemically induced dimerization selection for robust production of engineered cells", Nucleic Acids Research, vol. 40, No. 11e85, 2012, 10 pages.
Office Action dated Feb. 8, 2017 for U.S. Appl. No. 14/776,661.

(Continued)

*Primary Examiner* — Christopher M Babic
*Assistant Examiner* — Arthur S Leonard
(74) *Attorney, Agent, or Firm* — Lee & Hayes PC; C. Rachal Winger

(57) ABSTRACT

The present disclosure provides compositions and methods that rapidly and selectively modify cells of the immune system to achieve therapeutic objectives. The methods can be practiced in vivo and any cell type that expresses a known marker can be targeted for a therapeutic objective.

16 Claims, 9 Drawing Sheets
Specification includes a Sequence Listing.

(56) References Cited

OTHER PUBLICATIONS

Search Report and Written Opinion dated Jul. 28, 2014 in International Application No. PCT/US2014/029137.
Stephan, et al. "Enhancing Cell therapies from the Outside In: Cell Surface Engineering Using Synthetic Nanomaterials", Nano Today, vol. 6, No. 3, 2011, 28 pages.
Debs, et al., "Targeting of anti-Thy 1.1 monoclonal antibody conjugated liposomes in Thy 1.1 mice after intravenous administration," Biochimica et Biophysica Acta, vol. 901, 1987, pp. 183-190.
Dow, et al., "Intravenous Cytokine Gene Delivery by Lipid-DNA Complexes Controls the Growth of Established Lung Metastases," Human Gene Therapy, vol. 10, 1999, pp. 2961-2972.
Ebert, et al., "Lymphocyte apoptosis: induction by gene transfer techniques," Gene Therapy, vol. 4, 1997, pp. 296-302.
Heath, et al., "Antibody-targeted liposomes: Increase in specific toxicity of methotrexate-gamma-aspartate," PNAS, vol. 80, 1983, pp. 1377-1381.
Maruyama, et al., "Lipid composition is important for highly efficient target binding and retention of immunoliposomes," PNAS, vol. 87, 1990, pp. 5744-5748.
Tousignant, et al., "Comprehensive Analysis of the Acute Toxicities Induced by Systemic Administration of Cationic Lipid:Plasmid DNA Complexes in Mice," Human Gene Therapy, vol. 22, 2000, pp. 2493-2513.
Yang and Huang, "Overcoming the inhibitory effect of serum on lipofection by increasing the charge ratio of cationic liposome to DNA," Gene Therapy, vol. 4, 1997, pp. 950-960.
Zhu, et al., "Systemic Gene Expression After Intravenous DNA Delivery into Adult Mice," Science, vol. 261, 1993, 4 pages.

* cited by examiner

P28z minicircle

P28z-S/MAR minicircle

P28z-piggyBac minicircle

COMPOSITIONS AND METHODS TO MODIFY CELLS FOR THERAPEUTIC OBJECTIVES

CROSS REFERENCE TO RELATED APPLICATIONS

This application is a continuation of U.S. patent application Ser. No. 14/776,661, filed on Sep. 14, 2015, which is a U.S. National Phase Application based on International Patent Application No. PCT/US2014/029137, filed on Mar. 14, 2014, which claims priority to U.S. Provisional Patent Application No. 61/785,907, filed Mar. 14, 2013, each of which is incorporated herein by reference in its entirety.

FIELD OF THE DISCLOSURE

The present disclosure provides compositions and methods that rapidly and selectively modify cells of the immune system to achieve therapeutic objectives. The methods can be practiced in vivo and any cell type that expresses or is associated with a known marker can be targeted for a therapeutic objective by the modified cell.

BACKGROUND OF THE DISCLOSURE

One of the primary goals of clinical health research is to develop compositions and methods that rapidly and selectively direct cells of the immune system to achieve therapeutic objectives. For example, vaccines are used to prime the immune system to target antigens associated with unwanted cells. The biological processes underlying conventional vaccines, however, can render them ineffective against many unwanted cells based on, among other factors, the time it takes to prime the immune system, the amount or degree to which the natural immune system can be primed against certain unwanted cell types and over time, the depletion of immune system resources. As examples, conventional vaccine approaches can be ineffective against cancer cells and cells affected by certain infectious diseases.

Using cancer cells as an example of an unwanted cell type, vaccines can be capable of targeting the immune system to destroy cancer cells in some patients. The immune response using this approach, however, requires months to mature and during this time, cancers can significantly progress and become fatal. Thus, conventional vaccines do not provide an adequate method to target and destroy unwanted cancer cells.

To achieve more rapid and potent cancer cell destruction, infusions of autologous T cells genetically targeted to tumor antigen are currently being tested in the clinic and represent a promising treatment option. However, T-cell transfer therapies are also time and labor-intense and must be personalized for each patient in cell production facilities, which are available only at a few highly specialized cancer centers worldwide. Similar issues are encountered with a number of other unwanted cell types. Thus, additional solutions are needed that allow rapid and selective direction of cells of the immune system to achieve therapeutic objectives

SUMMARY OF THE DISCLOSURE

The present disclosure provides compositions and methods that can rapidly and selectively direct cells of the immune system to achieve therapeutic objectives. In particular embodiments, the compositions and methods modify cells of the immune system, such as T cells or natural killer (NK) cells, to target and destroy unwanted cell types. In other embodiments, the compositions and methods modify cells of the immune system, such as monocytes/macrophages, to target and destroy viruses before they infect cells and/or to target bacteria or fungus. In further embodiments, the compositions and methods modify cells of the immune system, such as B cells, to produce and release antibodies, such as broadly-neutralizing antibodies. In additional embodiments, the compositions and methods modify cells of the immune system, such as immunosuppressive regulatory T cells ($T_{REG}$) to target and protect, rather than destroy, cell types. Compositions and methods disclosed herein can also be used to modify stem cells to achieve therapeutic objectives.

The described methods can be practiced in vivo rather than requiring patient-specific isolation and culturing, as is currently required by many cancer treatments. The methods can be practiced in vivo because following administration to a subject, the compositions selectively modify cells of the immune system to achieve selected therapeutic objectives.

The compositions and methods can be used to target any cell type for which a marker is now or later becomes known. The compositions and methods achieve this benefit by modifying cells of the immune system to express targeting agents for the marker of interest.

In particular examples, the cells of the immune system are modified to express targeting agents that bind markers, such as antigens, on unwanted cells. Once bound to an unwanted cell, the immune cells mediate its destruction. Alternatively, the cells of the immune system can be modified to express targeting agents that bind markers expressed by wanted cells or cells in the vicinity of wanted cells. Once bound to a wanted cell or in the vicinity of a wanted cell, the immune cells can mediate protection of the wanted cell.

The compositions and methods disclosed herein also provide further advantages over the current state of the art. For example, the compositions and methods can selectively destroy unwanted cells leaving healthy tissue undamaged. The compositions can be manufactured on a large scale in a stable form with a long shelf life rendering them compatible with wide distribution and inexpensive administration to large patient populations in outpatient settings (i.e., they provide "off-the-shelf" directed treatments). Further, the compositions can be administered in booster doses to reinforce immune cell targeting. Alternatively, the administered composition can be altered over time as a population of unwanted or wanted cell types (collectively "targets" herein) evolves.

The compositions and methods achieve the described benefits by providing nanocarriers. In their simplest form, the nanocarriers include a polynucleotide encoding a targeting agent. The nanocarrier is taken up by a cell of the immune system, which then expresses the encoded targeting agent. The targeting agent selectively binds a marker on a target, directing the cells of the immune system to the site of the therapeutic objective. If the expressed targeting agent is an unwanted cell-targeting agent (such as an antibody or a receptor for a cancer antigen), once bound, the modified immune cell will mediate the destruction of the unwanted cell. If the expressed targeting agent is a wanted cell-targeting agent (such as a receptor for a marker expressed by a cell undergoing autoimmune attack), once bound, the modified immune cell will mediate the protection of the wanted cell.

In some embodiments, nanocarriers further include lymphocyte-directing agents. Lymphocyte-directing agents can achieve selective uptake of the nanocarriers by cells of interest for a particular therapeutic objective. For example, the lymphocyte-directing agents can include binding domains extending from the surface of the nanocarriers that facilitate uptake by lymphocytes or particular classes of lymphocytes. Nanocarriers can also include lymphocyte-directing agents that achieve selective uptake by more than one cell type.

Nanocarriers can also further include one or more of: an endosomal release agent to facilitate release of the polynucleotide from endosomal compartments of the lymphocytes and/or a nuclear localization signal (NLS) to direct the polynucleotide into the nucleus of the lymphocyte for expression, particularly when, for example, the polynucleotide comprises plasmid DNA.

In particular embodiments, the nanocarriers comprise a porous nanoparticle surrounded by a coating. In these embodiments, the polynucleotide (and optionally the NLS) can be within the pores of the nanoparticle and the optional lymphocyte-directing agent and endosomal release agent can extend from the surface of the coating.

BRIEF DESCRIPTION OF THE FIGURES

(FIG. 2A) Schematic representation of the protocell nanoparticle used in studies described herein. (FIG. 2B) A representative TEM image of a protocell nanoparticle.

(FIG. 4A) Prostate-Specific Membrane Antigen (PSMA)-specific chimeric antigen receptor P28z (FIG. 4B) Flow cytometric measurement of surface P28z expression on mouse effector T cells 30 hours after incubation with "empty" (left panel) or P28z minicircle-loaded (right panel) protocell nanoparticles. (FIG. 4C) 95 $^1$Cr release assay of T cells 30 h after nanoparticle transfection targeting PSMA-positive TRAMP prostate tumor cells. (FIG. 4D) Light microscope images of nanoparticle-transfected T cells co-cultured on a TRAMP prostate tumor cell monolayer. (FIG. 4E) Flow cytometric measurement of protocell binding to circulating host T cells 6 hours after intravenous injection of $1 \times 10^{11}$ fluorescently tagged nanoparticles.

(FIG. 5A) Sequential bioluminescence imaging of Firefly luciferase-expressing TRAMP-PSMA tumors. (FIG. 5B) Quantified bioluminescent tumor signal. Pairwise differences in bioluminescent photon counts between treatment groups were statistically analyzed with the Wilcoxon rank-sum test. *, **=Significant $P<0.0001$.

(FIG. 6A) Structure of the P28z minicircle. The prostate-specific membrane antigen (PSMA)-targeting chimeric antigen receptor P28z is expressed under the control of the T-cell specific CD3-delta promoter. (FIG. 6B) A scaffold/matrix attachment region (S/MAR) is shown upstream of the poly-A signal to allow sustained episomal replication. (FIG. 6C) Alternatively, the gene expression cassette can be flanked by the piggyBac inverted terminal repeats. The piggyBac transposon is a mobile genetic element that efficiently transposes between vector and chromosome via a "cut and paste" mechanism. This integration event is mediated by piggyBac transposase. Therefore, in piggyBac transposon studies, a plasmid encoding the hyperactive form of piggyBac transposase iPB7 will be co-encapsulated into protocell nanoparticles.

DETAILED DESCRIPTION

Figure 1:
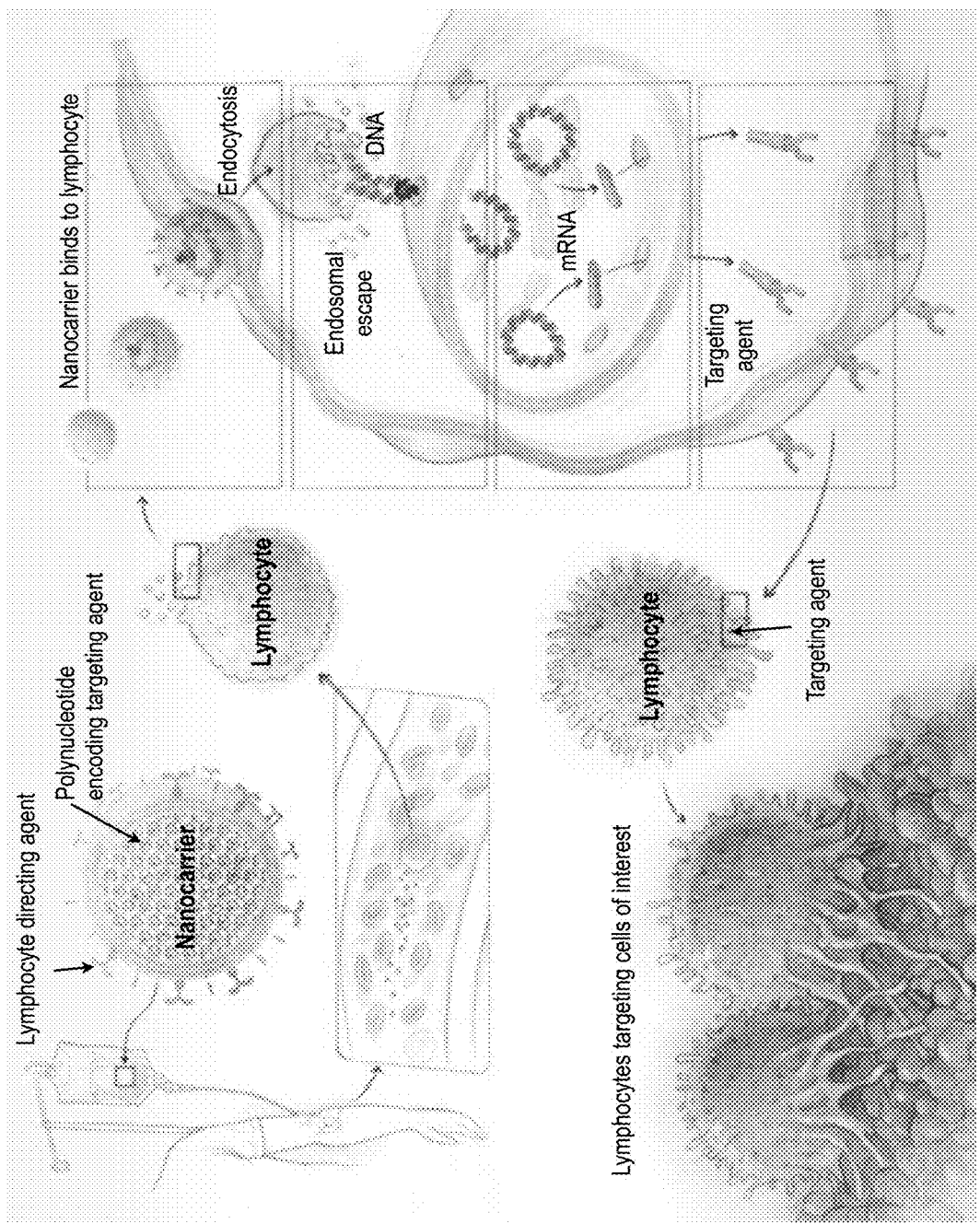
FIG. 1: Schematic of described strategy to rapidly and selectively modify immune cells for therapeutic objectives using synthetic nanocarriers. Nanocarriers are loaded with polynucleotides that encode a targeting agent (e.g. tumor- or virus-specific T-cell receptor). Surface-anchored lymphocyte directing agents (e.g. anti-CD3 antibody) enable these nanocarriers to bind lymphocytes selectively. Upon infusion into a patient's bloodstream, the nanocarriers transfer the polynucleotide molecules into lymphocytes, which subsequently express the targeting agent on their surface. Lymphocytes then recognize and lyse cells of interest (e.g. cancerous or virus-infected cells).

The present disclosure provides compositions and methods that can rapidly and selectively direct cells within the body to achieve therapeutic objectives. In particular embodiments, the compositions and methods modify cells of the immune system, such as T-cells or NK cells, to target and destroy unwanted cell types. In other embodiments, the compositions and methods modify cells of the immune system, such as monocytes/macrophages to target and destroy viruses before they infect cells and/or bacterial or fungal cells. In further embodiments, the compositions and methods modify cells of the immune system, such as B cells, to produce and release antibodies, such as broadly-neutralizing antibodies. In additional embodiments, the compositions and methods modify cells of the immune system, such as immunosuppressive $T_{REG}$ cells to target and protect cell types from, for example, autoimmune attack. Compositions and methods disclosed herein can also be used to modify stem cells to achieve therapeutic objectives.

The described methods can be practiced in vivo rather than requiring patient-specific isolation and culturing, as is currently required by many treatments. The methods can be practiced in vivo because following administration to a subject, the compositions selectively modify cells of interest to achieve the therapeutic objective.

As an example, one of the primary goals of clinical health research is to develop compositions and methods to rapidly and selectively direct the immune system to destroy unwanted cells. For example, vaccines are used to prime the immune system to target antigens associated with unwanted cells. The biological processes underlying conventional vaccines, however, can render them ineffective against many unwanted cells based on, among other factors, the time it takes to prime the immune system, the amount or degree to which the natural immune system can be primed against certain unwanted cell types and over time, the depletion of immune system resources.

The present disclosure provides compositions and methods that can rapidly modify cells of the immune system to target and destroy unwanted cell types. The methods can be practiced in vivo rather than requiring patient-specific isolation and culturing, as is currently required by many cancer treatments. The methods can be practiced in vivo because following administration to a subject, the compositions selectively modify cells of the immune system to target unwanted cell types.

The compositions and methods can be used to target any cell type for which a marker is now or later becomes known. The compositions and methods achieve this benefit by modifying cells of the immune system to express targeting agents for the marker expressed by the target or in the vicinity of a target. In particular examples, the cells of the immune system are modified to express targeting agents that bind markers, such as antigens, on unwanted cells. Once bound to an unwanted cell, the immune cells mediate its destruction. Alternatively, cells of the immune system can be modified to express targeting agents that bind markers on or in the vicinity of wanted cells. Once bound to a wanted cell or in the wanted cell's vicinity, the immune cell can mediate its protection.

The compositions and methods achieve the described benefits by providing nanocarriers that include a polynucleotide encoding a targeting agent. Cells that uptake the nanocarrier will begin to express the polynucleotide, thereby expressing the targeting agent. The targeting agent directs the modified immune cell to the site of the therapeutic objective. In one example, a lymphocyte uptakes the nanocarrier and begins to express an unwanted cell targeting agent. In this embodiment, the lymphocyte then binds and mediates the destruction of the unwanted cell type.

Additional embodiments of the nanocarriers include lymphocyte-directing agents that selectively deliver the nanocarriers to cells of interest. The compositions can further include one or more of: an endosomal release agent to facilitate release of the polynucleotide from endosomal compartments of cells of the immune system and/or a nuclear localization signal (NLS) to direct the polynucleotide into the nucleus of the cell for expression if, for example, the polynucleotide includes plasmid DNA.

In particular embodiments, the nanocarriers comprise a porous nanoparticle surrounded by a coating. In these embodiments, the polynucleotide (and optionally the NLS) can be within the pores of the nanoparticle and the lymphocyte-directing agent (and optionally the endosomal release agent) can extend from the surface of the coating. Each of these components is now described in further detail.

Lymphocyte-Directing Agents. The lymphocyte-directing agents of the disclosed compositions selectively bind immune cells of interest. In particular embodiments, the cells are lymphocytes. In these embodiments, lymphocyte-directing agents can direct the compositions to any lymphocyte capable of, without limitation, (i) targeting and killing unwanted cells, (ii) targeting unwanted cells for killing by other cell types, (iii) mediating unwanted cell killing; (iv) targeting viruses for destruction before viral entry into cells, (v) antibody production and/or (vi) targeting and protecting beneficial cells. As described herein, lymphocytes include T-cells, B cells, natural killer (NK) cells, monocytes/macrophages and hematopoietic stem cells.

Several different subsets of T-cells have been discovered, each with a distinct function. In particular embodiments, lymphocyte-directing agents achieve selective direction to particular lymphocyte populations through receptor-mediated endocytosis. For example, a majority of T-cells have a T-cell receptor (TCR) existing as a complex of several proteins. The actual T-cell receptor is composed of two separate peptide chains, which are produced from the independent T-cell receptor alpha and beta (TCRα and TCRβ) genes and are called α- and β-TCR chains. Lymphocyte directing agents disclosed herein can bind α- and/or β-TCR chains to achieve selective delivery of a polynucleotide to these T cells.

γδ T-cells represent a small subset of T-cells that possess a distinct T-cell receptor (TCR) on their surface. In γδ T-cells, the TCR is made up of one γ-chain and one δ-chain. This group of T-cells is much less common (2% of total T-cells) than the αβ T-cells. Nonetheless, lymphocyte-directing agents disclosed herein can bind γ- and/or δ TCR chains to achieve selective delivery of a polynucleotide to these T cells.

CD3 is expressed on all mature T cells. Accordingly, lymphocyte-directing agents disclosed herein can bind CD3 to achieve selective delivery of a polynucleotide to all mature T-cells. Activated T-cells express 4-1BB (CD137). Accordingly, lymphocyte-directing agents disclosed herein can bind 4-1BB to achieve selective delivery of a polynucleotide to activated T-cells. CD5 and transferrin receptor are also expressed on T-cells and can be used to achieve selective delivery of a polynucleotide to T-cells.

T-cells can further be classified into helper cells (CD4+ T-cells) and cytotoxic T-cells (CTLs, CD8+ T-cells), which comprise cytolytic T-cells. T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response. Lymphocyte-directing agents disclosed herein can bind CD4 to achieve selective delivery of a polynucleotide to T helper cells.

Cytotoxic T-cells destroy virally infected cells and tumor cells, and are also implicated in transplant rejection. These cells are also known as CD8+ T-cells because they express the CD8 glycoprotein at their surface. These cells recognize their targets by binding to antigen associated with MHC class I, which is present on the surface of nearly every cell of the body. Lymphocyte-directing agents disclosed herein can bind CD8 to achieve selective delivery of a polynucleotide to CTL.

"Central memory" T-cells (or "$T_{CM}$") as used herein refers to an antigen experienced CTL that expresses CD62L or CCR7 and CD45RO on the surface thereof, and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells. Lymphocyte-directing agents disclosed herein can bind CD62L, CCR7, CD25, CD127, CD45RO and/or CD95 to achieve selective delivery of a polynucleotide to $T_{CM}$.

"Effector memory" T-cell (or "$T_{EM}$") as used herein refers to an antigen experienced T-cell that does not express or has decreased expression of CD62L on the surface thereof as compared to central memory cells, and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T-cells are positive for granzyme B and perforin as compared to memory or naive T-cells. Lymphocyte-directing agents disclosed herein can bind granzyme B and/or perforin to achieve selective delivery of a polynucleotide to $T_{EM}$.

Regulatory T cells ("$T_{REG}$") are a subpopulation of T cells, which modulate the immune system, maintain tolerance to self-antigens, and abrogate autoimmune disease. $T_{REG}$ express CD25, CTLA-4, GITR, GARP and LAP. Lymphocyte-directing agents disclosed herein can bind CD25, CTLA-4, GITR, GARP and/or LAP to achieve selective delivery of a polynucleotide to naïve $T_{REG}$.

"Naive" T-cells as used herein refers to a non-antigen experienced T cell that expresses CD62L and CD45RA, and does not express CD45RO as compared to central or effector memory cells. In some embodiments, naive CD8+ T lymphocytes are characterized by the expression of phenotypic markers of naive T-cells including CD62L, CCR7, CD28, CD127, and CD45RA. Lymphocyte-directing agents disclosed herein can bind CD62L, CCR7, CD28, CD127 and/or CD45RA to achieve selective delivery of a polynucleotide to naïve T-cells.

Natural killer cells (also known as NK cells, K cells, and killer cells) are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3. Lymphocyte-directing agents disclosed herein can bind CD8, CD16 and/or CD56 to achieve selective delivery of a polynucleotide to NK cells.

Macrophages (and their precursors, monocytes) reside in every tissue of the body (in certain instances as microglia, Kupffer cells and osteoclasts) where they engulf apoptotic cells, pathogens and other non-self components. Because monocytes/macrophages engulf non-self components, a particular macrophage- or monocyte-directing agent is not required on the nanocarriers described herein for selective uptake by these cells. Alternatively, lymphocyte-directing agents disclosed herein can bind CD11b, F4/80; CD68; CD11c; IL-4Rα; and/or CD163 to achieve selective delivery of a polynucleotide to monocytes/macrophages.

B cells can be distinguished from other lymphocytes by the presence of the B cell receptor (BCR). The principal function of B cells is to make antibodies. B cells express CD5, CD19, CD20, CD21, CD22, CD35, CD40, CD52, and CD80. Lymphocyte-directing agents disclosed herein can bind CD5, CD19, CD20, CD21, CD22, CD35, CD40, CD52, and/or CD80 to achieve selective delivery of a polynucleotide to B-cells.

Lymphocyte function-associated antigen 1 (LFA-1) is expressed by all T-cells, B-cells and monocytes/macrophages. Accordingly, lymphocyte-directing agents disclosed herein can bind LFA-1 to achieve selective delivery of a polynucleotide to T-cells, B-cells and monocytes/macrophages.

Hematopoietic stem cells can also be targeted for selective delivery of nanocarriers disclosed herein. Hematopoietic stem cells express CD34, CD133, Sca-1 and CD117. Lymphocyte-directing agents disclosed herein can bind CD34, CD133, Sca-1 and/or CD117 to achieve selective delivery of a polynucleotide to hematopoietic stem cells.

"Selective delivery" means that polynucleotides are delivered and expressed by one or more selected lymphocyte populations. In particular embodiments, selective delivery is exclusive to a selected lymphocyte population. In further embodiments, at least 65%, 70%, 75%, 80%, 85%, 90%, 95% or 99% of administered polynucleotides are delivered and/or expressed by a selected lymphocyte population. In further embodiments, selective delivery ensures that non-lymphocyte cells do not express delivered polynucleotides. For example, when the targeting agent is a T-cell receptor (TCR) gene, selectivity is ensured because only T cells have the zeta chains required for TCR expression. Selective delivery can also be based on lack of polynucleotide uptake into unselected cells or based on the presence of a specific promoter within the polynucleotide sequence when the polynucleotide includes plasmid DNA. For example, plasmid DNA can include a T-cell-specific CD3-delta promoter. Additional promoters that can achieve selective delivery include: the murine stem cell virus promoter or the distal lck promoter for T cells or hematopoietic stem cells; the CD45 promoter, WASP promoter or IFN-beta promoter for hematopoietic stem cells; the B29 promoter for B cells; or the CD14 promoter or the CD11b promoter for monocytes/macrophages.

As indicated, lymphocyte-directing agents can include binding domains for motifs found on lymphocyte cells. Lymphocyte-directing agents can also include any selective binding mechanism allowing selective uptake into lymphocytes. In particular embodiments, lymphocyte-directing agents include binding domains for T-cell receptor motifs; T-cell α chains; T-cell β chains; T-cell γ chains; T-cell δ chains; CCR7; CD3; CD4; CD5; CD7; CD8; CD11b; CD11c; CD16; CD19; CD20; CD21; CD22; CD25; CD28; CD34; CD35; CD40; CD45RA; CD45RO; CD52; CD56; CD62L; CD68;CD80; CD95; CD117; CD127; CD133; CD137 (4-1BB); CD163; F4/80; IL-4Rα; Sca-1; CTLA-4; GITR; GARP; LAP; granzyme B; LFA-1; transferrin receptor; and combinations thereof.

In particular embodiments, binding domains include cell marker ligands, receptor ligands, antibodies, peptides, peptide aptamers, nucleic acids, nucleic acid aptamers, spiegelmers or combinations thereof. Within the context of lymphocyte-directing agents, binding domains include any substance that binds to another substance to form a complex capable of mediating endocytosis.

"Antibodies" are one example of binding domains and include whole antibodies or binding fragments of an antibody, e.g., Fv, Fab, Fab', F(ab')$_2$, Fc, and single chain Fv fragments (scFvs) or any biologically effective fragments of an immunoglobulin that bind specifically to a motif expressed by a lymphocyte. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects.

Antibodies that specifically bind a motif expressed by a lymphocyte can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to a lymphocyte motif. For example, binding domains may be identified by screening a Fab phage library for Fab fragments that specifically bind to a target of interest (see Hoet et al., *Nat. Biotechnol.* 23:344, 2005). Phage display libraries of human antibodies are also available. Additionally, traditional strategies for hybridoma development using a target of interest as an immunogen in convenient systems (e.g., mice, HuMAb mouse®, TC mouse™, KM-mouse®, llamas, chicken, rats, hamsters, rabbits, etc.) can be used to develop binding domains. In particular embodiments, antibodies specifically bind to motifs expressed by a selected lymphocyte and do not cross react with nonspecific components or unrelated targets. Once identified, the amino acid sequence or polynucleotide sequence coding for the antibody can be isolated and/or determined.

In particular embodiments, binding domains of lymphocyte-directing agents include T-cell receptor motif antibodies; T-cell α chain antibodies; T-cell β chain antibodies; T-cell γ chain antibodies; T-cell δ chain antibodies; CCR7 antibodies; CD3 antibodies; CD4 antibodies; CD5 antibodies; CD7 antibodies; CD8 antibodies; CD11b antibodies; CD11c antibodies; CD16 antibodies; CD19 antibodies; CD20 antibodies; CD21 antibodies; CD22 antibodies; CD25 antibodies; CD28 antibodies; CD34 antibodies; CD35 antibodies; CD40 antibodies; CD45RA antibodies; CD45RO antibodies; CD52 antibodies; CD56 antibodies; CD62L antibodies; CD68 antibodies; CD80 antibodies; CD95 antibodies; CD117 antibodies; CD127 antibodies; CD133 antibodies; CD137 (4-1BB) antibodies; CD163 antibodies; F4/80 antibodies; IL-4Rα antibodies; Sca-1 antibodies; CTLA-4 antibodies; GITR antibodies GARP antibodies; LAP antibodies; granzyme B antibodies; LFA-1 antibodies; or transferrin receptor antibodies. These binding domains also can consist of scFv fragments of the foregoing antibodies. In one particular embodiment, the lymphocyte-directing agent binding domain includes the scFv fragment (SEQ ID NO. 1) of the PSMA-specific chimeric antigen receptor (CAR), P28z.

Peptide aptamers include a peptide loop (which is specific for a target protein) attached at both ends to a protein scaffold. This double structural constraint greatly increases the binding affinity of the peptide aptamer to levels comparable to an antibody. The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Spl). Peptide aptamer selection can be made using different systems, such as the yeast two-hybrid system (e.g., Gal4 yeast-two-hybrid system) or the LexA interaction trap system.

Nucleic acid aptamers are single-stranded nucleic acid (DNA or RNA) ligands that function by folding into a specific globular structure that dictates binding to target proteins or other molecules with high affinity and specificity, as described by Osborne et al., Curr. Opin. Chem. Biol. 1:5-9, 1997; and Cerchia et al., FEBS Letters 528:12-16, 2002. In particular embodiments, aptamers are small (~15 KD; or between 15-80 nucleotides or between 20-50 nucleotides). Aptamers are generally isolated from libraries consisting of $10^{14}$-$10^{15}$ random oligonucleotide sequences by a procedure termed SELEX (systematic evolution of ligands by exponential enrichment; see, for example, Tuerk et al., Science, 249:505-510, 1990; Green et al., Methods Enzymology. 75-86, 1991; and Gold et al., Annu. Rev. Biochem., 64: 763-797, 1995). Further methods of generating aptamers are described in, for example, U.S. Pat. Nos. 6,344,318; 6,331,398; 6,110,900; 5,817,785; 5,756,291; 5,696,249; 5,670,637; 5,637,461; 5,595,877; 5,527,894; 5,496,938; 5,475,096; and 5,270,16. Spiegelmers are similar to nucleic acid aptamers except that at least one β-ribose unit is replaced by β-D-deoxyribose or a modified sugar unit selected from, for example, β-D-ribose, α-D-ribose, β-L-ribose.

Other agents that can facilitate internalization by and/or transfection of lymphocytes, such as poly(ethyleneimine)/DNA (PEI/DNA) complexes can also be used.

Polynucleotides Encoding Targeting Agents. As used herein, the term "polynucleotide" includes a nucleic acid molecule that contains a nucleic acid sequence such that upon introduction into a targeted lymphocyte, the nucleic acid molecule can cause transcription and resulting translation of targeting agents encoded by the nucleic acid sequence of the nucleic acid molecule. In particular embodiments, the targeting agent is an unwanted cell targeting agent. In further embodiments, the targeting agent is a wanted cell targeting agent.

As used herein, the term "gene" refers to a nucleic acid sequence that encodes a targeting agent. This definition includes various sequence polymorphisms, mutations, and/or sequence variants wherein such alterations do not affect the function of the encoded targeting agent. The term "gene" may include not only coding sequences but also regulatory regions such as promoters, enhancers, and termination regions. The term further can include all introns and other DNA sequences spliced from the mRNA transcript, along with variants resulting from alternative splice sites. Nucleic acid sequences encoding the targeting agent can be DNA or RNA that directs the expression of the targeting agent. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific lymphocyte. Gene sequences to encode targeting agents disclosed herein are available in publicly available databases and publications, incorporated by reference herein.

As used herein, the term "encoding" refers to a property of sequences of nucleotides in a polynucleotide, such as a plasmid, a gene, cDNA, mRNA, to serve as templates for synthesis of targeting agents. A polynucleotide can, e.g., encode a protein if transcription and translation of mRNA produced by that gene produces the protein in a cell or other biological system. Unless otherwise specified, polynucleotides having a sequence encoding a targeting agent include all nucleotide sequences that are degenerate versions of each other and that encode the same amino acid sequence. The polynucleotides that encode proteins and RNA can also include introns.

In some embodiments, the polynucleotide includes a plasmid, a cDNA, or an mRNA that can include, e.g., a sequence (e.g., a gene) for expressing a targeting agent. Suitable plasmids include standard plasmid vectors and minicircle plasmids that can be used to transfer a gene to a lymphocyte. The polynucleotides (e.g., minicircle plasmids) can further include any additional sequence information to facilitate transfer of the genetic material (e.g., a sequence encoding a receptor to an antigen) to lymphocytes. For example, the polynucleotides can include promoters, such as general promoters, tissue-specific promoters, cell-specific promoters, and/or promoters specific for the nucleus or cytoplasm. Promoters and plasmids (e.g., minicircle plasmids) are generally well known in the art and can be prepared using conventional techniques. As described further herein, the polynucleotides can be used to transfect lymphocytes. Unless otherwise specified, the terms transfect, transfected, or transfecting can be used to indicate the presence of exogenous polynucleotides or the expressed polypeptide therefrom in a lymphocyte. A number of vectors are known to be capable of mediating transfer of genes to lymphocytes, as is known in the art.

In particular embodiments, the transfected polynucleotides can edit the antigen-specificity of lymphocytes without affecting off-target bystander cells (i.e., provide for selective delivery as defined herein). For example, delivered genes can be expressed under the control of a lymphocyte-specific promoter. In particular embodiments, the promoters can be included in minicircle plasmids that are a form of supercoiled DNA molecule for nonviral gene transfer, which have neither bacterial origin of replication nor antibiotic resistance marker. They are thus smaller and potentially safer than the standard plasmids currently used in gene therapy.

To sustain the expression of transferred targeting agent genes, for example, in rapidly dividing lymphocytes, a scaffold/matrix attachment region can also be inserted into the polynucleotides. Polynucleotides containing an expression cassette linked to a S/MAR element, can autonomously replicate extra-chromosomally in dividing cells. In some embodiments, PiggyBac or Sleeping Beauty transposase-containing plasmids can also be used to stably integrate nanocarrier-delivered targeting agent genes into the genome of transfected lymphocytes. Other options to sustain expression include homo sapiens transposon-derived Buster1 transposase-like protein gene; human endogenous retrovirus H protease/integrase-derived ORF1; homo sapiens Cas-Br-M (murine) ecotropic retroviral transforming sequence; homo sapiens endogenous retroviral sequence K; homo sapiens endogenous retroviral family W; homo sapiens LINE-1 type transposase domain; or homo sapiens pogo transposable element.

When a delivered polynucleotide is mRNA, backbone modifications can increase the mRNA's stability making resistant to premature cleavage.

Targeted Cells & Associated Markers. Targeted cells can be unwanted cells or wanted cells. Unwanted cells include any cell type that is (i) capable of recognition and destruction by the immune system; and (ii) deemed undesirable by a subject, physician, veterinarian or researcher. Unwanted cells include (i) eukaryotic cells that are either cancerous or infected with a pathogen such as a virus and (ii) prokaryotic cells, such as certain bacteria, fungi or yeast. Wanted cells include any cell type that is (i) capable of recognition and protection by the immune system; and (ii) deemed desirable by a subject, physician, veterinarian or researcher. Wanted cells can include cells undergoing auto-immune attack or bacteria that are beneficial to the health of a microbiome.

For targeting according to the compositions and methods disclosed herein, unwanted or wanted cells must be associated with a marker that is currently known or later discovered. In particular embodiments, the markers are antigens. Antigens refer to substances capable of either binding to an antigen binding region of an immunoglobulin molecule or of eliciting an immune response, e.g., a T cell-mediated immune response by the presentation of the antigen on Major Histocompatibility Antigen (MHC) cellular proteins. "Antigens" include antigenic determinants, haptens, and immunogens, which may be peptides, small molecules, carbohydrates, lipids, nucleic acids or combinations thereof. When referencing antigens that are processed for presentation to T cells, the term "antigen" refers to those portions of the antigen (e.g., a peptide fragment) that is a T cell epitope presented by MHC to the T cell receptor. When used in the context of a B cell mediated immune response in the form of an antibody that is specific for an "antigen", the portion of the antigen that binds to the complementarity determining regions of the variable domains of the antibody (light and heavy) is referenced. The bound portion may be a linear or three-dimensional epitope.

Cancer Markers. In particular embodiments, markers are expressed by unwanted cells from cancers. Exemplary cancers include adrenal cancers, bladder cancers, blood cancers, bone cancers, brain cancers, breast cancers, carcinoma, cervical cancers, colon cancers, colorectal cancers, corpus uterine cancers, ear, nose and throat (ENT) cancers, endometrial cancers, esophageal cancers, gastrointestinal cancers, head and neck cancers, Hodgkin's disease, intestinal cancers, kidney cancers, larynx cancers, leukemias, liver cancers, lymph node cancers, lymphomas, lung cancers, melanomas, mesothelioma, myelomas, nasopharynx cancers, neuroblastomas, non-Hodgkin's lymphoma, oral cancers, ovarian cancers, pancreatic cancers, penile cancers, pharynx cancers, prostate cancers, rectal cancers, sarcoma, seminomas, skin cancers, stomach cancers, teratomas, testicular cancers, thyroid cancers, uterine cancers, vaginal cancers, vascular tumors, and metastases thereof.

Particular antigen markers associated with cancers cells include A33; BAGE; Bcl-2; β-catenin; CA125; CA19-9; CD5; CD19; CD20; CD21; CD22; CD33; CD37; CD45; CD123; CEA; c-Met; CS-1; cyclin B1; DAGE; EBNA; EGFR; ephrinB2; estrogen receptor; FAP; ferritin; folate-binding protein; GAGE; G250; GD-2; GM2; gp75, gp100 (Pmel 17); HER-2/neu; HPV E6; HPV E7; Ki-67; LRP; mesothelin, p53, PRAME; progesterone receptor; PSA; PSMA; MAGE; MART; mesothelin; MUC; MUM-1-B; myc; NYESO-1; ras; RORI; survivin; tenascin; TSTA tyrosinase; VEGF; and WT1.

Without limiting the foregoing, the particular following cancers can be treated by targeting the associated provided antigens: leukemia/lymphoma (CD19, CD20, CD22, ROR1, CD33); multiple myeloma (B-cell maturation antigen (BCMA)); prostate cancer (PSMA, WT1, Prostate Stem Cell antigen (PSCA), SV40 T); breast cancer (HER2, ERBB2); stem cell cancer (CD133); ovarian cancer (L1-CAM, extracellular domain of MUC16 (MUC-CD), folate binding protein (folate receptor), Lewis Y); renal cell carcinoma (carboxy-anhydrase-IX (CAIX); melanoma (GD2); and pancreatic cancer (mesothelin, CEA, CD24).

In further particular examples, cancer cell antigens include:

| Cancer Antigen | Sequence | SEQ ID NO. |
|---|---|---|
| PSMA | MWNLLHETDSAVATARRPRWLCAGALVLAGGFFLLGF LFGWFIKSSNEATNITPKHNMKAFLDELKAENIKKFLYN FTQIPHLAGTEQNFQLAKQIQSQWKEFGLDSVELAHY DVLLSYPNKTHPNYISIINEDGNEIFNTSLFEPPPPGYE NVSDIVPPFSAFSPQGMPEGDLVYVNYARTEDFFKLE | 2 |

| Cancer Antigen | Sequence | SEQ ID NO. |
|---|---|---|
| | RDMKINCSGKIVIARYGKVFRGNKVKNAQLAGAKGVIL YSDPADYFAPGVKSYPDGWNLPGGGVQRGNILNLNG AGDPLTPGYPANEYAYRRGIAEAVGLPSIPVHPIGYYD AQKLLEKMGGSAPPDSSWRGSLKVPYNVGPGFTGNF STQKVKMHIHSTNEVTRIYNVIGTLRGAVEPDRYVILGG HRDSWVFGGIDPQSGAAVVHEIVRSFGTLKKEGWRP RRTILFASWDAEEFGLLGSTEWAEENSRLLQERGVAYI NADSSIEGNYTLRVDCTPLMYSLVHNLTKELKSPDEGF EGKSLYESWTKKSPSPEFSGMPRISKLGSGNDFEVFF QRLGIASGRARYTKNWETNKFSGYPLYHSVYETYELV EKFYDPMFKYHLTVAQVRGGMVFELANSIVLPFDCRD YAVVLRKYADKIYSISMKHPQEMKTYSVSFDSLFSAVK NFTEIASKFSERLQDFDKSNPIVLRMMNDQLMFLERAF IDPLGLPDRPFYRHVIYAPSSHNKYAGESFPGIYDALFD IESKVDPSKAWGEVKRQIYVAAFTVQAAAETLSEVA | |
| PSCA | MKAVLLALLMAGLALQPGTALLCYSCKAQVSNEDCLQ VENCTQLGEQCWTARIRAVGLLTVISKGCSLNCVDDS QDYYVGKKNITCCDTDLCNASGAHALQPAAAILALLPA LGLLLWGPGQL | 3 |
| Mesothelin | MALPTARPLLGSCGTPALGSLLFLLFSLGWVQPSRTLA GETGQEAAPLDGVLANPPNISSLSPRQLLGFPCAEVS GLSTERVRELAVALAQKNVKLSTEQLRCLAHRLSEPPE DLDALPLDLLLFLNPDAFSGPQACTHFFSRITKANVDLL PRGAPERQRLLPAALACWGVRGSLLSEADVRALGGLA CDLPGRFVAESAEVLLPRLVSCPGPLDQDQQEAARAA LQGGGPPYGPPSTWSVSTMDALRGLLPVLGQPIIRSIP QGIVAAWRQRSSRDPSWRQPERTILRPRFRREVEKTA CPSGKKAREIDESLIFYKKWELEACVDAALLATQMDRV NAIPFTYEQLDVLKHKLDELYPQGYPESVIQHLGYLFLK MSPEDIRKWNVTSLETLKALLEVNKGHEMSPQVATLID RFVKGRGQLDKDTLDTLTAFYPGYLCSLSPEELSSVPP SSIWAVRPQDLDTCDPRQLDVLYPKARLAFQNMNGSE YFVKIQSFLGGAPTEDLKALSQQNVSMDLATFMKLRTD AVLPLTVAEVQKLLGPHVEGLKAEERHRPVRDWILRQ RQDDLDTLGLGLQGGIPNGYLVLDLSVQEALSGTPCLL GPGPVLTVLALLLASTLA | 4 |
| CD19 | MPPPRLLFFLLFLTPMEVRPEEPLVVKVEEGDNAVLQC LKGTSDGPTQQLTWSRESPLKPFLKLSLGLPGLGIHM RPLASWLFIFNVSQQMGGFYLCQPGPPSEKAWQPGW TVNVEGSGELFRWNVSDLGGLGCGLKNRSSEGPSSP SGKLMSPKLYVWAKDRPEIWEGEPPCVPPRDSLNQSL SQDLTMAPGSTLWLSCGVPPDSVSRGPLSVVTHVHPK GPKSLLSLELKDDRPARDMWVMETGLLLPRATAQDAG KYYCHRGNLTMSFHLEITARPVLWHWLLRTGGWKVS AVTLAYLIFCLCSLVGILHLQRALVLRRKRKRMTDPTRR FFKVTPPPGSGPQNQYGNVLSLPTPTSGLGRAQRWA AGLGGTAPSYGNPSSDVQADGALGSRSPPGVGPEEE EGEGYEEPDSEEDSEFYENDSNLGQDQLSQDGSGYE NPEDEPLGPEDEDSFSNAESYENEDEELTQPVARTMD FLSPHGSAWDPSREATSLGSQSYEDMRGILYAAPQLR SIRGQPGPNHEEDADSYENMDNPDGPDPAWGGGGR MGTWSTR | 5 |
| CD20 | MTTPRNSVNGTFPAEPMKGPIAMQSGPKPLFRRMSSL VGPTQSFFMRESKTLGAVQIMNGLFHIALGGLLMIPAGI YAPICVTVWYPLWGGIMYIISGSLLAATEKNSRKCLVK GKMIMNSLSLFAAISGMILSIMDILNIKISHFLKMESLNFI RAHTPYINIYNCEPANPSEKNSPSTQYCYSIQSLFLGIL SVMLIFAFFQELVIAGIVENEWKRTCSRPKSNIVLLSAE EKKEQTIEIKEEVVGLTETSSQPKNEEDIEIIPIQEEEEE ETETNFPEPPQDQESSPIENDSSP | 6 |
| ROR1 | MHRPRRRGTRPPLLALLAALLLAARGAAAQETELSVSA ELVPTSSWNISSELNKDSYLTLDEPMNNITTSLGQTAE LHCKVSGNPPPTIRWFKNDAPVVQEPRRLSFRSTIYGS RLRIRNLDTTDTGYFQCVATNGKEVVSSTGVLFVKFGP PPTASPGYSDEYEEDGFCQPYRGIACARFIGNRTVYM ESLHMQGEIENQITAAFTMIGTSSHLSDKCSQFAIPSLC HYAFPYCDETSSVPKPRDLCRDECEILENVLCQTEYIF ARSNPMILMRLKLPNCEDLPQPESPEAANCIRIGIPMA DPINKNHKCYNSTGVDYRGTVSVTKSGRQCQPWNSQ YPHTHTFTALRFPELNGGHSYCRNPGNQKEAPWCFTL DENFKSDLCDIPACDSKDSKEKNKMEILYILVPSVAIPL | 7 |

-continued

| Cancer Antigen | Sequence | SEQ ID NO. |
|---|---|---|
| | AIALLFFFICVCRNNQKSSSAPVQRQPKHVRGQNVEM SMLNAYKPKSKAKELPLSAVRFMEELGECAFGKIYKG HLYLPGMDHAQLVAIKTLKDYNNPQQVVTEFQQEASLM AELHHPNIVCLLGAVTQEQPVCMLFEYINQGDLHEFLI MRSPHSDVGCSSDEDGTVKSSLDHGDFLHIAIQIAAG MEYLSSHFFVHKDLAARNILIGEQLHVKISDLGLSREIY SADYYRVQSKSLLPIRWMPPEAIMYGKFSSDSDIWSF GVVLWEIFSFGLQPYYGFSNQEVIEMVRKRQLLPCSE DCPPRMYSLMTECWNEIPSRRPRFKDIHVRLRSWEGL SSHTSSTTPSGGNATTQTTSLSASPVSNLSNPRYPNY MFPSQGITPQGQIAGFIGPPIPQNQRFIPINGYPIPPGY AAFPAAHYQPTGPPRVIQHCPPPKSRSPSSASGSTST GHVTSLPSSGSNQEANIPLLPHMSIPNHPGGMGITVFG NKSQKPY KIDSKQASLLGDANIHGHTESMISAEL | |
| WT1 | MGHHHHHHHHHHSSGHIEGRHMRRVPGVAPTLVRSA SETSEKRPFMCAYPGCNKRYFKLSHLQMHSRKHTGE KPYQCDFKDCERRFFRSDQLKRHQRRHTGVKPFQCK TCQRKFSRSDHLKTHTRTHTGEKPFSCRWPSCQKKF ARSDELVRHHNMHQRNMTKLQLAL | 8 |

In particular embodiments disclosed herein, modified T cells, NK cells and/or monocytes/macrophages target and destroy cancer cells. B cells can also be modified to secrete tumor-specific antibodies.

Viral Markers. In particular embodiments, markers are expressed by unwanted virally-infected cells. Exemplary viruses include adenoviruses, arenaviruses, bunyaviruses, coronavirusess, flavirviruses, hantaviruses, hepadnaviruses, herpesviruses, papilomaviruses, paramyxoviruses, parvoviruses, picornaviruses, poxviruses, orthomyxoviruses, retroviruses, reoviruses, rhabdoviruses, rotaviruses, spongiform viruses or togaviruses. In additional embodiments, viral antigen markers include peptides expressed by CMV, cold viruses, Epstein-Barr, flu viruses, hepatitis A, B, and C viruses, herpes simplex, HIV, influenza, Japanese encephalitis, measles, polio, rabies, respiratory syncytial, rubella, smallpox, varicella zoster or West Nile virus.

As further particular examples, cytomegaloviral antigens include envelope glycoprotein B and CMV pp65; Epstein-Barr antigens include EBV EBNAI, EBV P18, and EBV P23; hepatitis antigens include the S, M, and L proteins of hepatitis B virus, the pre-S antigen of hepatitis B virus, HBCAG DELTA, HBV HBE, hepatitis C viral RNA, HCV NS3 and HCV NS4; herpes simplex viral antigens include immediate early proteins and glycoprotein D; HIV antigens include gene products of the gag, pol, and env genes such as HIV gp32, HIV gp41, HIV gp120, HIV gp160, HIV P17/24, HIV P24, HIV P55 GAG, HIV P66 POL, HIV TAT, HIV GP36, the Nef protein and reverse transcriptase; influenza antigens include hemagglutinin and neuraminidase; Japanese encephalitis viral antigens include proteins E, M-E, M-E-NS1, NS1, NS1-NS2A and 80% E; measles antigens include the measles virus fusion protein; rabies antigens include rabies glycoprotein and rabies nucleoprotein; respiratory syncytial viral antigens include the RSV fusion protein and the M2 protein; rotaviral antigens include VP7sc; rubella antigens include proteins E1 and E2; and varicella zoster viral antigens include gpI and gpII.

Additional particular exemplary viral antigen sequences include:

| Source | Sequence | SEQ ID NO. |
|---|---|---|
| Nef (66-97): | VGFPVTPQVPLRPMTYKAAVDLSHFLKEKGGL | 9 |
| Nef (116-145) | HTQGYFPDWQNYTPGPGVRYPLTFGWLYKL | 10 |
| Gag p17 (17-35) | EKIRLRPGGKKKYKLKHIV | 11 |
| Gag p17-p24 (253-284) | NPPIPVGEIYKRWIILGLNKIVRMYSPTSILD | 12 |
| Pol 325-355 (RT 158-188) | AIFQSSMTKILEPFRKQNPDIVIYQYMDDLY | 13 |

See Fundamental Virology, Second Edition, eds. Fields, B. N. and Knipe, D. M. (Raven Press, New York, 1991) for additional examples of viral antigens.

In particular embodiments disclosed herein, modified T cells recognize and destroy virally-infected cells. Alternatively, or in addition, modified monocytes/macrophages can remove viruses from peripheral tissue or the blood stream (extracellular) before cellular infection by a viral particle. B cells can also be modified to express broadly neutralizing antibodies. In one example, B cells can be modified to express broadly neutralizing anti-HIV antibodies.

In particular embodiments, the targeting agent targets HIV gag protein, gp120 or the Hepatitis B envelope protein (S domain).

Bacterial Markers. In particular embodiments, markers are expressed by cells associated with unwanted bacterial infections. Exemplary bacteria include anthrax; gram-negative *bacilli, chlamydia, diptheria, haemophilus influenza, Helicobacter pylori, malaria, Mycobacterium tuberculosis, pertussis* toxin, pneumococcus, rickettsiae, *staphylococcus, streptococcus* and tetanus.

As particular examples of bacterial antigen markers, anthrax antigens include anthrax protective antigen; gram-negative *bacilli* antigens include lipopolysaccharides; *haemophilus influenza* antigens include capsular polysaccharides; *diptheria* antigens include *diptheria* toxin; *Mycobacterium tuberculosis* antigens include mycolic acid, heat shock protein 65 (HSP65), the 30 kDa major secreted protein and antigen 85A; pertussis toxin antigens include hemagglutinin, pertactin, FIM2, FIM3 and adenylate cyclase; pneumococcal antigens include pneumolysin and pneumococcal capsular polysaccharides; rickettsiae antigens include rompA; streptococcal antigens include M proteins; and tetanus antigens include tetanus toxin.

In certain embodiments where the presence of bacteria is beneficial to the health of a microbiome, bacterial cells can also be wanted cell types.

Monocytes/macrophages are particularly useful to modify when the therapeutic objective is treatment of a bacterial infection. In one particular embodiment, monocytes/macrophages can be modified with a ligand recognizing the surface component lipoteichoic acid of *Staphyloccus aureus* or the *Staphylococcus aureus* clumping factor A (ClfA). Immunosuppressive $T_{REG}$ can be useful to modify when a bacteria is a wanted cell type.

Superbugs. In particular embodiments, lymphocytes are modified to target multi-drug resistant "superbugs". Examples of superbugs include *Enterococcus faecium, Clostridium difficile, Acinetobacter baumannii, Pseudomonas aeruginosa,* and *Enterobacteriaceae* (including *Escherichia coli, Klebsiella pneumoniae, Enterobacter* spp.).

Fungal Markers. In particular embodiments, markers are expressed by cells associated with unwanted fungal infections. Exemplary fungi include *candida, coccidiodes, cryptococcus, histoplasma, leishmania, plasmodium, protozoa, parasites, schistosomae, tinea, toxoplasma,* and *trypanosoma cruzi.*

As further particular examples of fungal antigens, coccidiodes antigens include spherule antigens; cryptococcal antigens include capsular polysaccharides; histoplasma antigens include heat shock protein 60 (HSP60); leishmania antigens include gp63 and lipophosphoglycan; *plasmodium falciparum* antigens include merozoite surface antigens, sporozoite surface antigens, circumsporozoite antigens, gametocyte/gamete surface antigens, protozoal and other parasitic antigens including the blood-stage antigen pf 155/RESA; schistosomae antigens include glutathione-S-transferase and paramyosin; tinea fungal antigens include trichophytin; toxoplasma antigens include SAG-1 and p30; and trypanosoma cruzi antigens include the 75-77 kDa antigen and the 56 kDa antigen.

Monocytes/macrophages are particularly useful to modify when the therapeutic objective is treatment of a fungal infection.

Autoimmune or Allergy Markers. In particular embodiments, markers are expressed by cells associated with unwanted autoimmune or allergic conditions. Exemplary autoimmune conditions include acute necrotizing hemorrhagic encephalopathy, allergic asthma, alopecia areata, anemia, aphthous ulcer, arthritis (including rheumatoid arthritis, juvenile rheumatoid arthritis, osteoarthritis, psoriatic arthritis), asthma, autoimmune thyroiditis, conjunctivitis, Crohn's disease, cutaneous lupus erythematosus, dermatitis (including atopic dermatitis and eczematous dermatitis), diabetes, diabetes mellitus, erythema nodosum leprosum, keratoconjunctivitis, multiple sclerosis, myasthenia gravis, psoriasis, scleroderma, Sjogren's syndrome, including keratoconjunctivitis sicca secondary to Sjogren's syndrome, Stevens-Johnson syndrome, systemic lupus erythematosis, ulcerative colitis, vaginitis and Wegener's granulomatosis.

Examples of autoimmune antigens include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of allergic antigens include pollen antigens such as Japanese cedar pollen antigens, ragweed pollen antigens, rye grass pollen antigens, animal derived antigens (such as dust mite antigens and feline antigens), histocompatibility antigens, and penicillin and other therapeutic drugs.

Immunosuppressive $T_{REG}$ can be useful to modify to protect wanted cells from autoimmune attack or to reduce immune system activity in an area. Exemplary wanted cells to protect from autoimmune attack include neurons in multiple sclerosis or amylotrophic lateral sclerosis; connective tissue in rheumatoid arthritis; colon epithelium in Chrohn's disease; and the pancreas in Diabetes mellitus type 1. In one particular embodiment, $T_{REG}$ are modified to express a chimeric antigen receptor (CAR) against KIR4.1 (a potassium channel) that has been identified as an immune target in multiple sclerosis.

Without limiting any of the foregoing examples, markers can also include B-cell targets, TNF receptor superfamily members, Hedgehog family members, receptor tyrosine kinases, proteoglycan-related molecules, TGF-β superfamily members, Wnt-related molecules, T-cell targets, dendritic cell targets, NK cell targets, a monocyte/macrophage cell targets, and angiogenesis targets.

Without limiting any of the foregoing examples, markers can also include CEACAM6, c-Met, EGFR, ErbB2, ErbB3, ErbB4, EphA2, IGF1R, GHRHR, GHR, FLT1, KDR, FLT4, CD44v6, CA125, CEA, BTLA, TGFBR2, TGFBR1, IL6R, gp130, TNFR1, TNFR2, PD1, PD-L1, PD-L2, HVEM, mesothelin, PSMA, RANK, ROR1, TNFRSF4, TWEAK-R, HLA, tumor or pathogen derived peptides bound to HLA (such as from hTERT, tyrosinase, or WT-1), LTβR, LIFRβ, LRP5, MUC1, OSMRβ, TCRα, TCRβ, B7H4, TLR7, TLR9, PTCH1, PTCH1, Robo1, α-fetoprotein (AFP) or Frizzled.

Targeting Agents. Targeting agents include any binding domain capable of (i) expression by a lymphocyte; and (ii) binding to a marker associated with a target. Binding of the targeting agent to the marker then mediates destruction or protection of the target.

Binding domains include any substance that binds to another substance to form a complex. Examples of binding domains include cell marker ligands, receptor ligands, antibodies, peptides, peptide aptamers, receptors and chimeric antigen receptors (CAR) or combinations thereof. As will be understood by one of ordinary skill in the art, targeting agent binding domains can include the same components, options and identification methods as described above in relation to lymphocyte-directing agent binding domains with altered specificity, as appropriate.

Targeting agent binding domains can particularly include any peptide that specifically binds a marker on a targeted cell. Sources of targeting agent binding domains include antibody variable regions from various species (which can be in the form of antibodies, sFvs, scFvs, Fabs, scFv-based grababody, or soluble VH domain or domain antibodies). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

An alternative source of targeting agent binding domains includes sequences that encode random peptide libraries or sequences that encode an engineered diversity of amino acids in loop regions of alternative non-antibody scaffolds, such as scTCR (see, e.g., Lake et al., *Int. Immunol.* 11:745, 1999; Maynard et al., *J. Immunol. Methods* 306:51, 2005; U.S. Pat. No. 8,361,794), fibrinogen domains (see, e.g., Weisel et al., *Science* 230:1388, 1985), Kunitz domains (see, e.g., U.S. Pat. No. 6,423,498), designed ankyrin repeat proteins (DARPins) (Binz et al., *J. Mol. Biol.* 332:489, 2003 and Binz et al., *Nat. Biotechnol.* 22:575, 2004), fibronectin binding domains (adnectins or monobodies) (Richards et al., *J. Mol. Biol.* 326:1475, 2003; Parker et al., *Protein Eng. Des. Selec.* 18:435, 2005 and Hackel et al. (2008) *J. Mol. Biol.* 381:1238-1252), cysteine-knot miniproteins (Vita et al. (1995) *Proc. Nat'l. Acad. Sci.* (*USA*) 92:6404-6408; Martin et al. (2002) *Nat. Biotechnol.* 21:71, 2002 and Huang et al. (2005) *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), lipocalin domains (see, e.g., WO 2006/095164, Beste et al., *Proc. Nat'l. Acad. Sci.* (*USA*) 96:1898, 1999 and Schönfeld et al., *Proc. Nat'l. Acad. Sci.* (*USA*) 106:8198, 2009), V-like domains (see, e.g., US Patent Application Publication No. 2007/0065431), C-type lectin domains (Zelensky and Gready, *FEBS J.* 272:6179, 2005; Beavil et al., *Proc. Nat'l. Acad. Sci.* (*USA*) 89:753, 1992 and Sato et al., *Proc. Nat'l. Acad. Sci.* (*USA*) 100:7779, 2003), mAb² or Fcab™ (see, e.g., PCT Patent Application Publication Nos. WO 2007/098934; WO 2006/072620), armadillo repeat proteins (see, e.g., Madhurantakam et al., *Protein Sci.* 21: 1015, 2012; PCT Patent Application Publication No. WO 2009/040338), affilin (Ebersbach et al., *J. Mol. Biol.* 372: 172, 2007), affibody, avimers, knottins, fynomers, atrimers, cytotoxic T-lymphocyte associated protein-4 (Weidle et al., *Cancer Gen. Proteo.* 10:155, 2013) or the like (Nord et al., *Protein Eng.* 8:601, 1995; Nord et al., *Nat. Biotechnol.* 15:772, 1997; Nord et al., *Euro. J. Biochem.* 268:4269, 2001; Binz et al., *Nat. Biotechnol.* 23:1257, 2005; Boersma and Plückthun, *Curr. Opin. Biotechnol.* 22:849, 2011).

In some embodiments, a binding domain is a single chain T cell receptor (scTCR) comprising $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or comprising $V_\alpha$-$C_\alpha$, $V_\beta$-$C_\beta$, $V_\alpha$-$V_\beta$ pair specific for a target of interest (e.g., peptide-MHC complex).

In another embodiment, the targeting agent is an unwanted cell targeting agent and the binding domain can be an antibody targeting PSMA. A number of antibodies specific for PSMA are known to those of skill in the art and can be readily characterized for sequence, epitope binding, and affinity. Unwanted cell targeting agent binding domains can also include anti-Mesothelin ligands (associated with treating ovarian cancer, pancreatic cancer, and mesothelioma); anti-WT-1 (associated with treating leukemia and ovarian cancer); anti-HIV-gag (associated with treating HIV infections); or anti-cytomegalovirus (associated with treating CMV diseases such as herpes virus). As will be understood by one of ordinary skill in the art, the unwanted cell targeting agent binding domain can be any ligand that binds to any marker associated with an unwanted cell type as described herein.

In one embodiment, the targeting agent is an unwanted cell targeting agent and the binding domain can be an antibody targeting CD19. In some embodiments, a binding domain is a single chain Fv fragment (scFv) that comprises VH and VL regions specific for CD19. In certain embodiments, the $V_H$ and $V_L$ regions are human. Exemplary $V_H$ and $V_L$ regions include the segments of anti-CD19 specific monoclonal antibody FMC63. In particular embodiments, the scFV is a human or humanized ss comprising a variable light chain comprising a CDRL1 sequence of RASQDISKYLN (SEQ ID NO. 14), CDRL2 sequence of SRLHSGV (SEQ ID NO. 15), and a CDRL3 sequence of GNTLPYTFG (SEQ ID NO. 16). In other embodiments, the scFV is a human or humanized ScFv comprising a variable heavy chain comprising CDRHI sequence of DYGVS (SEQ ID NO. 17), CDRH2 sequence of VTWGSETTYYNSALKS (SEQ ID NO. 18), and a CDRH3 sequence of YAMDYWG (SEQ ID NO. 19). Other CD19-targeting antibodies such as SJ25C1 and HD37 are known. (SJ25C1: Bejcek et al. Cancer Res 2005, PMID 7538901; HD37: Pezutto et al. JI 1987, PMID 2437199). SEQ ID NO. 20 provides the anti-CD19 scFv (VH-VL) FMC63 DNA sequence and SEQ ID NO. 21 provides the anti-CD19 scFv (VH-VL) FMC63 amino acid sequence.

In another embodiment, the targeting agent is an unwanted cell targeting agent and the binding domain can be an antibody targeting RORI. In a particular embodiment, the scFV is a human or humanized scFv comprising a variable light chain comprising a CDRL1 sequence of ASGFDFSAYYM (SEQ ID NO. 22), CDRL2 sequence of TIYPSSG (SEQ ID NO. 23), and a CDRL3 sequence of ADRATYFCA (SEQ ID NO. 24). In other embodiments, the scFV is a human or humanized scFv comprising a variable heavy chain comprising CDRH1 sequence of DTIDWY (SEQ ID NO. 25), CDRH2 sequence of VQSDGSYTKRPGVPDR (SEQ ID NO. 26), and a CDRH3 sequence of YIGGYVFG (SEQ ID NO. 27). A number of antibodies specific for RORI are known to those of skill in the art and can be readily characterized for sequence, epitope binding, and affinity.

In certain embodiments, targeting agent binding domains comprise a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a TCR $V_\alpha$, $V_\beta$, $C_\alpha$, or $C_\beta$, wherein each CDR comprises zero changes or at most one, two, or three changes, from a TCR or fragment or derivative thereof that specifically binds to target of interest.

In certain embodiments, targeting agent binding domain $V_\alpha$, $V_\beta$, $C_\alpha$, or $C_\beta$ region of the present disclosure can be derived from or based on a $V_\alpha$, $V_\beta$, $C_\alpha$, or $C_\beta$ of a known TCR (e.g., a high-affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR comprises zero changes or at most one, two, or three changes and provided a binding domain containing a modified $V_\alpha$, $V_\beta$, $C_\alpha$, or $C_\beta$ region can still specifically bind its target with an affinity similar to wild type.

In certain embodiments, a binding domain $V_H$ region of the present disclosure can be derived from or based on a $V_H$ of a known monoclonal antibody and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ of a known monoclonal antibody. An insertion, deletion or substitution may be anywhere in the $V_H$ region, including at the amino- or carboxy-terminus or both ends of this region, provided that each CDR comprises zero changes or at most one, two, or three changes and provided a binding domain containing the modified $V_H$ region can still specifically bind its target with an affinity similar to the wild type binding domain.

In further embodiments, a $V_L$ region in a binding domain of the present disclosure is derived from or based on a $V_L$ of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the $V_L$ of the known monoclonal antibody. An insertion, deletion or substitution may be anywhere in the $V_L$ region, including at the amino- or carboxy-terminus or both ends of this region, provided that each CDR comprises zero changes or at most one, two, or three changes and provided a binding domain containing the modified $V_L$ region can still specifically bind its target with an affinity similar to the wild type binding domain.

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region ($V_L$) or to a heavy chain variable region ($V_H$), or both, wherein each CDR comprises zero changes or at most one, two, or three changes, from a monoclonal antibody or fragment or derivative thereof that specifically binds to target of interest.

As stated, cell-targeting agents disclosed herein include chimeric antigen receptors. "Chimeric antigen receptors" or "CARs" refer to synthetically designed receptors comprising at least a binding domain and an effector domain and optionally a spacer domain and/or a transmembrane domain. Binding domains are described elsewhere herein.

Effector domains are capable of transmitting functional signals to a cell. In certain embodiments, an effector domain will directly or indirectly promote a cellular response by associating with one or more other proteins that directly promote a cellular response. Effector domains can provide for activation of at least one function of a transduced lymphocyte expressing the CAR upon binding to the marker expressed on a targeted cell. Activation of the lymphocyte can include one or more of proliferation, differentiation, activation or other effector functions. In particular embodiments, the delivered polynucleotide encodes for the effector domain.

An effector domain may include one, two, three or more receptor signaling domains, intracellular signaling domains, costimulatory domains, or combinations thereof. Any intracellular effector domain, costimulatory domain or both from any of a variety of signaling molecules (e.g., signal transduction receptors) may be used in the CARs of this disclosure.

Exemplary effector domains include those from 4-1BB, CD3ε, CD3δ, CD3ζ, CD27, CD28 (e.g., SEQ ID NO.:28), CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination thereof.

T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or iTAMs. Examples of iTAM containing primary cytoplasmic signaling sequences include those derived from CD3 zeta, FeR gamma, CD3 gamma, CD3 delta, CD3 epsilon, CD5, CD22, CD79a, CD79b, and CD66d.

In particular embodiments, an effector domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

Examples of intracellular signaling domains include the cytoplasmic sequences of the CD3 zeta chain, and/or co-receptors that act in concert to initiate signal transduction following CAR engagement, as well as any derivative or variant of these sequences and any synthetic sequence that has the same functional capability. In particular embodiments, an intracellular signaling domain of a CAR can be designed to comprise an intracellular signaling domain combined with any other desired cytoplasmic domain(s). For example, the intracellular signaling domain of a CAR can comprise an intracellular signaling domain and a costimulatory signaling region. The costimulatory signaling region refers to a portion of the CAR comprising the intracellular domain of a costimulatory molecule. A costimulatory molecule is a cell surface molecule other than the expressed marker ligand that is required for a response of lymphocytes to a marker. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, and a ligand that specifically binds with CD83.

In certain embodiments, CAR polynucleotides can comprise a sequence encoding for a spacer region. The length of the spacer region can be customized for individual markers on targets to optimize target recognition and destruction or protection. In particular embodiments, a spacer length can be selected based upon the location of a marker epitope, affinity of an antibody for the epitope, and/or the ability of the lymphocytes expressing the CAR to proliferate in vitro and/or in vivo in response to marker recognition.

Typically a spacer region is found between the binding domain and a transmembrane domain of the CAR. Spacer regions can provide for flexibility of the binding domain and allows for high expression levels in the modified cells. In particular embodiments, a spacer region can have at least 10 to 250 amino acids, at least 10 to 200 amino acids, at least 10 to 150 amino acids, at least 10 to 100 amino acids, at least 10 to 50 amino acids or at least 10 to 25 amino acids and including any integer between the endpoints of any of the listed ranges. In further embodiments, a spacer region has 250 amino acids or less; 200 amino acids or less, 150 amino acids or less; 100 amino acids or less; 50 amino acids or less; 40 amino acids or less; 30 amino acids or less; 20 amino acids or less; or 10 amino acids or less.

In particular embodiments, spacer regions can be derived from a hinge region of an immunoglobulin like molecule, for example all or a portion of the hinge region from a human IgG1, human IgG2, a human IgG3, or a human IgG4. Hinge regions can be modified to avoid undesirable structural interactions such as dimerization. In some embodiments, all or a portion of a hinge region can be combined with one or more domains of a constant region of an immunoglobulin. For example, a portion of a hinge region can be combined with all or a portion of a CH2 or CH3 domain or variant thereof.

CARs disclosed herein can also include transmembrane domains. In particular embodiments, the CAR polynucleotide encodes the transmembrane domain. The transmembrane domain provides for anchoring of the CAR in the lymphocyte membrane. The transmembrane domain may be derived either from a natural or a synthetic source. When the source is natural, the domain may be derived from any membrane-bound or transmembrane protein. Transmembrane regions comprise at least the transmembrane region(s) of) the alpha, beta or zeta chain of the T-cell receptor, CD28, CD3, CD45, CD4, CD5, CD9, CD16, CD22; CD33, CD37, CD64, CD80, CD86, CD134, CD137 and CD154. In further particular embodiments, synthetic or variant transmembrane domains comprise predominantly hydrophobic residues such as leucine and valine.

In a particular embodiment, the CAR comprises a P28z fusion receptor composed of a single-chain antibody (scFv) specific for the extracellular domain of PSMA (J591) combined with CD28 and CD3ζ cytoplasmic signaling domains. In another embodiment, the CAR comprises a P28z CAR of SEQ ID NO. 94. SEQ ID NO. 94 includes murine components and was utilized in studies described herein. Amino acid positions 1-797 include the anti-PSMA scFv (J592) whereas positions 797-1477 include the murine CD8 transmembrane domain, murine CD28 signaling domain and the murine CD3zeta signaling domain. Any P28z domain can be individually replaced with optimized domains. In particularized embodiments, the transmembrane domain and signaling domains within positions 797-1477 of SEQ ID NO. 94 can be particularly replaced with domains optimized for use in humans or other animals. In additional embodiments, any whole or portion of a binding domain, any whole or portion of an effector domain, any whole or portion of a spacer domain and/or any whole or portion of a transmembrane domain can be optimized for use in humans or other animals. In additional embodiments, the P28z CAR is optimized for use in humans. When optimized for humans, the P28z CAR can have lowered or no immunogenicity in humans and have a lower number of non-immunogenic epitopes compared to non-human antibodies.

Endosomal Release Agents. As used herein, "endosomal release agents" include any compound or peptide sequence that facilitates cargo exit from the endosome of a lymphocyte. Exemplary endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, amphiphilic block copolymers and dendrimers with masked or unmasked cationic or anionic charges.

Many endosomal release agents are adapted from viral elements that promote escape from the endosome and deliver polynucleotides intact into the nucleus. As one particular example, the H5WYG peptide can be used to induce the lysis of membranes at low pH. The histidine-rich peptide H5WYG is a derivative of the N-terminal sequence of the HA-2 subunit of the influenza virus hemagglutinin in which 5 of the amino acids have been replaced with histidine residues. H5WYG is able to selectively destabilize membranes at a slightly acidic pH as the histidine residues are protonated. The E1 protein from Semliki Forrest virus is also a useful endosomal release agent.

In particular embodiments, endosomal release agents include a hydrophobic membrane translocation sequence (MTS). An exemplary hydrophobic MTS-containing peptide is RFGF having the amino acid sequence AAVALLPAVL-LALLAP (SEQ ID NO. 29). An RFGF analogue (e.g., amino acid sequence AALLPVLLAAP (SEQ ID NO. 30)) containing a hydrophobic MTS can also be used.

Additional exemplary endosomal release agents include:

| Source | Sequence | SEQ ID NO. |
| --- | --- | --- |
| Influenza virus hemagglutinin HA-2 | GLFEAIAGFIENGWEG | 31 |
| TAT of HIV | YGRKKRRQRRR | 32 |
| N-terminal region of the S protein of duck hepatitis B | MSGTFGGILAGLIGLL | 33 |
| S protein of woodchuck hepatitis B | MSPSSLLGLLAGLQVV | 34 |
| Synthetic, Duguid et al. 1998 | GLFEALLELLESLWELL | 35 |
| Synthetic, Gupta & Kothekar, 1997 | LKKLLKKLLKKLLKKL | 36 |
| Derossi et al., J. Biol. Chem. 269: 10444, 1994 | RQIKIWFQNRRMKWKK | 37 |
| Tat fragment (48-60) | GRKKRRQRRRPPQC | 38 |

| Source | Sequence | SEQ ID NO. |
|---|---|---|
| Chaloin et al., Biochem. Biophys. Res. Commun., 243: 601, 1998 | GALFLGWLGAAGSTMGAWSQP KKKRKV | 39 |
| PVEC | LLIILRRRIRKQAHAHSK | 40 |
| Transportan | GWTLNSAGYLLKINLKALAALAK KIL | 41 |
| Amphiphilic model peptide; Oehlke et al., Mol. Ther., 2: 339, 2000 | KLALKLALKALKAALKLA | 42 |
| Arg$_9$ | RRRRRRRRR | 43 |
| LL-37 | LLGDFFRKSKEKIGKEFKRIVQRI KDFLRNLVPRTES | 44 |
| Cecropin P1 | SWLSKTAKKLENSAKKRISEGIAI AIQGGPR | 45 |
| α-defensin | ACYCRIPACIAGERRYGTCIYQG RLWAFCC | 46 |
| β-defensin | DHYNCVSSGGQCLYSACPIFTKI QGTCYRGKAKCCK | 47 |
| Bactenecin | RKCRIVVIRVCR | 48 |
| PR-3 | RRRPRPPYLPRPRPPPFFPPRL PPRIPPGFPPRFPPRFPGKR- NH$_2$ | 49 |
| Indolicidin | ILPWKWPWWPWRR-NH2 | 50 |

Nuclear Localization Signals. "Nuclear localization signals" (NLS) refer to sequences that direct associated sequences into the nucleus of a cell. Generally, NLS are a class of short amino acid sequences from 3 to 100 amino acids in length, from 3 to 50, 4 to 30, or 4 to 20 amino acids in length.

Exemplary NLS sequences include (i) monopartite NLS exemplified by the SV40 large T antigen NLS (PKKKRKV) (SEQ ID NO: 51); (ii) bipartite NLS consisting of two basic domains separated by a variable number of spacer amino acids and exemplified by the *Xenopus* nucleoplasmin NLS (KRXXXXXXXXXXKKKL) (SEQ ID NO: 52); and (iii) noncanonical sequences such as M9 of the hnRNP A1 protein, the influenza virus nucleoprotein NLS, and the yeast Gal4 protein NLS (Dingwall and Laskey, Trends Biochem Sci 16:478-481, 1991). In particular embodiments, the NLS can be a highly cationic or basic peptide. In other embodiments, the NLS comprises two or more Arg or Lys amino acid residues. In further embodiments, the NLS can bind cytosolic proteins, such as importins and karyopherins, which recognize and transport NLS-containing sequences to the nuclear pore complex.

In particular embodiments, to direct import of delivered polynucleotides, particularly plasmid DNA, into the nucleus, polynucleotides (in one embodiment nanoparticle-encapsulated plasmids) can be conjugated to the SV40 T-Ag-derived NLS peptides. Exemplary SV40 T-Ag-derived NLS peptides include: PKKKRKV (SEQ ID NO. 51); PKKKRMV (SEQ ID NO. 53); PKKKRKVEDP (SEQ ID NO. 54); PKKGSKKA (SEQ ID NO. 55); PKTKRKV (SEQ ID NO. 56); CGGPKKKRKVG (SEQ ID NO. 57); PKK-KIKV (SEQ ID NO. 58); CYDDEATADSQHSTPPKK-KRKVEDPKDFESELLS (SEQ ID NO. 59); and CGYGP-KKKRKVGG (SEQ ID NO. 60).

Additional exemplary NLS sequences include:

| Source | Sequence | SEQ ID NO. |
|---|---|---|
| Polyoma large T protein | PKKARED | 61 |
| Polyoma large T protein | CGYGVSRKRPRPG | 62 |
| SV40 VP1 capsid polypeptide | APTKRKGS | 63 |
| Polyoma virus major capsid protein VP1 | APKRKSGVSKC | 64 |
| SV40 VP2 capsid protein | PNKKKRK | 65 |
| Polyoma virus capsid protein VP2 | EEDGPQKKKRRL | 66 |
| Yeast histone H2B | GKKRSKA | 67 |

-continued

| Source | Sequence | SEQ ID NO. |
|---|---|---|
| Adenovirus E1a | KRPRP | 68 |
| Adenovirus type 2/5 E1a | CGGLSSKRPRP | 69 |
| Xenopus NLS2 | LKDKDAKKSKQE | 70 |
| v-Rel or p59$^{v-rel}$ | GNKAKRQRST | 71 |
| Influenza A NS1 protein | PFLDRLRRDQK | 72 |
| Human lamin A | SVTKKRKLE | 73 |
| Xenopus lam in A | SASKRRRLE | 74 |
| Adenovirus 5 DBP | PPKKRMRRRIE | 75 |
| Rat glucocorticoid receptor | YRKCLQAGMNLEARKTKK KIKGIQQATA | 76 |
| Human estrogen receptor | RKDRRGGRMLKHKRQRD DGEGRGEVGSAGDMRAM INACIDNLWPSPLMIKRSK K | 77 |
| Rabbit progesterone receptor | RKFKKFNK | 78 |
| c-myb gene product | PLLKKIKQ | 79 |
| N-myc gene product | PPQKKIKS | 80 |
| p53 | PQPKKKP | 81 |
| c-erb-A gene product | SKRVAKRKL | 82 |
| Yeast ribosomal protein L29 | MTGSKTRKHRGSGA | 83 |
| Yeast ribosomal protein L29 | RHRKHP | 84 |
| Yeast ribosomal protein L29 | KRRKHP | 85 |
| Yeast ribosomal protein L29 | KYRKHP | 86 |
| Yeast ribosomal protein L29 | KHRRHP | 87 |
| Yeast ribosomal protein L29 | KHKKHP | 88 |
| Yeast ribosomal protein L29 | RHLKHP | 89 |
| Hepatitis B core antigen | PETTVVRRRGRSPRRRTP SPRRRRSPRRRRSQS | 90 |
| Viral jun | ASKSRKRKL | 91 |
| Human T-cell leukemia virus Tax trans-activator protein | GGLCSARLHRHALLAT | 92 |
| Mouse nuclear Mx1 protein | DTREKKKFLKRRLLRLDE | 93 |

Exemplary NLS are also described in Cokol et al., 2000, EMBO Reports, 1(5):411-415; Boulikas, 1993, Crit. Rev. Eukaryot. Gene Expr., 3:193-227; Collas et al., 1996, Transgenic Research, 5: 451-458; Collas and Alestrom, 1997, Biochem. Cell Biol. 75: 633-640; Collas and Alestrom, 1998, Transgenic Research, 7: 303-309; Collas and Alestrom, 1996, Mol. Reprod. Devel., 45:431-438, and U.S. Pat. Nos. 7,531,624; 7,498,177; 7,332,586; and 7,550,650.

Nanocarriers. Compositions disclosed herein include nanocarriers. Nanocarriers can include a porous nanoparticle at least substantially covered by a coating. In particular embodiments, polynucleotides and optionally NLSs can be found within the porous nanoparticle whereas optional lymphocyte-directing agents and endosomal release agents can be anchored to the coating.

Porous Nanoparticles. Porous nanoparticles of particular compositions can be constructed from any material capable of forming a porous network. Exemplary materials include a variety of material including, without limitation, biocompatible polymers, metals, transition metals and metalloids. Exemplary biocompatible polymers include, but not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PHB-HHx), poly(lactide), poly(caprolactone) (PCL), poly(lactide-co-glycolide) (PLG), poly(lactic-co-glycolic acid) (PLGA), poly(vinyl alcohol) (PVA), silk, soy protein, and soy protein isolate, alone or in combination with any other polymer composition, in any concentration and in any ratio. Blending different polymer types in different ratios using various grades can result in characteristics that borrow from each of the contributing polymers. Various terminal group chemistries can also be adopted. Exemplary metals, transition metals and metalloids include lithium, magnesium, zinc, aluminum and silica. In one embodiment, the porous nanoparticles comprise silica. The exceptionally high surface area of mesoporous silica (exceeding 1,000 m$^2$/g) enables polynucleotide loading at levels exceeding conventional DNA carriers such as liposomes or polymer conjugates. In additional embodiments, pores range in size from 10-20 nm.

Useful nanocarriers of particular embodiments also include those based on (i) lipid-based delivery systems, including cationic lipids, ionizable cationic lipids, lipid-like molecules and pH-sensitive amphiphiles; and/or (ii) polymeric RNA/DNA delivery systems such as polyethylenimine (PEI)-based polymeric vectors, chitosan-based vectors, dendrimers (highly branched, spherical macromolecules synthesized from poly-amidoamine (PAMAM) and polypropylene iminie (PPI), and block copolymers such as PAA/BMA/DMAEMA and PDMAEMA.

The porous nanoparticles can be a variety of different shapes, including spheroidal, cuboidal, pyramidal, oblong, cylindrical, toroidal, and the like. The polynucleotides can be included in the porous nanoparticles in a variety of ways. For example, the polynucleotides can be encapsulated in the porous nanoparticles. In other aspects, the polynucleotides can be associated (e.g., covalently and/or non-covalently) with the surface or close underlying vicinity of the surface of the porous nanoparticles. In some embodiments, the polynucleotides can be incorporated in the porous nanoparticles e.g., integrated in the material of the porous nanoparticles. For example, the polynucleotides can be incorporated into a polymer matrix of polymer nanoparticles. One of ordinary skill in the art will appreciate the various ways to carry the polynucleotides so as to allow delivery of the polynucleotide molecules to the lymphocytes.

In particular embodiments, porous nanoparticles include liposomes. Liposomes are microscopic vesicles consisting of at least one concentric lipid bilayer. Vesicle-forming lipids are selected to achieve a specified degree of fluidity or rigidity of the final complex. In some embodiments, liposomes provide a lipid composition that is an outer layer surrounding a porous nanoparticle.

Liposomes can be neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including but not limited to dioleoylphosphatidylethanolamine (DOPE), with a hydrocarbon chain length in the range of 14-22, and saturated or with one or more double C═C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palm itoyloleoylphosphatidylcholine (POPC), palm itoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles. In particular embodiments, lipids used to create liposomes disclosed herein include cholesterol, hydrogenated soy phosphatidylcholine (HSPC) and, the derivatized vesicle-forming lipid PEG-DSPE.

Methods of forming liposomes are described in, for example, U.S. Pat. Nos. 4,229,360; 4,224,179; 4,241,046; 4,737,323; 4,078,052; 4,235,871; 4,501,728; and 4,837,028, as well as in Szoka et al., Ann. Rev. Biophys. Bioeng. 9:467 (1980) and Hope et al., Chem. Phys. Lip. 40:89 (1986).

The size of the nanocarriers can vary over a wide range and can be measured in different ways. For example, the nanocarriers of the present disclosure can have a minimum dimension of 100 nm. The nanocarriers of the present disclosure can also have a minimum dimension of equal to or less than 500 nm, less than 150 nm, less than 100 nm, less than 90 nm, less than 80 nm, less than 70 nm, less than 60 nm, less than 50 nm, less than 40 nm, less than 30 nm, less than 20 nm, or less than 10 nm. In certain embodiments, the nanocarriers can have a minimum dimension ranging between 5 nm and 500 nm, between 10 nm and 100 nm, between 20 nm and 90 nm, between 30 nm and 80 nm, between 40 nm and 70 nm, and between 40 nm and 60 nm. In some embodiments, the dimension is the diameter of nanoparticles or coated nanoparticles. In some embodiments, a population of nanocarriers of the present disclosure can have a mean minimum dimension of equal to or less than 500 nm, less than 100 nm, less than 90 nm, less than 80 nm, less than 70 nm, less than 60 nm, less than 50 nm, less than 40 nm, less than 30 nm, less than 20 nm, or less than 10 nm. In certain embodiments, a population of nanocarriers in a composition of the present disclosure can have a mean diameter ranging between 5 nm and 500 nm, between 10 nm and 100 nm, between 20 nm and 90 nm, between 30 nm and 80 nm, between 40 nm and 70 nm, and between 40 nm and 60 nm. Dimensions of the nanocarriers can be determined using, e.g., conventional techniques, such as dynamic light-scattering and/or electron microscopy.

In particular embodiments, the compositions include protocells as nanocarriers. Protocells can be formed via fusion of liposomes to porous silica nanoparticles. The high pore volume and surface area of the spherical mesoporous silica core allow high-capacity encapsulation of a spectrum of cargos, including plasmid DNA. The supported lipid bilayer, whose composition can be modified for specific biological applications, can serve as a modular, reconfigurable scaffold, allowing the attachment of a variety of molecules, such as lymphocyte-directing agents, to provide cell-specific targeting and controlled intracellular trafficking. As provided further herein, protocells can efficiently introduce polynucleotides into lymphocytes.

Figure 2A:
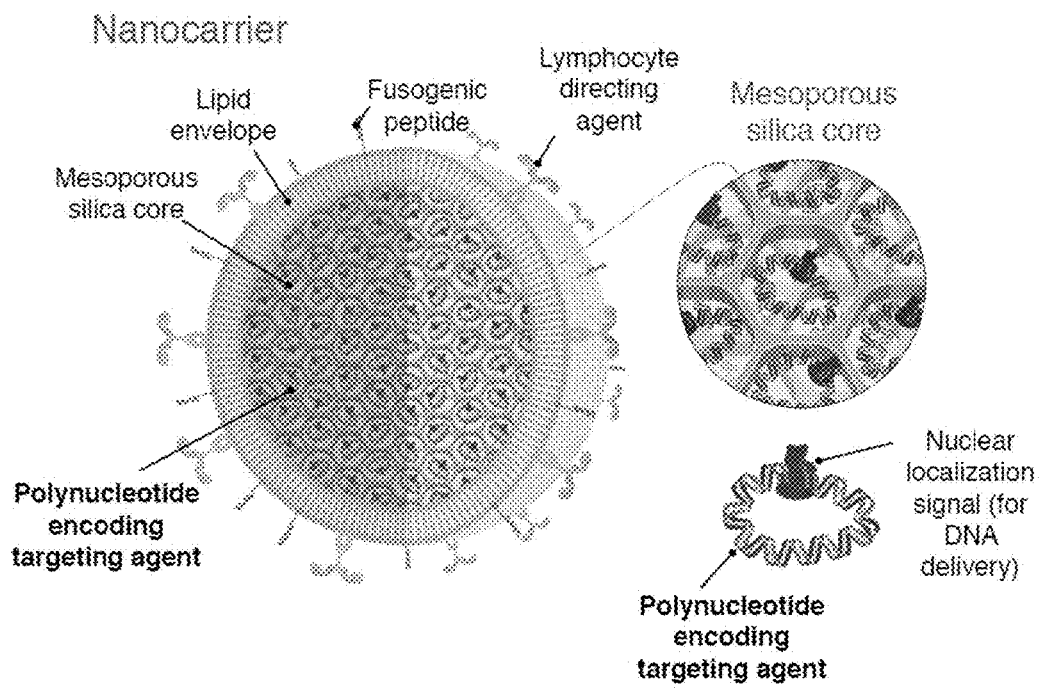
FIGS. 2A and 2B.
Figure 2B:
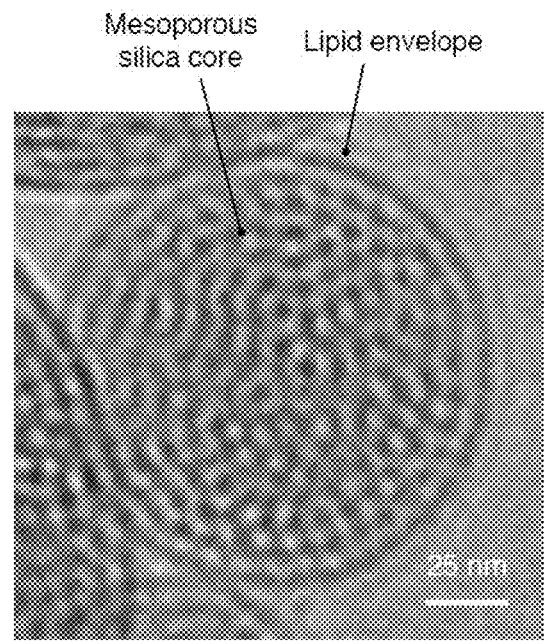

In one particular embodiment intended to illustrate the foregoing, anti-CD3 antibodies can be coupled onto protocell nanocarriers to selectively target the nanocarriers to T cells for rapid receptor-induced endocytosis. Protocells can be formed via fusion of liposomes with porous silica nanoparticles (FIG. 2A, FIG. 2B). The high pore volume and surface area of the spherical mesoporous silica core allow high-capacity encapsulation of a spectrum of cargos, including plasmid DNA. The membrane serves as a modular scaffold for the attachment of a variety of targeting moieties. In the embodiment depicted in FIGS. 2A and 2B, the pH-sensitive fusogenic peptide HSWYG is tethered to the nanocarrier surface to facilitate endosomal escape. The plasmid DNA was also modified before encapsulation into nanoparticles with the SV40 large T antigen nuclear localization signal peptide (FIG. 2A).

Particular nanocarrier embodiments include:

| Selected Lymphocyte Population | Lymphocyte-Directing Agent | Target | Targeting Agent | Endosomal Release Agent | NLS |
|---|---|---|---|---|---|
| T cells | Anti-CD3 antibody | Leukemia cells | Anti-CD19 CAR (1928zeta or 194-1BBzeta) | Fusogenic peptide H5WYG | SV40 |
| CD8 T cells | Anti-CD8 antibody | Ovarian cancer cells | Anti-mesothelin CAR (with or without integrated costimulatory domains) | "Proton Sponge" effect of polymeric nanoparticles | NLS Ku70 |
| T cells | Anti-LFA antibody | Pancreatic cancer cells | Affinity-enhanced T cell receptor (TCR) specific for mesothelin | TAT peptide | None |
| T cells | 4-1BB (CD137) targeting aptamers | HIV-infected cells | HIV-gag protein-specific T-cell receptor | Cationic-polymer-based nanocarrier | hnRNP (M9) |
| Monocytes/ macrophages | Anti-CD14 antibodies | *Staphylococcus aureus* | Clumping factor A (ClfA) | Pas nona-arginine (PR9) | SV40 |
| NK cells | Anti-CD56 antibodies | Prostate cancer cells | Anti-PSMA CAR (P28zeta or P4-1BB zeta) | Cationic lipid-based nanocarrier | None |
| T$_{REG}$ | Anti-CTLA-4 or anti-GARP antibodies | Neurons | CAR specific for KIR4.1 for the treatment of multiple sclerosis | Cationic polymer-based nanocarrier | SV40 |
| Hematopoietic stem cells | Anti-CD34 antibodies | Leukemia cells | Affinity-enhanced T cell receptor (TCR) specific for Wilms' tumor antigen (WT1) | "Proton Sponge" effect of polymeric nanoparticles | NLS Ku70 |

Compositions. The nanoparticles, porous nanoparticles and nanocarriers (all collectively referred to herein as "active ingredients") disclosed herein can be provided as part of compositions that comprise, consist of or consist essentially of the nanoparticles, porous nanoparticles and/or nanocarriers. The compositions can be formulated for administration to subjects.

In some embodiments, the active ingredients are provided as part of a composition that can comprise, for example, at least 0.1% w/v of active ingredient(s); at least 1% w/v of active ingredient(s); at least 10% w/v of active ingredient(s); at least 20% w/v of active ingredient(s); at least 30% w/v of active ingredient(s); at least 40% w/v of active ingredient(s); at least 50% w/v of active ingredient(s); at least 60% w/v of active ingredient(s); at least 70% w/v of active ingredient(s); at least 80% w/v of active ingredient(s); at least 90% w/v of active ingredient(s); at least 95% w/v of active ingredient(s); or at least 99% w/v of active ingredient(s).

In other embodiments, the active ingredients are provided as part of a composition that can comprise, for example, at least 0.1% w/w of active ingredient(s); at least 1% w/w of active ingredient(s); at least 10% w/w of active ingredient(s); at least 20% w/w of active ingredient(s); at least 30% w/w of active ingredient(s); at least 40% w/w of active ingredient(s); at least 50% w/w of active ingredient(s); at least 60% w/w of active ingredient(s); at least 70% w/w of active ingredient(s); at least 80% w/w of active ingredient(s); at least 90% w/w of active ingredient(s); at least 95% w/w of active ingredient(s); or at least 99% w/w of active ingredient(s).

The compositions disclosed herein can be formulated for administration by, without limitation, injection, inhalation, infusion, perfusion, lavage or ingestion. The compositions disclosed herein can further be formulated for, without limitation, intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, compositions can be formulated as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days.

When formulated to treat cancer, the disclosed compositions can also include plasmid DNA carrying one or more anticancer genes selected from p53, RB, BRCA1, E1A, bcl-2, MDR-1, p21, p16, bax, bcl-xs, E2F, IGF-I VEGF, angiostatin, oncostatin, endostatin, GM-CSF, IL-12, IL-2, IL-4, IL-7, IFN-γ, TNF-α and/or HSV-tk. Compositions can also include or be administered in combination with one or more antineoplastic drugs including adriamycin, angiostatin, azathioprine, bleomycin, busulfane, camptothecin, carboplatin, carmustine, chlorambucile, chlormethamine, chloroquinoxaline sulfonamide, cisplatin, cyclophosphamide, cycloplatam, cytarabine, dacarbazine, dactinomycin, daunorubicin, didox, doxorubicin, endostatin, enloplatin, estramustine, etoposide, extramustinephosphat, flucytosine, fluorodeoxyuridine, fluorouracil, gallium nitrate, hydroxyurea, idoxuridine, interferons, interleukins, leuprolide, lobaplatin, lomustine, mannomustine, mechlorethamine, mechlorethaminoxide, melphalan, mercaptopurine, methotrexate, mithramycin, mitobronitole, mitomycin, mycophenolic acid, nocodazole, oncostatin, oxaliplatin, paclitaxel, pentamustine, platinum-triamine complex, plicamycin, prednisolone, prednisone, procarbazine, protein kinase C inhibitors, puromycine, semustine, signal transduction inhibitors, spiroplatin, streptozotocine, stromelysin inhibitors, taxol, tegafur, telomerase inhibitors, teniposide, thalidomide, thiamiprine, thioguanine, thiotepa, tiamiprine, tretamine, triaziquone, trifosfamide, tyrosine kinase inhibitors, uramustine, vidarabine, vinblastine, vinca alcaloids, vincristine, vindesine, vorozole, zeniplatin, zeniplatin or zinostatin.

Methods. Methods disclosed herein include treating subjects (humans, veterinary animals, livestock and research animals) with compositions, active ingredients, nanoparticles, porous nanoparticles and/or nanocarriers disclosed herein. Treating subjects includes delivering a therapeutically effective amount. An "effective amount" is the amount of a compound necessary to result in a desired physiological change in the subject. Effective amounts are often administered for research purposes. Effective amounts disclosed herein reduce the number of unwanted cell types in a subject.

A "prophylactic treatment" includes a treatment administered to a subject who does not display signs or symptoms of a disease or condition associated with or caused by a target or displays only early signs or symptoms of the disease or condition such that treatment is administered for the purpose of diminishing, preventing, or decreasing the risk of developing the disease or condition further. Thus, a prophylactic treatment functions as a preventative treatment against a disease or disorder associated with or caused by a target.

A "therapeutic treatment" includes a treatment administered to a subject who displays symptoms or signs of a disease or condition associated with or caused by a target and is administered to the subject for the purpose of diminishing or eliminating those signs or symptoms of the disease or condition.

"Therapeutically effective amounts" include those that provide effective amounts, prophylactic treatment and/or therapeutic treatment. Therapeutically effective amounts need not fully prevent or cure the disease or condition but can also provide a partial benefit, such as reduction in the number of unwanted targets; reduction of destruction of wanted targets; and/or a delay of onset or alleviation or improvement of at least one symptom of the disease or condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes an $IC_{50}$ as determined in cell culture against a particular target. Such information can be used to more accurately determine useful doses in subjects of interest.

The actual dose amount administered to a particular subject can be determined by a physician, veterinarian or researcher taking into account parameters such as physical and physiological factors including target, body weight, severity of condition, type of disease, previous or concurrent therapeutic interventions, idiopathy of the subject and route of administration.

Useful doses often range from 0.1 to 5 µg/kg or from 0.5 to 1 µg/kg. In other non-limiting examples, a dose can comprise 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other non-limiting examples, a dose can comprise 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly.

Exemplary methods disclosed herein include administering nanocarriers to a subject in need thereof. The nanocarriers are directed to chosen lymphocytes in the subject and are designed to be internalized by the lymphocytes. Once internalized, the nanocarriers further deliver a polynucleotide having a sequence that encodes a targeting agent. The polynucleotide modifies the lymphocytes to express the targeting agent, which subsequently binds a marker associated with the target. Upon binding, the lymphocytes can kill or otherwise trigger the destruction of unwanted targets such as unwanted cells, thereby treating a disease or condition associated with the unwanted cell type. Alternatively, upon binding, the lymphocytes can protect wanted targets such as wanted cells, thereby treating a disease or condition associated with unwanted destruction of the wanted cell type.

In another particular embodiment, nanocarriers can be loaded with polynucleotides (e.g., Transgenes) that encode for a defined tumor- or virus-specific TCR. Surface-anchored lymphocyte-directing agents that recognize T-cell-specific proteins enable the nanocarriers to selectively bind T-cells. Upon infusion into a subject's bloodstream, the nanocarriers can deliver TCR genes into T-cells, which can subsequently express this TCR on their surface. Equipped with a therapeutically relevant TCR, the T-cells can recognize and lyse malignant cells or virus-infected cells or other targeted unwanted cell types.

In additional embodiments, NK cells are selectively modified to express CARs or high-affinity TCRs. In additional embodiments, hematopoietic stem cells (HSCs) are selectively modified to express CARs or high-affinity TCRs. In additional embodiments, monocytes/macrophages cells are selectively modified to express CARs or high-affinity ligands specific for viruses, bacteria, fungus or yeast antigens. In additional embodiments, B cells are selectively modified to express tumor- or virus-specific antibodies. In additional embodiments, $T_{REG}$ cells are selectively modified to express CARs or high-affinity ligands specific for autoimmune markers, allergic reaction markers or beneficial bacteria.

Additional embodiments include methods of delivering pre-designed synthetic nanocarriers to lymphocytes (e.g., T-cells), in which the nanocarriers can be loaded with polynucleotides (e.g., plasmids) that encode a receptor for an antigen (e.g., a prostate tumor-targeting receptor P28z). Internalization of the nanocarriers can render transfected lymphocytes (e.g., T-cells) capable of lysing cells associated with the antigen (e.g., a prostate tumor). In some embodiments, delivery of the nanocarriers including the receptor genes into lymphocytes (e.g., T-cells) can include, e.g., (1) specific binding to the lymphocytes (e.g., T-cells), (2) internalization of the nanocarriers by the lymphocytes, (3) escape from endocytic vesicles into the cytoplasm after internalization, (4) release of the polynucleotide, which (5) can be transported into the nucleus of the lymphocytes and (6) transcribed to deliver genes for expressing a receptor for the antigen.

In particular embodiments, the methods are used to target unwanted cancer cells. Thus, the disclosed methods provide a new paradigm for the treatment of cancer that can involve programming circulating lymphocytes with tumor-recognizing capabilities in vivo. This paradigm contrasts with those currently used to generate T cells with defined anti-cancer specificities, which involve isolation of the lymphocytes from the patient and genetically modifying them in the laboratory with tumor antigen-specific receptors using retroviral or lentiviral vectors; the programmed cells are then expanded and infused back into the patient where they can recognize and destroy cancer cells. This ex vivo production of modified cells requires the production of a new lymphocyte cohort for each patient, a laborious process that can only be accomplished at elaborate cell-production facilities available at just a few cancer centers worldwide.

The disclosed methods provide a more practical and widespread approach, allowing use of an "off-the-shelf" solution that can quickly modify lymphocytes to recognize and destroy tumors while they are circulating in a subject, thus avoiding the complications of laboratory modification of extracted cells. In comparison to in vitro methods that modify and expand T cells for each patient, the compositions and methods disclosed herein can produce targeting effects within a subject's circulatory system in only days.

The disclosed methods provide the first implementation of nanocarriers for the genetic engineering of immune cells to selectively target cells associated with markers for various therapeutic objectives. For example, and in relation to cancer cells as an unwanted cell type, previous nanotechnology-based clinical research has focused on particles that selectively accumulate chemotherapeutics, siRNA, or imaging agents at tumor sites while minimizing off-target toxicities. The methods described herein are different: instead of introducing therapeutics into tumor tissue, the disclosed methods introduce genes encoding tumor-recognizing receptors into circulating lymphocytes, which in turn bind and destroy tumor cells. This strategy has the advantage that, unlike agent-loaded nanoparticles (which are quickly cleared by phagocytes), the modified lymphocytes can persist and proliferate in the subject for a long-term effect. Thus, in relation to cancer treatments specifically, the current disclosure provides a new, more effective therapy. The disclosure shifts the focus from broad-impact chemotherapy or radiotherapy (which have many negative side-effects) to tumor-specific immunotherapeutics (which do not harm healthy tissue). Nanoparticle gene therapy will provide clinicians with the ability to instantly treat diagnosed patients with an off-the shelf composition that can be widely distributed at low cost, and is amenable to changes in dose and specificity as the treatment evolves.

In the context of cancers, therapeutically effective amounts can decrease the number of tumor cells, decrease the number of metastases, decrease tumor volume, increase life expectancy, induce apoptosis of cancer cells, induce cancer cell death, induce chemo- or radiosensitivity in cancer cells, inhibit angiogenesis near cancer cells, inhibit cancer cell proliferation, inhibit tumor growth, prevent metastasis, prolong a subject's life, reduce cancer-associated pain, reduce the number of metastases, and/or reduce relapse or re-occurrence of the cancer following treatment.

While the methods disclosed herein are advantageously practiced in vivo, additional embodiments may also be practiced ex vivo. For example, the methods can include obtaining lymphocytes from a subject. Lymphocytes can, e.g., be obtained from a subject using any procedure generally known in the art. For example, blood can be obtained from a subject and lymphocytes can be isolated. The isolated lymphocytes can then be combined with nanocarriers (or a composition comprising nanocarriers) including a polynucleotide having a sequence that encodes a targeting agent. The nanocarriers can be internalized by the lymphocytes such that the lymphocytes then incorporate the polynucleotide and express the targeting agent. The modified lymphocytes expressing the targeting agent can be administered to the subject such that, after the administering, the lymphocytes bind to the targeted markers on cells associated with the disease, thereby treating the disease. It will be appreciated, for example, that the modifying of the lymphocytes can be fully accomplished ex vivo prior to administration, and/or nanocarriers can be internalized and the lymphocytes can be administered to the subject while modifying is being carried out leading to expression of the targeting agents.

Exemplary Embodiments—Set 1

1. A synthetic nanocarrier comprising (i) a lipid-coated porous nanoparticle (ii) a lymphocyte-directing agent extending from the surface of the lipid-coated porous nanoparticle; and (iii) a polynucleotide encoding a chimeric antigen receptor (CAR) targeting agent within the pores of the lipid-coated porous nanoparticle nanoparticle.
2. A synthetic nanocarrier of embodiment 1 further comprising an endosomal release agent extending from the surface of the lipid-coated porous nanoparticle and (ii) a nuclear localization signal (NLS) within the pores of the lipid-coated porous nanoparticle.
3. A synthetic nanocarrier of embodiments 1 or 2 wherein the CAR is P28z.
4. A synthetic nanocarrier of any one of embodiments 1, 2 or 3 wherein the lipid coating is a liposome, a lipid bilayer or a polymeric micelle.
5. A synthetic nanocarrier of any one of embodiments 1-4 wherein the synthetic nanocarriers comprise liposomes, polymeric particles, metallic particles, polymeric micelles, polyethyleneimine (PEI)/DNA complexes, or a combination thereof.
6. A synthetic nanocarrier of any one of embodiments 1-5 wherein the lipid coating encapsulates the lipid-coated porous nanoparticle.
7. A synthetic nanocarrier of any one of embodiments 1-6 wherein the lymphocyte-directing agent selectively binds to lymphocytes in vivo.
8. A synthetic nanocarrier of any one of embodiments 1-7 wherein the lymphocyte-directing agent comprises a binding domain selected from a lymphocyte receptor ligand, lymphocyte receptor antibody, lymphocyte receptor peptide aptamer, lymphocyte receptor nucleic acid aptamer, lymphocyte receptor spiegelmer, or a combination thereof.
9. A synthetic nanocarrier of any one of embodiments 1-8 wherein the lymphocyte-directing agent selectively binds T cells, NK cells, monocytes, macrophages, B cells, hematopoietic stem cells, or a combination thereof.
10. A synthetic nanocarrier of any one of embodiments 1-9 wherein the lymphocyte-directing agent selectively binds T-cell receptor motifs; T-cell α chains; T-cell β chains; T-cell γ chains; T-cell δ chains; CCR7; CD3; CD4; CDS; CD7; CD8; CD11b; CD11c; CD16; CD19; CD20; CD21; CD22; CD25; CD28; CD34; CD35; CD40; CD45RA; CD45RO; CD52; CD56; CD62L; CD68; CD80; CD95; CD117; CD127; CD133; CD137 (4-1BB); CD163; F4/80; IL-4Rα; Sca-1; CTLA-4; GITR; GARP; LAP; granzyme B; LFA-1; or transferrin receptor.
11. A synthetic nanocarrier of any one of embodiments 1-9 wherein the lymphocyte-directing agent selectively binds CCR7; CD3; CD4; CDS; CD8; CD16; CD19; CD20; CD21; CD22; CD25; CD28; CD35; CD40; CD45RA; CD45RO; CD52; CD62L; CD80; CD95; CD127; or CD137.
12. A synthetic nanocarrier of any one of embodiments 1-9 wherein the lymphocyte-directing agent comprises a binding domain selected from a T-cell α chain antibody; T-cell β chain antibody; T-cell γ chain antibody; T-cell δ chain antibody; CCR7 antibody; CD3 antibody; CD4 antibody; CD5 antibody; CD7 antibody; CD8 antibody; CD11b antibody; CD11c antibody; CD16 antibody; CD19 antibody; CD20 antibody; CD21 antibody; CD22 antibody; CD25 antibody; CD28 antibody; CD34 antibody; CD35 antibody; CD40 antibody; CD45RA antibody; CD45RO antibody; CD52 antibody; CD56 antibody; CD62L antibody; CD68 antibody; CD80 antibody; CD95 antibody; CD117 antibody; CD127 antibody; CD133 antibody; CD137 (4-1BB) antibody; CD163 antibody; F4/80 antibody; IL-4Rα antibody; Sca-1 antibody; CTLA-4 antibody; GITR antibody GARP antibody; LAP antibody; granzyme B antibody; LFA-1 antibody; or transferrin receptor antibody.

13. A synthetic nanocarrier of embodiment 12 wherein the binding domain consists of or consists essentially of an scFv fragment of a T-cell α chain antibody; T-cell β chain antibody; T-cell γ chain antibody; T-cell δ chain antibody; CCR7 antibody; CD3 antibody; CD4 antibody; CD5 antibody; CD7 antibody; CD8 antibody; CD11b antibody; CD11c antibody; CD16 antibody; CD19 antibody; CD20 antibody; CD21 antibody; CD22 antibody; CD25 antibody; CD28 antibody; CD34 antibody; CD35 antibody; CD40 antibody; CD45RA antibody; CD45RO antibody; CD52 antibody; CD56 antibody; CD62L antibody; CD68 antibody; CD80 antibody; CD95 antibody; CD117 antibody; CD127 antibody; CD133 antibody; CD137 (4-1BB) antibody; CD163 antibody; F4/80 antibody; IL-4Rα antibody; Sca-1 antibody; CTLA-4 antibody; GITR antibody GARP antibody; LAP antibody; granzyme B antibody; LFA-1 antibody; or transferrin receptor antibody.

14. A synthetic nanocarrier of embodiment 12 wherein the binding domain consists of consists of or consists essentially of the scFv fragment (SEQ ID NO. 1) of the PSMA-specific chimeric antigen receptor (CAR), P28z.

15. A synthetic nanocarrier of any of embodiments 1-14 wherein the polynucleotide is a plasmid, a minicircle plasmid, or an mRNA molecule.

16. A synthetic nanocarrier of any of embodiments 1-15 wherein the CAR targeting agent comprises a binding domain for a marker associated with an unwanted cell type.

17. A synthetic nanocarrier of embodiment 16 wherein the unwanted cell type is a cancer cell.

18. A synthetic nanocarrier of embodiment 16 wherein the marker is a cancer antigen.

19. A synthetic nanocarrier of embodiment 16 wherein the marker is a cancer antigen selected from A33; BAGE; Bcl-2; β-catenin; CA125; CA19-9; CD5; CD19; CD20; CD21; CD22; CD33; CD37; CD45; CD123; CEA; c-Met; CS-1; cyclin B1; DAGE; EBNA; EGFR; ephrinB2; estrogen receptor; FAP; ferritin; folate-binding protein; GAGE; G250; GD-2; GM2; gp75, gp100 (Pmel 17); HER-2/neu; HPV E6; HPV E7; Ki-67; LRP; mesothelin, p53, PRAME; progesterone receptor; PSA; PSMA; MAGE; MART; mesothelin; MUC; MUM-1-B; myc; NYESO-1; ras; RORI; survivin; tenascin; TSTA tyrosinase; VEGF; or WT1.

20. A synthetic nanocarrier of embodiment 16 wherein the marker is PSMA.

21. A synthetic nanocarrier of any of embodiments 1-20 wherein the CAR targeting agent is a surface antigen receptor or a receptor for an intracellular antigen presented by a Major Histocompatibility Complex antigen-presenting pathway.

22. A synthetic nanocarrier of any one of embodiments 2-21 wherein the endosomal release agent is selected from any one of SEQ ID NOs. 29-50 or combinations thereof.

23. A synthetic nanocarrier of any one of embodiments 2-22 wherein the NLS is selected from any one of SEQ ID NOs. 51-93 or combinations thereof.

24. A synthetic nanocarrier of any one of embodiments 1-23 comprising a S/MAR element, a PiggyBac transposase-containing plasmid, a Sleeping Beauty transposase-containing plasmid; a homo sapiens transposon-derived Buster1 transposase-like protein gene; a human endogenous retrovirus H protease/integrase-derived ORF1; a homo sapiens Cas-Br-M (murine) ecotropic retroviral transforming sequence; a homo sapiens endogenous retroviral sequence K; a homo sapiens endogenous retroviral family W sequence; a homo sapiens LINE-1 type transposase domain; or a homo sapiens pogo transposable element.

25. A composition comprising a synthetic nanocarrier of any one of embodiments 1-24.

26. A method of treating a subject having a condition associated with a cell type comprising: administering a therapeutically effective amount of a synthetic nanocarrier of any one of embodiments 1-24 to the subject thereby treating the subject.

27. A method of treating a subject having a condition associated with a cell type comprising: administering a therapeutically effective amount of a composition of embodiment 25 to the subject thereby treating the subject.

28. A method of embodiments 26 or 27 wherein the unwanted cell type is an unwanted cancer cell.

29. A method of embodiment 28 wherein the unwanted cancer cell is selected from an adrenal cancer cell, a bladder cancer cell, a blood cancer cell, a bone cancer cell, a brain cancer cell, a breast cancer cell, a carcinoma cell, a cervical cancer cell, a colon cancer cell, a colorectal cancer cell, a corpus uterine cancer cell, an ear, nose and throat (ENT) cancer cell, an endometrial cancer cell, an esophageal cancer cell, a gastrointestinal cancer cell, a head and neck cancer cell, a Hodgkin's disease cell, an intestinal cancer cell, a kidney cancer cell, a larynx cancer cell, a leukemia cell, a liver cancer cell, a lymph node cancer cell, a lymphoma cell, a lung cancer cell, a melanoma cell, a mesothelioma cell, a myeloma cell, a nasopharynx cancer cell, a neuroblastoma cell, a non-Hodgkin's lymphoma cell, an oral cancer cell, an ovarian cancer cell, a pancreatic cancer cell, a penile cancer cell, a pharynx cancer cell, a prostate cancer cell, a rectal cancer cell, a sarcoma cell, a seminoma cell, a skin cancer cell, a stomach cancer cell, a teratoma cell, a testicular cancer cell, a thyroid cancer cell, a uterine cancer cell, a vaginal cancer cell, or a vascular tumor cell.

30. A method of any one of embodiments 26-29 wherein the administering results in expression of the polynucleotide selectively by lymphocytes within 10 days; within 9 days; within 8 days; within 7 days; within 6 days; within 5 days; within 4 days; or within 3 days of administration.

31. A method for treating a disease associated with an antigen, the method comprising: administering to a subject in need thereof, a composition comprising a therapeutically effective amount of nanocarriers including a polynucleotide having a sequence that encodes a receptor for the antigen, thereby treating the disease.

32. A method of embodiment 31 wherein after the administering the nanocarriers are selectively incorporated into lymphocytes in the subject such that the lymphocytes express the receptor and subsequently bind to the antigen on cells associated with the disease thereby killing the cells.

33. A method for treating a disease associated with an antigen, the method comprising:
obtaining lymphocytes from a subject in need thereof;
combining the lymphocytes with a composition comprising nanocarriers including a polynucleotide having a sequence that encodes a receptor for the antigen, wherein the nanocarriers are selectively incorporated into the lymphocytes such that the lymphocytes express the receptor; and
administering the lymphocytes expressing the receptor to the subject, thereby treating the disease.

34. A method of embodiment 33 wherein after the administering, the lymphocytes bind to the antigen on cells associated with the disease thereby killing the cells.

35. A method of selectively transfecting lymphocytes in vivo, the method comprising:
contacting lymphocytes with nanocarriers comprising a polynucleotide having a sequence that encodes a receptor for an antigen associated with a disease, wherein the nanocarriers are selectively incorporated into the lymphocyte to release the polynucleotide such that the lymphocyte expresses the receptor, thereby transfecting the lymphocyte.

36. A method of embodiment 35 wherein the antigen comprises a tumor antigen.

37. A method of embodiment 35 wherein the antigen comprises a viral antigen.

38. A method of any one of embodiments 35-37 wherein the lymphocytes comprise T-cells, NK cells, macrophages, monocytes, B cells, hematopoietic stem cells, or a combination thereof.

39. A method of embodiment 38 wherein the lymphocytes comprise T-cells.

40. A method of any one of embodiments 35-39 wherein the disease is a cancer.

41. A method of embodiment 40 wherein the cancer comprises a leukemia, a lymphoma, a carcinoma, a sarcoma, or a melanoma.

42. A method of embodiment 40 wherein the disease is prostate cancer.

Exemplary Embodiments—Set 2

1. A synthetic nanocarrier comprising (i) a lymphocyte-directing agent; and (ii) a polynucleotide encoding a targeting agent.

2. A synthetic nanocarrier of embodiment 1 further comprising a nanoparticle.

3. A synthetic nanocarrier of embodiments 1 or 2 further comprising a coating.

4. A synthetic nanocarrier of embodiment 2 or 3 wherein the nanoparticle is a porous nanoparticle.

5. A synthetic nanocarrier of embodiment 3 or 4 wherein the coating is a liposome, a lipid bilayer, or a polymeric micelle.

6. A synthetic nanocarrier of any one of embodiments 1-5 wherein the synthetic nanocarrier comprises liposomes, polymeric particles, metallic particles, polymeric micelles, polyethyleneimine (PEI)/DNA complexes, or a combination thereof.

7. A synthetic nanocarrier of embodiments 3 or 5 wherein the coating encapsulates the nanoparticle.

8. A synthetic nanocarrier of any one of embodiments 1-7 wherein the polynucleotide is on the surface of the nanocarrier, incorporated in the nanocarrier, encapsulated in the nanocarrier, or a combination thereof.

9. A synthetic nanocarrier of any one of embodiments 3-8 wherein the lymphocyte-directing agent extends from the outer surface of the coating.

10. A synthetic nanocarrier of any one of embodiments 4-9 wherein the polynucleotide is within the pores of the porous nanoparticle.

11. A synthetic nanocarrier of any one of embodiments 1-10 wherein the lymphocyte-directing agent selectively binds to lymphocytes in vivo.

12. A synthetic nanocarrier of any one of embodiments 1-11 wherein the lymphocyte-directing agent comprises a binding domain selected from a lymphocyte receptor ligand, lymphocyte receptor antibody, lymphocyte receptor peptide aptamer, lymphocyte receptor nucleic acid aptamer, lymphocyte receptor spiegelmer, or a combination thereof.

13. A synthetic nanocarrier of any one of embodiments 1-12 wherein the lymphocyte-v agent selectively binds T cells, NK cells, monocytes, macrophages, B cells, hematopoietic stem cells, or a combination thereof.

14. A synthetic nanocarrier of any one of embodiments 1-13 wherein the lymphocyte-directing agent selectively binds T-cell receptor motifs; T-cell α chains; T-cell β chains; T-cell γ chains; T-cell Δ chains; CCR7; CD3; CD4; CD5; CD7; CD8; CD11b; CD11c; CD16; CD19; CD20; CD21; CD22; CD25; CD28; CD34; CD35; CD40; CD45RA; CD45RO; CD52; CD56; CD62L; CD68;CD80; CD95; CD117; CD127; CD133; CD137 (4-1BB); CD163; F4/80; IL-4Rα; Sca-1; CTLA-4; GITR; GARP; LAP; granzyme B; LFA-1; or transferrin receptor.

15. A synthetic nanocarrier of any one of embodiments 1-13 wherein the lymphocyte-directing agent selectively binds CCR7; CD3; CD4; CD5; CD8; CD16; CD19; CD20; CD21; CD22; CD25; CD28; CD35; CD40; CD45RA; CD45RO; CD52; CD62L; CD80; CD95; CD127; or CD137.

16. A synthetic nanocarrier of any one of embodiments 1-13 wherein the lymphocyte-directing agent comprises a binding domain selected from a T-cell α chain antibody; T-cell β chain antibody; T-cell γ chain antibody; T-cell Δ chain antibody; CCR7 antibody; CD3 antibody; CD4 antibody; CD5 antibody; CD7 antibody; CD8 antibody; CD11b antibody; CD11c antibody; CD16 antibody; CD19 antibody; CD20 antibody; CD21 antibody; CD22 antibody; CD25 antibody; CD28 antibody; CD34 antibody; CD35 antibody; CD40 antibody; CD45RA antibody; CD45RO antibody; CD52 antibody; CD56 antibody; CD62L antibody; CD68 antibody; CD80 antibody; CD95 antibody; CD117 antibody; CD127 antibody; CD133 antibody; CD137 (4-1BB) antibody; CD163 antibody; F4/80 antibody; IL-4Rα antibody; Sca-1 antibody; CTLA-4 antibody; GITR antibody GARP antibody; LAP antibody; granzyme B antibody; LFA-1 antibody; or transferrin receptor antibody.

17. A synthetic nanocarrier of embodiment 16 wherein the binding domain consists of or consists essentially of an scFv fragment of a T-cell α chain antibody; T-cell β chain antibody; T-cell γ chain antibody; T-cell δ chain antibody; CCR7 antibody; CD3 antibody; CD4 antibody; CD5 antibody; CD7 antibody; CD8 antibody; CD11b antibody; CD11c antibody; CD16 antibody; CD19 antibody; CD20 antibody; CD21 antibody; CD22 antibody; CD25 antibody; CD28 antibody; CD34 antibody; CD35 antibody; CD40 antibody; CD45RA antibody; CD45RO antibody; CD52 antibody; CD56 antibody; CD62L antibody; CD68 antibody; CD80 antibody; CD95 antibody; CD117 antibody; CD127 antibody; CD133 antibody; CD137

(4-1BB) antibody; CD163 antibody; F4/80 antibody; IL-4Rα antibody; Sca-1 antibody; CTLA-4 antibody; GITR antibody GARP antibody; LAP antibody; granzyme B antibody; LFA-1 antibody; or transferrin receptor antibody.

18. A synthetic nanocarrier of embodiment 17 wherein the binding domain consists of consists of or consists essentially of the scFv fragment (SEQ ID NO. 1) of the PSMA-specific chimeric antigen receptor (CAR), P28z.

19. A synthetic nanocarrier of any of embodiments 1-18 wherein the polynucleotide is a plasmid, a minicircle plasmid, or an mRNA molecule.

20. A synthetic nanocarrier of any of embodiments 1-19 wherein the targeting agent comprises a binding domain for a marker associated with an unwanted cell type.

21. A synthetic nanocarrier of embodiment 20 wherein the unwanted cell type is a cancer cell, a virally infected cell, a bacterial cell, or a fungal cell.

22. A synthetic nanocarrier of embodiment 20 wherein the marker is a cancer antigen, a viral antigen, a bacterial antigen, or a fungal antigen.

23. A synthetic nanocarrier of embodiment 20 wherein the marker is a cancer antigen selected from A33; BAGE; Bcl-2; β-catenin; CA125; CA19-9; CD5; CD19; CD20; CD21; CD22; CD33; CD37; CD45; CD123; CEA; c-Met; CS-1; cyclin B1; DAGE; EBNA; EGFR; ephrinB2; estrogen receptor; FAP; ferritin; folate-binding protein; GAGE; G250; GD-2; GM2; gp75, gp100 (Pmel 17); HER-2/neu; HPV E6; HPV E7; Ki-67; LRP; mesothelin, p53, PRAME; progesterone receptor; PSA; PSMA; MAGE; MART; mesothelin; MUC; MUM-1-B; myc; NYESO-1; ras; RORI; survivin; tenascin; TSTA tyrosinase; VEGF; or WT1.

24. A synthetic nanocarrier of embodiment 23 wherein the marker is PSMA.

25. A synthetic nanocarrier of embodiment 20 wherein the marker is a viral antigen selected from envelope glycoprotein B; CMV pp65; EBV; EBNAI; EBV; P18; EBV P23; S protein of hepatitis B; of M protein of hepatitis B; L proteins of hepatitis B; pre-S antigen of hepatitis B virus; HBCAG DELTA; HBV; HBE; hepatitis C viral RNA; HCV NS3; HCV NS4; herpes simplex immediate early proteins; glycoprotein D; HIV gp32; HIV gp41; HIV gp120; HIV gp160; HIV P17/24; HIV P24; HIV P55 GAG; HIV P66 POL; HIV TAT; HIV GP36; Nef protein; hemagglutinin; neuraminidase; Japanese encephalitis protein E; Japanese encephalitis protein M-E; Japanese encephalitis protein M-E-NS1; Japanese encephalitis protein NS1; Japanese encephalitis protein NS1-NS2A; Japanese encephalitis protein 80% E; measles virus fusion protein; rabies glycoprotein; rabies nucleoprotein; RSV fusion protein; M2 protein; VP7sc; rubella protein E1; rubella protein E2; gpI; gpII; Nef (66-97); Nef (116-145); Gag p17 (17-35); Gag p17-p24 (253-284); and Pol 325-355 (RT 158-188).

26. A synthetic nanocarrier of embodiment 20 wherein the marker is a bacterial antigen selected from anthrax protective antigen; lipopolysaccharide; capsular polysaccharide; diptheria toxin; mycolic acid; heat shock protein 65 (HSP65); the 30 kDa major secreted protein; antigen 85A; hemagglutinin; pertactin; FIM2; FIM3; adenylate cyclase; pneumolysin; pneumococcal capsular polysaccharide; rompA; M proteins; tetanus toxin; lipoteichoic acid; and clumping factor A (ClfA).

27. A synthetic nanocarrier of embodiment 20 wherein the marker is a fungal antigen selected from spherule antigens; capsular polysaccharides; heat shock protein 60; gp63; lipophosphoglycan; merozoite surface antigens; sporozoite surface antigens; circumsporozoite antigens; gametocyte/gamete surface antigens; blood-stage antigen pf 155/RESA; glutathione-S-transferase; paramyosin; trichophytin; SAG-1; p30; trypanosoma cruzi 75-77 kDa antigen; and trypanosoma cruzi 56 kDa antigen.

28. A synthetic nanocarrier of any of embodiments 1-19 wherein the targeting agent comprises a binding domain for a marker associated with a wanted cell type.

29. A synthetic nanocarrier of embodiment 28 wherein the wanted cell type is a cell associated with an autoimmune disorder, a cell associated with an allergy, or a bacterial cell.

30. A synthetic nanocarrier of embodiment 28 wherein the marker is an autoimmune antigen, an allergic antigen, or a bacterial antigen.

31. A synthetic nanocarrier of embodiment 30 wherein the marker is an autoimmune antigen selected from glutamic acid decarboxylase 65 (GAD 65); native DNA; myelin basic protein; myelin proteolipid protein; acetylcholine receptor components; thyroglobulin; and thyroid stimulating hormone (TSH) receptor.

32. A synthetic nanocarrier of embodiment 30 wherein the marker is an allergic antigen selected from Japanese cedar pollen antigens; ragweed pollen antigens; rye grass pollen antigens; dust mite antigens; feline antigens; and canine antigens.

33. A synthetic nanocarrier of any of embodiments 1-32 wherein the targeting agent is a surface antigen receptor or a receptor for an intracellular antigen presented by a Major Histocompatibility Complex antigen-presenting pathway.

34. A synthetic nanocarrier of any of embodiments 1-33 wherein the targeting agent is an antigen receptor or a chimeric antigen receptor.

35. A synthetic nanocarrier of embodiment 34 wherein the targeting agent is a P28z chimeric antigen receptor.

36. A synthetic nanocarrier of embodiment 34 wherein the marker is CD19.

37. A synthetic nanocarrier of embodiment 36 wherein the targeting agent is monoclonal antibody FMC63.

38. A synthetic nanocarrier of embodiment 36 wherein the targeting agent is a human or humanized scFv comprising a variable light chain comprising a CDRL1 sequence of RASQDISKYLN (SEQ ID NO. 14), CDRL2 sequence of SRLHSGV (SEQ ID NO. 15), and a CDRL3 sequence of GNTLPYTFG (SEQ ID NO. 16).

39. A synthetic nanocarrier of embodiment 36 wherein the targeting agent is a human or humanized scFv comprising a variable heavy chain comprising CDRHI sequence of DYGVS (SEQ ID NO. 17), CDRH2 sequence of VTWGSETTYYNSALKS (SEQ ID NO. 18), and a CDRH3 sequence of YAMDYWG (SEQ ID NO. 19).

40. A synthetic nanocarrier of embodiment 34 wherein the marker is RORI.

41. A synthetic nanocarrier of embodiment 40 wherein the targeting agent is a human or humanized scFv comprising a variable light chain comprising a CDRL1 sequence of ASGFDFSAYYM (SEQ ID NO. 22), CDRL2 sequence of TIYPSSG (SEQ ID NO. 23), and a CDRL3 sequence of ADRATYFCA (SEQ ID NO. 24).

42. A synthetic nanocarrier of embodiment 40 wherein the targeting agent is a human or humanized scFv comprising a variable heavy chain comprising CDRH1 sequence of DTIDWY (SEQ ID NO. 25), CDRH2 sequence of VQSDGSYTKRPGVPDR (SEQ ID NO. 26), and a CDRH3 sequence of YIGGYVFG (SEQ ID NO. 27).

43. A synthetic nanocarrier of any one of embodiments 1-42 wherein the synthetic nanocarrier further comprises an endosomal release agent.

44. A synthetic nanocarrier of any one of embodiments 43 wherein the endosomal release agent extends from the outer surface of the coating.

45. A synthetic nanocarrier of embodiments 43 or 44 wherein the endosomal release agent is selected from any one of SEQ ID NOs. 29-50 or combinations thereof.

46. A synthetic nanocarrier of any of embodiments 1-45 wherein the polynucleotide is associated with a nuclear localization signal (NLS).

47. A synthetic nanocarrier of any one of embodiments 46 wherein the NLS is within a pore of the porous nanoparticle.

48. A synthetic nanocarrier of embodiments 46 or 47 wherein the NLS is selected from any one of SEQ ID NOs. 51-93 or combinations thereof.

49. A synthetic nanocarrier of any one of embodiments 1-48 comprising a S/MAR element, a PiggyBac transposase-containing plasmid, a Sleeping Beauty transposase-containing plasmid; a homo sapiens transposon-derived Buster1 transposase-like protein gene; a human endogenous retrovirus H protease/integrase-derived ORF1; a homo sapiens Cas-Br-M (murine) ecotropic retroviral transforming sequence; a homo sapiens endogenous retroviral sequence K; a homo sapiens endogenous retroviral family W sequence; a homo sapiens LINE-1 type transposase domain; or a homo sapiens pogo transposable element.

50. A composition comprising a synthetic nanocarrier of any one of embodiments 1-49.

51. A method of treating a subject having a condition associated with a cell type comprising: administering a therapeutically effective amount of a synthetic nanocarrier of any one of embodiments 1-49 to the subject thereby treating the subject.

52. A method of treating a subject having a condition associated with a cell type comprising: administering a therapeutically effective amount of a composition of embodiment 50 to the subject thereby treating the subject.

53. A method of embodiments 51 or 52 wherein the cell type is an unwanted cell type selected from a cancer cell, a virally infected cell, a bacterial cell, or a fungal cell.

54. A method of embodiment 53 wherein the unwanted cell type is a cancer cell selected from an adrenal cancer cell, a bladder cancer cell, a blood cancer cell, a bone cancer cell, a brain cancer cell, a breast cancer cell, a carcinoma cell, a cervical cancer cell, a colon cancer cell, a colorectal cancer cell, a corpus uterine cancer cell, an ear, nose and throat (ENT) cancer cell, an endometrial cancer cell, an esophageal cancer cell, a gastrointestinal cancer cell, a head and neck cancer cell, a Hodgkin's disease cell, an intestinal cancer cell, a kidney cancer cell, a larynx cancer cell, a leukemia cell, a liver cancer cell, a lymph node cancer cell, a lymphoma cell, a lung cancer cell, a melanoma cell, a mesothelioma cell, a myeloma cell, a nasopharynx cancer cell, a neuroblastoma cell, a non-Hodgkin's lymphoma cell, an oral cancer cell, an ovarian cancer cell, a pancreatic cancer cell, a penile cancer cell, a pharynx cancer cell, a prostate cancer cell, a rectal cancer cell, a sarcoma cell, a seminoma cell, a skin cancer cell, a stomach cancer cell, a teratoma cell, a testicular cancer cell, a thyroid cancer cell, a uterine cancer cell, a vaginal cancer cell, or a vascular tumor cell.

55. A method of any one of embodiments 51-54 wherein the administering results in expression of the polynucleotide selectively by lymphocytes within 10 days; within 9 days; within 8 days; within 7 days; within 6 days; within 5 days; within 4 days; or within 3 days of administration.

56. A method for treating a disease associated with an antigen, the method comprising: administering to a subject in need thereof, a composition comprising a therapeutically effective amount of nanocarriers including a polynucleotide having a sequence that encodes a receptor for the antigen, thereby treating the disease.

57. A method of embodiment 56 wherein after the administering the nanocarriers are selectively incorporated into lymphocytes in the subject such that the lymphocytes express the receptor and subsequently bind to the antigen on cells associated with the disease thereby killing the cells.

58. A method for treating a disease associated with an antigen, the method comprising:
obtaining lymphocytes from a subject in need thereof;
combining the lymphocytes with a composition comprising nanocarriers including a polynucleotide having a sequence that encodes a receptor for the antigen, wherein the nanocarriers are selectively incorporated into the lymphocytes such that the lymphocytes express the receptor; and
administering the lymphocytes expressing the receptor to the subject, thereby treating the disease.

59. A method of embodiment 58 wherein after the administering, the lymphocytes bind to the antigen on cells associated with the disease thereby killing the cells.

60. A method of selectively transfecting lymphocytes in vivo, the method comprising: contacting lymphocytes with nanocarriers comprising a polynucleotide having a sequence that encodes a receptor for an antigen, wherein the nanocarriers are selectively incorporated into the lymphocyte to release the polynucleotide such that the lymphocyte expresses the receptor, thereby transfecting the lymphocyte.

61. A method of any one of embodiments 51-60 wherein the antigen comprises a tumor antigen.

62. A method of any one of embodiments 51-60 wherein the antigen comprises a viral antigen.

63. A method of any one of embodiments 51-62 wherein the lymphocytes comprise T-cells, NK cells, macrophages, monocytes, B cells, hematopoietic stem cells, or a combination thereof.

64. A method of embodiment 63 wherein the lymphocytes comprise T-cells.

65. A method of any one of embodiment 56 wherein the disease is a cancer.

66. A method of embodiment 65 wherein the cancer comprises a leukemia, a lymphoma, a carcinoma, a sarcoma, or a melanoma.
67. A method of embodiment 65 wherein the disease is prostate cancer.
68. A method of embodiment 62 wherein the antigen is expressed by virus-infected cells associated with the disease.

Each of the exemplary embodiments in Set 1 and Set 2 also includes an embodiment wherein the lymphocyte-directing agent can be removed. These embodiments are especially useful when the selected cell types are monocytes/macrophages and broad non-specific uptake of the nanocarriers can be expected.

EXAMPLES

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Example 1

Figure 3:
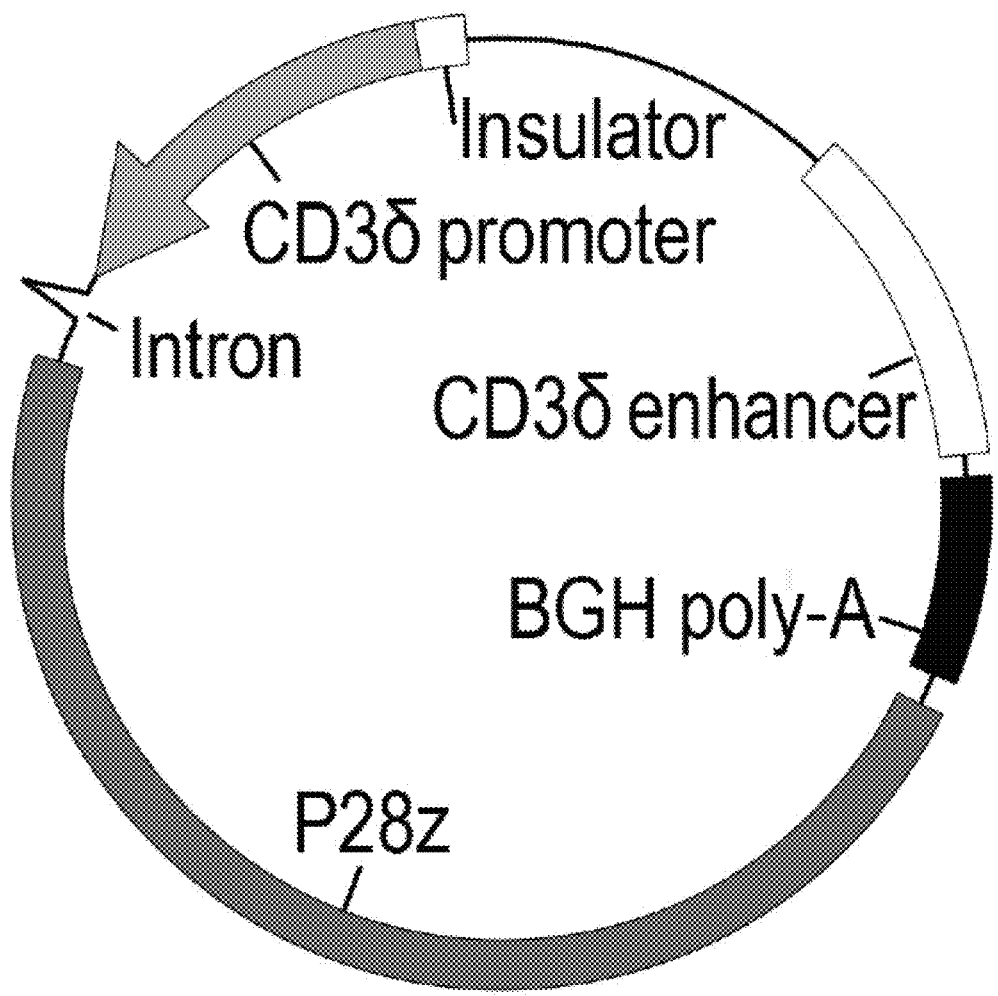
FIG. 3: Schematic representation of minicircle DNA construct used in studies described herein. Structure of the P28z minicircle. The prostate-specific membrane antigen (PSMA)-targeting chimeric antigen receptor P28z is expressed under the control of the T-cell-specific CD3-delta promoter.
Figure 4A:
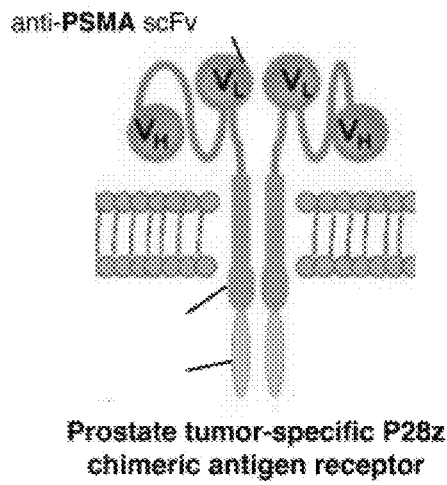
FIGS. 4A-4E: Redirecting T-cell specificity toward prostate tumor via nanoparticle-mediated gene transfer.

This example demonstrates that synthetic nanoparticles containing TCR genes can be used to generate functional tumor- or virus-specific T-cells. Lipid nanoparticles (FIG. 2A) were loaded with a minicircle gene (FIG. 3) encoding the chimeric antigen receptor P28z. P28z is a fusion receptor composed of a single-chain antibody (scFv) specific for the extracellular domain of PSMA (J591) combined with CD28 and CD3ζ cytoplasmic signaling domains (FIG. 4A; SEQ ID NO. 94). In this Example, chimeric antigen receptors (CARs) are fusion receptors including an antigen-binding domain, a transmembrane domain and an intracellular signaling domain resulting in T-cell activation after antigen binding. The P28z CAR directs T-cells toward the prostate-specific membrane antigen (PSMA), which is highly expressed on prostate cancer cells. Therefore, the introduction of the P28z gene into T-cells renders them capable of recognizing and lysing prostate tumor. The P28z gene was cloned under the control of the T-cell specific promoter CD3 delta into a minicircle plasmid. Minicircles can include episomal DNA vectors that are produced as circular expression cassettes devoid of any bacterial plasmid DNA backbone. Their smaller molecular size can enable more efficient transfections and offers sustained expression over a period of weeks as compared to standard plasmid vectors that only work for a few days.

The minicircle plasmid DNA was entrapped into nanocarriers. DOPC, DOPE, cholesterol, and 18:1 PEG 2000 PE lipids were first mixed in a 55:5:30:10 mass ratio, dried under a stream of nitrogen, and placed in a vacuum oven overnight to remove residual chloroform. The lipid film was then dissolved in tert-butanol and mixed 1:1 (v/v) with a P28z minicircle plasmid solution (diluted in 10 mM Tris-HCl (pH 7.4) with 0.85% (w/v) NaCl and 0.25 M sucrose) such that the final DOPC:DNA ratio was 10:1 (w/w). The mixture was vortexed and passed through a 100 nm filter at least 10 times using a Mini-Extruder set (Avanti Polar Lipids, Inc.; Alabaster, Ala., USA).

To target nanocarriers to T-cells, anti-mouse CD8 antibodies were coupled to the surface of the lipid envelope. Anti-CD8 antibodies (10 mg/ml) were mildly reduced with a 25× molar excess of DTT for 20 min at 25° C. in the presence of 10 mM EDTA in PBS to expose free hinge region thiols. To remove DTT, antibodies were passed through a desalting column. The heterobifunctional cross-linker $SM(PEG)_{24}$ was used to anchor antibodies to the surface of DNA-loaded liposomes (Amine groups are present in the head groups of PE lipids, free thiol groups on antibodies were created by DTT, $SM(PEG)_{24}$ cross-links between amines and thiol groups). Liposomes were first incubated with a tenfold molar excess of $SM(PEG)_{24}$ for 2 h at room temperature and centrifuged to remove unreacted cross-linker. Activated liposomes were then incubated with a fivefold molar excess of reduced anti-CD8 antibody for 2 h at room temperature. Unbound antibody was removed using a centrifugal filtration device (10 kDa MWCO). The final liposome used for subsequent experiments were ~100 nm in diameter.

Figure 4B:
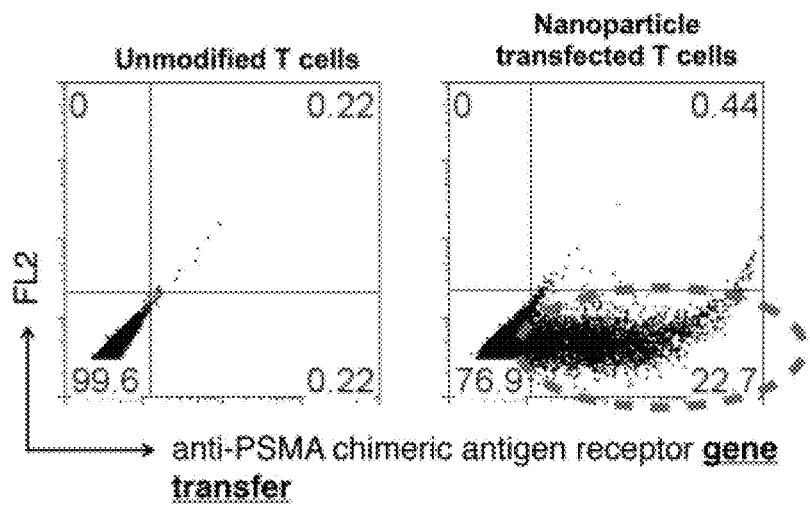
Figure 4C:
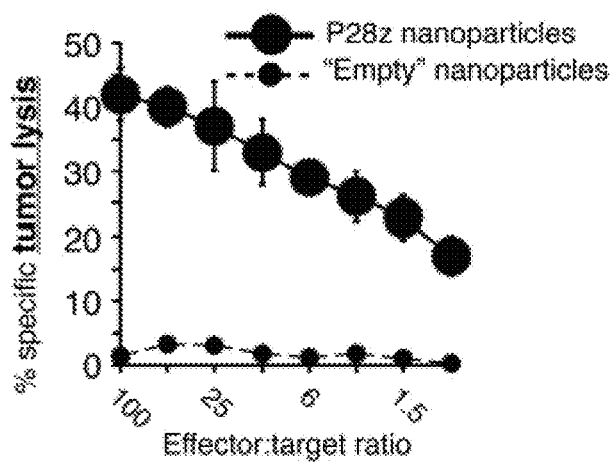
Figure 4D:
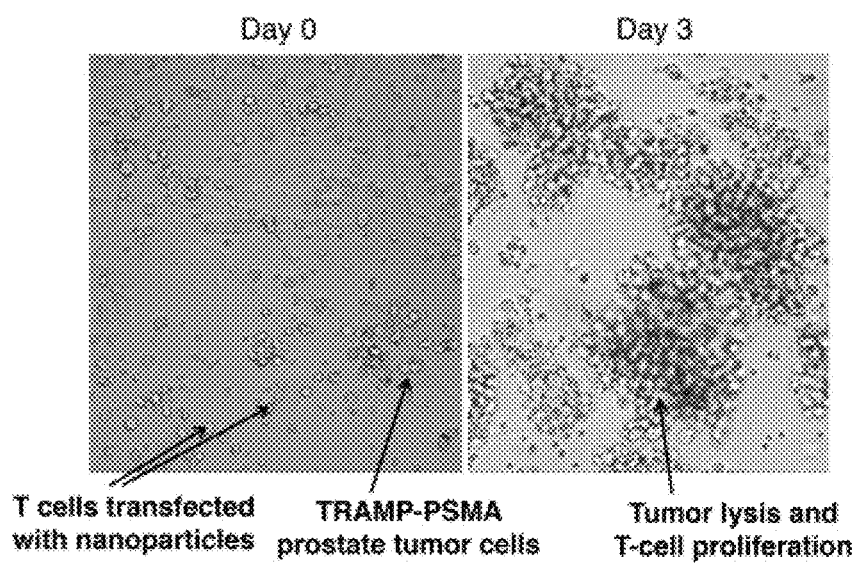

P28z gene transfer into T-cells using targeted DNA nanocarriers renders them capable of lysing prostate tumor. The transfection efficiency of liposome-mediated gene transfer into primary T-cells was assessed. $60 \times 10^6$ mouse effector $CD8^+$ T-cells $mL^{-1}$ were resuspended in RPMI medium and an equal volume of lipid nanoparticles (loaded with P28z minicircle DNA) were added with a 100 particles/T-cell ratio. Cells were incubated at 37° C. for 30 min with gentle agitation every 10 min and unbound particles were removed by a PBS wash. Two days later, the percentage of T-cells expressing the P28z CAR was determined by flow cytometry. Thirty hours after transfection ~23% of the cells expressed the P28z receptor on their surface (FIG. 4B). High P28z expression persisted for three days in vitro before declining toward undetectable expression by eight days (data not shown). Nanoparticle-transfected T cells were functional, selectively lysing PSMA-expressing TRAMP prostate tumor cells (FIG. 4C, FIG. 4D).

Example 2

Figure 4E:
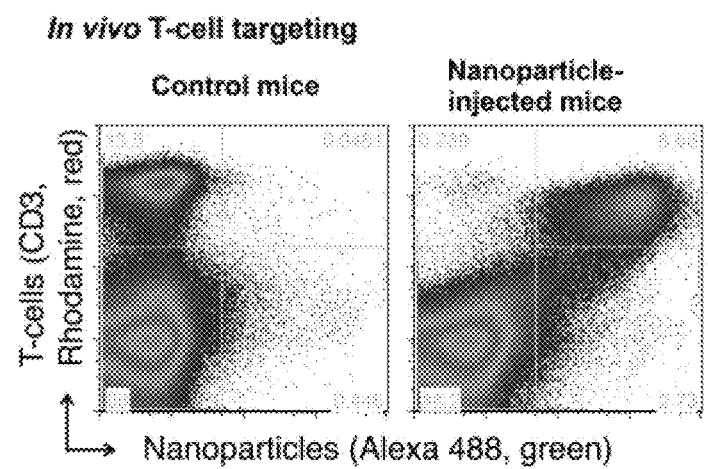

CD3-targeted protocell nanoparticles selectively bind circulating T cells in mice. A goal of the current disclosure is to selectively and quickly edit lymphocyte specificity in vivo to target unwanted cells. To examine how selectively protocells bind circulating host T cells, mice were systemically injected with $1 \times 10^{11}$ fluorescently tagged nanoparticles. After 6 hours peripheral blood was collected by retro-orbital puncture and the percentage of fluorescent T cells was quantified by flow cytometry. CD3-targeted protocells labeled the majority of T cells in the blood, with relatively low binding to off-target cells (FIG. 4E, left panel). Confocal imaging of sorted T cells showed that nanoparticles are rapidly internalized from the cell surface into the cytoplasm as a result of receptor-induced endocytosis (FIG. 4E, right panel).

Example 3

Figure 5A:
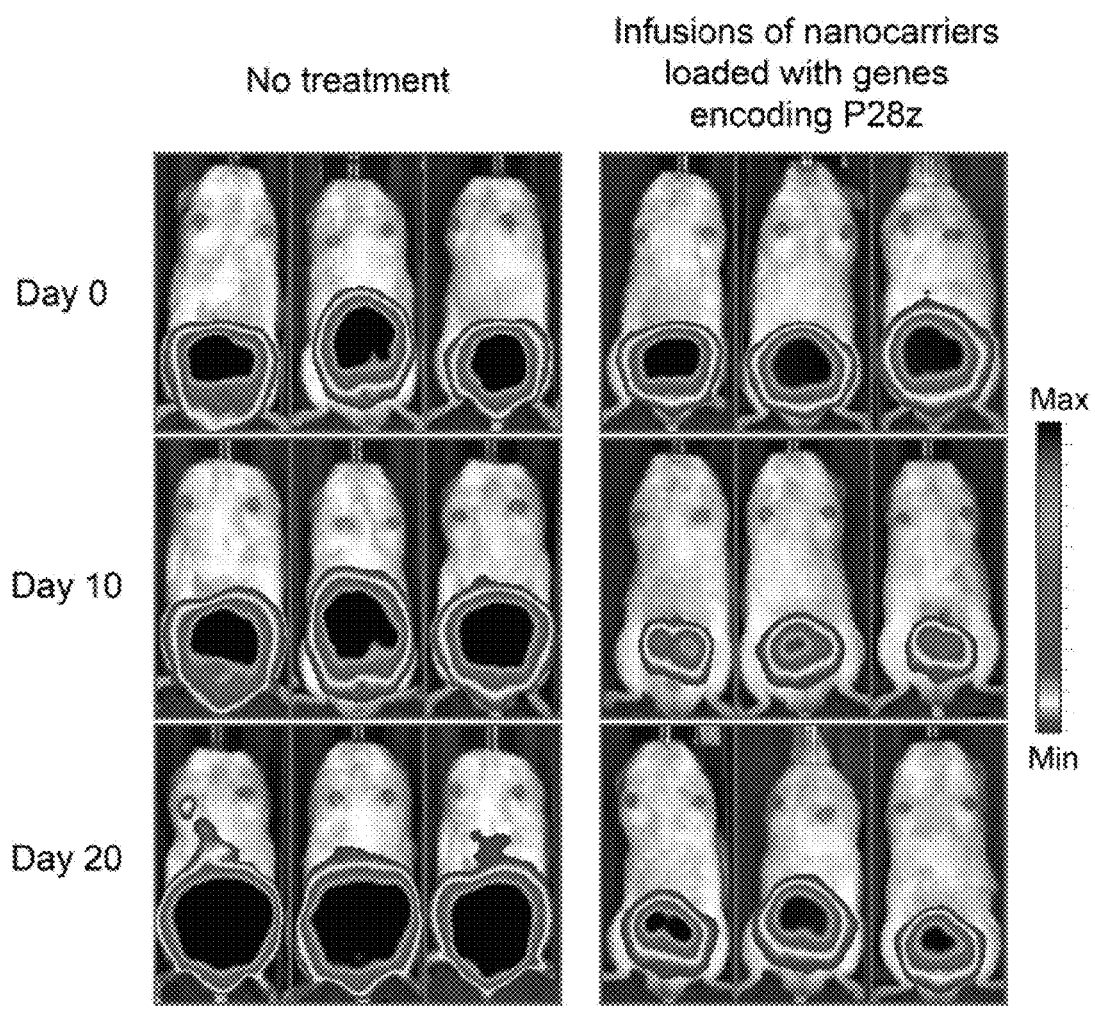
FIGS. 5A and 5B: Repeated injections of nanocarriers loaded DNA encoding the P28z chimeric antigen receptor brings about T-cell mediated regression of prostate tumor in mice. Luciferase tagged TRAMP-PSMA prostate tumor cells were transplanted into the dorsal lobe of the prostate gland of C57BL/6 mice. Two weeks later (Day 0), mice were treated with five high-dose bolus injections of $1 \times 10^{12}$ CD3-targeting nanoparticles carrying P28z-encoding transgenes (Day 0, Day 2, Day 4, Day 6, and Day 8). Control mice received no nanoparticles.
Figure 5B:
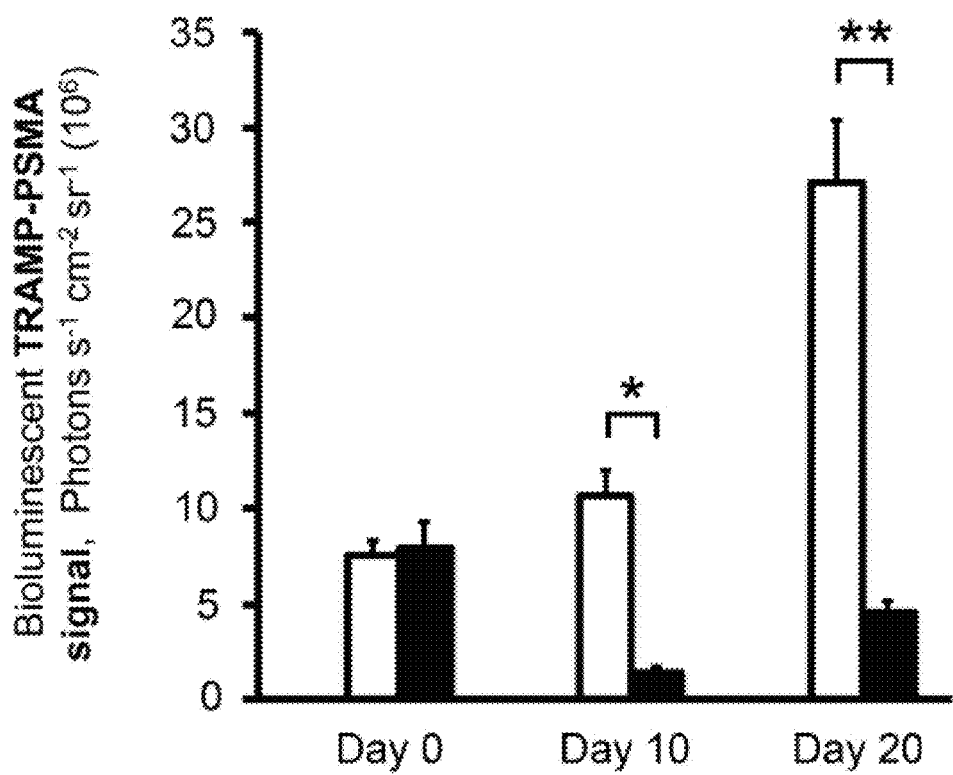

Generating an orthotopic bioluminescent mouse model for analyzing treatment of metastatic prostate cancer. Male TRAMP transgenic mice spontaneously develop orthotopic prostate tumors following puberty. However, unlike human prostate adenocarcinoma, TRAMP tumors do not express significant amounts of PSMA, a target in experiments using the P28z CAR. Furthermore, longitudinal studies to measure the prostate cancer volume in TRAMP animals rely on expensive and time-consuming magnetic resonance imaging (MRI) techniques, which preclude analysis of large cohorts of mice. To overcome these issues, a cell line from a primary TRAMP tumor was established and the PSMA gene was introduced through retroviral transduction. To serially monitor tumor burden by bioluminescence imaging, tumor cells were also genetically tagged with Firefly luciferase (FLuc). Following orthotopic transplantation into the dorsal lobe of the prostate gland of C57BL/6 mice, TRAMP-PSMA-FLuc tumor cells reproducibly developed into lesions within three weeks, with all animals displaying progressive metastatic tumor spread to regional (pelvic, paraaortic) lymph nodes (FIGS. 5A and 5B).

Example 4

The data shown in FIGS. 2A and 2B and FIGS. 4A-4E establish the ability to generate nanoparticles that efficiently program T cells with genes encoding receptors specific for prostate tumor. While this strategy rapidly generates tumor-reactive T cells, expression of transgenes is transient because transferred plasm ids are diluted out every time the lymphocyte divides. The current example evaluates persistent receptor gene expression in actively dividing T cells caused by inserting into the plasmid either: 1) a scaffold/matrix attachment region (S/MAR) sequence (which can undergo episomal self-replication), or 2) a transposable piggyBac element (which integrates the transgene into the genome). Stable and dependable transgene expression in dividing T cells will allow nanoparticle-transfected lymphocytes to serially kill unwanted cell types providing long-lived immunity against such cells.

Figure 6A:
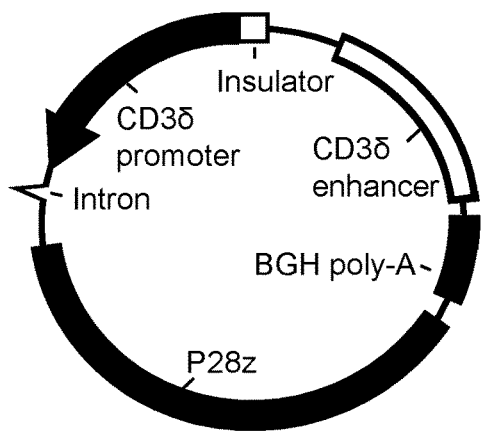
FIGS. 6A-6C: Schematic representation of minicircle DNA constructs.
Figure 6B:
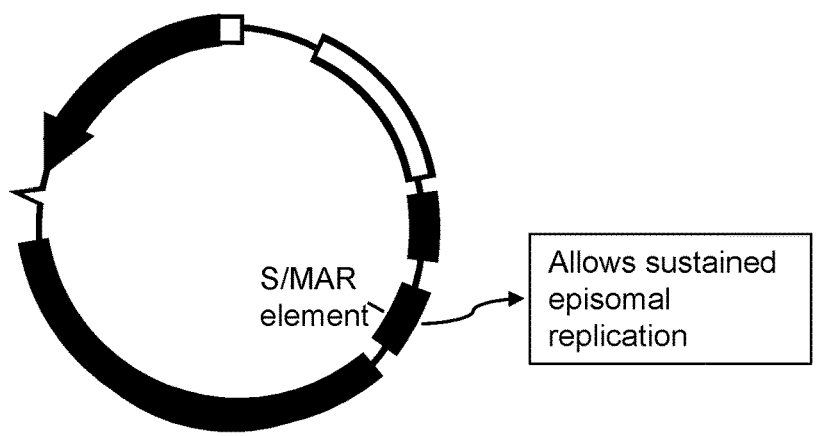
Figure 6C:
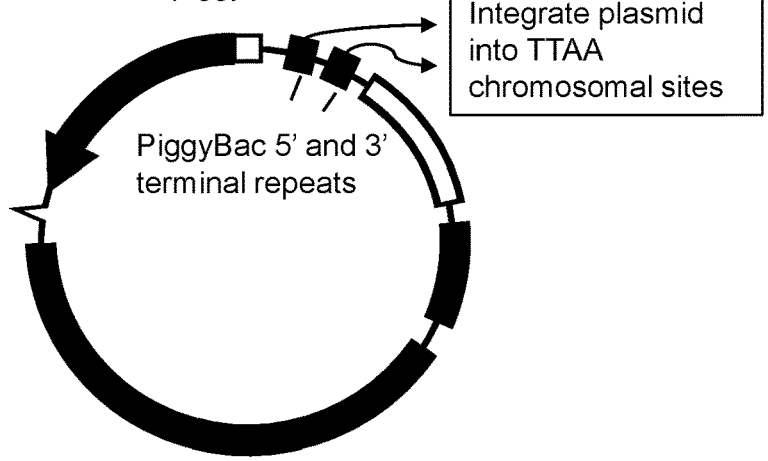

In this Example, a S/MAR sequence (provided by Dr. Lipps, University Witten/Herdecke) or piggyBac inverted terminal repeats (provided by Dr. Craig, Johns Hopkins University) will be cloned into minicircle plasmids that encode the P28z receptor, as illustrated in FIGS. 6A-6C. Protocell nanoparticles loaded with equivalent amounts of P28z, P28z-S/MAR, or P28z-piggyBac minicircle DNA will be incubated with mouse CD8+ T lymphocytes at a cell:particle ratio of 1:10. Following nanoparticle transfection, T cells will be expanded with plate-bound anti-CD3/anti-CD28 antibodies. Flow cytometry will be used to assess P28z receptor expression levels and persistence in proliferating T cells every 24 hours during a two week culture period.

To investigate the extent to which S/MAR sequences or piggyBac transposable elements prevent nanoparticle-transferred plasmids from being lost by dilution in dividing T cells, the actual number of P28z gene copies per T cell over time will be quantified. To this end, genomic and low-molecular weight (episomal) DNA will be isolated from transfected T cells at each time point during the two week period. Vector copy numbers will be measured by multiplex quantitative PCR (qPCR) with a set of primers and probes specific to the P28z minicircle plasmid. A set of primers specific to the gene encoding mouse albumin will be included as an internal two-copy control.

To discriminate between episomal (extrachromosomal) versus genome-integrated P28z transgenes, Southern blot analysis will be performed by digesting isolated DNA with NotI. This restriction site is present only once in the P28z minicircle episome; it yields a 2.8-kb band for the extrachromosomal episome but yields fragments of various lengths for plasm ids integrated into the genome.

The described studies will show that S/MAR-based episomes and piggyBac transposons are two highly efficient tools to modify cells to achieve stable gene expression. Incorporating S/MAR sequences or piggyBac transposable elements into nanocarrier-delivered plasmids will also maintain high-level P28z gene expression in T cells over weeks as a result of episomal self-replication or somatic integration, respectively. Because plasmids containing S/MAR elements do not integrate into the host genome, P28z gene expression is independent of chromosomal position effects and therefore not subject to epigenetic silencing and cis-acting sequences.

Example 6

This Example determines that systemic injections of DNA nanocarriers can program sufficient quantities of T cells to target and eliminate disseminated prostate cancer. The tests will be conducted using nanoparticles loaded with minicircle DNA encoding the P28z CAR (described above), to generate PSMA-specific lymphocytes. The results of the studies will be positive following testing of the following questions: (1) how many peripheral T cells are genetically modified to express P28z following a single intravenous dose of CD3-targeting nanoparticles loaded with genes encoding the receptor?; (2) do the injected nanoparticles selectively edit the antigen-specificity of peripheral T cells without affecting off-target cells? And (3) what nanoparticle dosage is required to bring about T cell-mediated regression of metastatic prostate tumors in mice?

Example 6(1)

What percentage of peripheral T cells are modified by nanoparticle gene therapy? The goal of this study is to edit the antigen specificity of at least 10% of peripheral T cells within five days following a single bolus injection of nanocarriers. For comparison, some of the strongest vaccine vectors reported in the literature induce frequencies of self/tumor antigen-specific T cells of 1-4% following repeated immunizations over weeks. Mice will be systemically injected with $1 \times 10^9$, $1 \times 10^{10}$, or $1 \times 10^{11}$ nanocarriers loaded with minicircle DNA encoding P28z, or with GFP as a control. After collecting peripheral blood by retro-orbital puncture every four days over a 12-day period, the percentage of P28z+ T cells will be quantified by flow cytometry using fluorescent recombinant PSMA protein as the reporter, as performed in previous gene transfer studies (see, e.g., FIG. 4B).

Example 6(2)

Does nanoparticle gene therapy edit the antigen specificity of peripheral T cells without affecting off-target cells? To confirm in vivo studies, showing that CD3-targeting protocells efficiently bind to host T cells after intravenous injection (FIG. 4E), how selectively nanoparticles introduce tumor-targeting receptor genes into circulating T cells will also be determined. To this end, P28z expression by other leukocyte subsets will be evaluated, using the samples obtained in Example 6(1). The other cell types will be identified using the following reporters: anti-CD8 and anti-CD4 (T-cell markers), anti-B220 (B-cell marker), anti-NK1.1 (NK-cell marker), anti-CD115, anti-F4/80 and anti-CD11b (monocyte markers), anti-Ly6G and anti-CD11b (neutrophil markers), and anti-Gr-1 antibody (granulocyte marker).

Example 6(3)

What nanoparticle dosage is required to bring about T cell-mediated regression of metastatic prostate tumors in mice? To develop a reproducibly effective treatment for metastatic prostate cancer, the therapeutically optimal frequency and dosage of nanocarrier injections must be determined. A test system will be created by injecting luciferase-expressing TRAMP-PSMA tumor cells into the prostate of C57BL/6 mice and allowing them to develop for three weeks before performing the tests (see, e.g., FIGS. 5A and 5B).

The mice will be systemically injected with CD3-targeting nanocarriers carrying P28z-encoding transgenes, according to four administration protocols: single high-dose bolus injection ($1 \times 10^{10}$ nanoparticles, i.v.); high-frequency high-dose injections ($1 \times 10^{10}$ nanoparticles, i.v. every 3 days for 30 days); single low-dose injection ($1 \times 10^{9}$ nanoparticles, i.v.); or high-frequency low-dose injections ($1 \times 10^{9}$ nanoparticles, i.v. every 3 days for 30 days). To compare the therapeutic efficacy of nanoparticle infusions with conventional adoptive T-cell therapy, one additional group of mice will be treated with a single dose of 10 million T cells transduced ex vivo with P28z-encoding retroviral vectors. Differences in TRAMP-PSMA tumor progression will be measured between treatment and control groups using bioluminescence imaging. To correlate tumor regression with the concentration of nanoparticle-programmed T cells in the peripheral circulation, the percentage of P28z$^+$ T cells in whole blood will be quantified by flow cytometry every 6 days.

The results will show that circulating T cells can be selectively programmed to target prostate tumors without genetically modifying other cells. This specificity can be achieved by coating the nanoparticles with CD3-recognizing antibodies, and by expressing the P28z transgene under the control of the T cell-specific CD3 delta promoter. If flow cytometry shows that more than 20% of P28z-expressing cells in the peripheral blood are not the targeted T cells, the density of anti-CD3 antibodies on the surface of nanocarriers will be increased to improve T cell targeting. If the CD3 delta promoter is too weak to mediate sufficient levels of receptor gene expression in vivo, the murine stem cell leukemia virus (MSCV) promoter can be used to express the P28z CAR in T cells. The MSCV promoter exhibits strong activity in hematopoietic cells and stem cells.

Example 7

Example 7 determines that nanocarriers can alternatively modify host T cells with prostate tumor-specific T-cell receptor (TCR) genes that target different antigens.

Gene transfer of DNA encoding CARs can only target T cells to antigens located on the surface of tumor cells, so the many tumor antigens that are intracellular are inaccessible to these receptors. However, after degradation in the proteasome these intracellular proteins are presented by major histocompatibility complex (MHC) molecules where they can be recognized by specific T cell receptors (TCRs).

A murine receptor (3D TCR) that has a high affinity for the intracellular oncoprotein Wilms tumor 1 (WT1) has been successfully engineered by a team of immunologists led by P. Greenberg at the Fred Hutchinson Cancer Research Center. WT1 was ranked first in a list of 75 cancer antigens in a recent National Cancer Institute prioritization project. It is strongly expressed in high-grade prostate tumor where it promotes the formation of metastases, but is absent in non-neoplastic or benign prostatic hyperplasia tissues. In line with these studies, high WT1 gene expression was detected in the TRAMP prostate tumor cells used herein. WT1 is detected at only very low levels in other normal tissues, particularly hematopoietic stem cells and kidney podocytes. T cells have been shown to be capable of selectively recognizing transformed cells expressing high levels without toxicity to normal tissues. In Example 7 it will be shown that systemic injections of protocells loaded with genes encoding affinity-matured WT1-specific TCRs can impart specificity for WT1 to host T cells and lead to elimination of prostate cancer.

To determine how efficiently nanocarriers transfect T cells with WT1-TCR genes in vivo, mice will be injected with $1 \times 10^{10}$ nanoparticles carrying 3D TCR genes. Control nanoparticles will be loaded with GFP-expressing plasmids. Peripheral blood collected by retro-orbital puncture every four days over a 12-day period will be used to quantify WT1-TCR$^+$ T cells and other leukocyte subsets by flow cytometry using a fluorescent conjugate of the WT1-derived RMFPNAPYL epitope tetramer as the reporter.

To investigate whether nanoparticle injections can cause regression of metastatic prostate cancer in mice, luciferase-expressing TRAMP tumors will be implanted into the prostate of C57BL/6 mice. Three weeks later, animals will be treated with: a single high-dose bolus injection ($1 \times 10^{10}$ nanoparticles i.v.); high-frequency high-dose injections ($1 \times 10^{10}$ nanoparticles i.v. every 3 days for 30 days); a single low-dose injection ($1 \times 10^{9}$ nanoparticles, i.v.); or high-frequency low-dose injections ($1 \times 10^{9}$ nanoparticles, i.v. every 3 days for 30 days). To determine the therapeutic advantage of nanoparticle infusions over conventional adoptive T-cell therapy, one additional group of mice will be injected with 10 million T cells, which were ex vivo transduced with 3D TCR genes using retroviral vectors. Differences in TRAMP prostate tumor regression between treatment and control groups will be measured using bioluminescence imaging.

The strength of T cell responses in antitumor immunity can be decisively dependent on the quality of the TCRs involved. Due to thymic selection, the affinities of natural TCRs that target oncogenic self-proteins like WT1 are generally much lower than those of typical virus-targeting TCRs. However, the ability of a naturally occurring TCR to recognize antigens like WT1 can be markedly enhanced by in vitro affinity maturation. Based on these data, if genes for an affinity-optimized, WT1-specific TCR are introduced into circulating T cells using the disclosed nanoparticle gene therapy approach, T cells will effectively recognize and kill prostate cancer cells. 3D TCRs are fully functional in CD4$^+$ and CD8$^+$ T cells, and CD4$^+$ T cells can directly mediate tumor destruction and/or provide cytokine help for CD8$^+$ T cells; however, tumor-specific CD4$^+$ regulatory T cells abrogate CD8 T cell-mediated tumor rejection. If CD3-targeted nanoparticles generate undesirable WT1-specific CD4$^+$ regulatory T cells, nanoparticles can be targeted to CD8$^+$ T cells only. These studies will demonstrate that nanoparticles can deliver rationally engineered TCR genes into host T-cells and enable them to recognize intracellular tumor-associated antigen.

Example 8

Modifying host lymphocytes with HIV-specific TCR genes to control HIV infection. HIV-infected humanized NOD/shi-scid/γc null (NOG) mice with nanoparticles carrying HIV-gag protein-specific TCR transgenes, or with control plasmids expressing green fluorescent protein will be studied. Differences in HIV viral titers between treatment groups will be determined and administration of the nanoparticles will show a beneficial result.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, $2^{nd}$ Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

Sequence information provided by public database can be used to identify nucleic acid sequences encoding peptides disclosed herein and vice versa. Variants of the sequences disclosed and referenced herein are also included.

Variants of peptides can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of the protein and nucleic acid sequences disclosed or referenced herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to he protein and nucleic acid sequences disclosed or referenced herein.

"% sequence identity" refers to a relationship between two or more sequences, as determined by comparing the sequences. In the art, "identity" also means the degree of sequence relatedness between proteins or nucleic acid sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the ability of a nanocarrier to reduce the number of an unwanted cell type and/or to protect a wanted cell type in vivo.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of selectively transfecting T cells with a polynucleotide in vivo through receptor-mediated endocytosis wherein the transfecting results in in vivo cancer cell killing, the method comprising:
Infusing a nanocarrier that is less than about 100 nm in diameter into the bloodstream of a subject wherein the nanocarrier comprises
(i) a negatively-charged coating surrounding a porous core comprising mesoporous silica or a polymer matrix;
(ii) a lymphocyte-directing agent extending from the surface of the nanocarrier wherein the lymphocyte-directing agent comprises a binding domain consisting of an ScFv fragment of a CD3 antibody or an ScFv fragment of a CD8 antibody that induces receptor-mediated endocytosis upon binding to CD3 or CD8 on the surface of a T cell; and
(iii) a polynucleotide encoding a chimeric antigen receptor (CAR) targeting agent within the pores of the core wherein upon introduction into a transfected T cell, the polynucleotide results in transcription and resulting translation of the CAR targeting agent;
thereby selectively transfecting T cells with the polynucleotide in vivo through receptor-mediated endocytosis wherein the transfecting results in in vivo cancer cell killing.

2. The method of claim 1 wherein the binding domain consists of SEQ ID NO. 1.

3. The method of claim 1 wherein the polynucleotide is a plasmid, or a minicircle plasmid under the control of a T-cell specific CD3-delta promoter.

4. The method of claim 1 wherein the CAR is P28z.

5. The method of claim 1 wherein the nanocarrier further comprises an endosomal release agent extending from the surface of the nanocarrier and (ii) a nuclear localization signal (NLS) within the pores of the core.

6. The method of claim 5 wherein the endosomal release agent is selected from any one of SEQ ID NOs. 29-50.

7. The method of claim 5 wherein the NLS is selected from any one of SEQ ID NOS. 51-93.

8. The method of claim 1 wherein the nanocarrier further comprises a S/MAR element or transposase-containing plasmid.

9. The method of claim 1 wherein the CAR targeting agent binds a cancer antigen selected from CD19, CD20, HER-2/neu, mesothelin, PSA, PSMA, RORI, or WT1.

10. The method of claim 1 wherein the negatively charged coating comprises dioleoylphosphatidylcholine (DOPC) and cholesterol.

11. The method of claim 10 wherein the negatively charged coating further comprises dioleoylphosphatidylethanolamine (DOPE).

12. The method of claim 1 wherein the lymphocyte-directing agent is linked to the negatively charged coating through polyethylene glycol (PEG).

13. The method of claim 1 wherein the porous core comprises pores with a pore size of about 10-20 nm.

14. A method of selectively transfecting T cells with a plasmid or a minicircle plasmid in vivo through receptor-mediated endocytosis wherein the transfecting results in in vivo cancer cell killing, the method comprising:
Infusing a nanocarrier that is less than about 100 nm in diameter into the bloodstream of a subject wherein the nanocarrier comprises
(i) a negatively-charged coating comprising dioleoylphosphatidylcholine (DOPC) and cholesterol surrounding a porous core comprising mesoporous silica or a polymer matrix having a pore size of about 10-20 nm;
(ii) a lymphocyte-directing agent extending from the surface of the nanocarrier wherein the lymphocyte-directing agent is linked to the negatively charged coating through polyethylene glycol (PEG) and comprises a binding domain consisting of an ScFv fragment of a CD3 antibody or an ScFv fragment of a CD8 antibody that induces receptor-mediated endocytosis upon binding to CD3 or CD8 on the surface of a T cell; and
(iii) a plasmid or minicircle plasmid encoding a chimeric antigen receptor (CAR) targeting agent within the pores of the core wherein expression of the plasmid or minicircle plasmid is under the control of a T-cell specific CD3-delta promoter;
thereby selectively transfecting T cells with the plasmid or minicircle plasmid in vivo through receptor-mediated endocytosis wherein the transfecting results in in vivo cancer cell killing.

15. A method of claim 14 wherein the nanocarrier further comprises an endosomal release agent selected from any one of SEQ ID NOs. 29-50 extending from the surface of the nanocarrier and (ii) a nuclear localization signal (NLS) is selected from any one of SEQ ID NOS 51-93 within the pores of the core.

16. The method of claim 14 wherein the CAR targeting agent binds a cancer antigen selected from CD19, CD20, HER-2/neu, mesothelin, PSA, PSMA, RORI, or WT1.

* * * * *

SEQUENCE LISTING

```
<160> NUMBER OF SEQ ID NOS: 94

<210> SEQ ID NO 1
<211> LENGTH: 265
<212> TYPE: PRT
<213> ORGANISM: Artificial Sequence
<220> FEATURE:
<223> OTHER INFORMATION: scFv of the PSMA-specific chimeric antigen
      receptor P28z

<400> SEQUENCE: 1

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Glu Val Gln Leu Gln
            20                  25                  30

Gln Ser Gly Pro Glu Leu Val Lys Pro Gly Thr Ser Val Arg Ile Ser
```

-continued

```
                35                  40                  45
Cys Lys Thr Ser Gly Tyr Thr Phe Thr Glu Tyr Thr Ile His Trp Val
 50                  55                  60
Lys Gln Ser His Gly Lys Ser Leu Glu Trp Ile Gly Asn Ile Asn Pro
 65                  70                  75                  80
Asn Asn Gly Gly Thr Thr Tyr Asn Gln Lys Phe Glu Asp Lys Ala Thr
                 85                  90                  95
Leu Thr Val Asp Lys Ser Ser Thr Ala Tyr Met Glu Leu Arg Ser
                100                 105                 110
Leu Thr Ser Glu Asp Ser Ala Val Tyr Tyr Cys Ala Ala Gly Trp Asn
                115                 120                 125
Phe Asp Tyr Trp Gly Gln Gly Thr Thr Val Thr Val Ser Ser Gly Gly
130                 135                 140
Gly Gly Ser Gly Gly Gly Gly Ser Gly Gly Gly Gly Ser Asp Ile Val
145                 150                 155                 160
Met Thr Gln Ser His Lys Phe Met Ser Thr Ser Val Gly Asp Arg Val
                165                 170                 175
Ser Ile Ile Cys Lys Ala Ser Gln Asp Val Gly Thr Ala Val Asp Trp
                180                 185                 190
Tyr Gln Gln Lys Pro Gly Gln Ser Pro Lys Leu Leu Ile Tyr Trp Ala
                195                 200                 205
Ser Thr Arg His Thr Gly Val Pro Asp Arg Phe Thr Gly Ser Gly Ser
210                 215                 220
Gly Thr Asp Phe Thr Leu Thr Ile Thr Asn Val Gln Ser Glu Asp Leu
225                 230                 235                 240
Ala Asp Tyr Phe Cys Gln Gln Tyr Asn Ser Tyr Pro Leu Thr Phe Gly
                245                 250                 255
Ala Gly Thr Met Leu Asp Leu Lys Arg
                260                 265

<210> SEQ ID NO 2
<211> LENGTH: 750
<212> TYPE: PRT
<213> ORGANISM: Homo sapiens

<400> SEQUENCE: 2

Met Trp Asn Leu Leu His Glu Thr Asp Ser Ala Val Ala Thr Ala Arg
 1                   5                  10                  15
Arg Pro Arg Trp Leu Cys Ala Gly Ala Leu Val Leu Ala Gly Gly Phe
                 20                  25                  30
Phe Leu Leu Gly Phe Leu Phe Gly Trp Phe Ile Lys Ser Ser Asn Glu
                 35                  40                  45
Ala Thr Asn Ile Thr Pro Lys His Asn Met Lys Ala Phe Leu Asp Glu
 50                  55                  60
Leu Lys Ala Glu Asn Ile Lys Lys Phe Leu Tyr Asn Phe Thr Gln Ile
 65                  70                  75                  80
Pro His Leu Ala Gly Thr Glu Gln Asn Phe Gln Leu Ala Lys Gln Ile
                 85                  90                  95
Gln Ser Gln Trp Lys Glu Phe Gly Leu Asp Ser Val Glu Leu Ala His
                100                 105                 110
Tyr Asp Val Leu Leu Ser Tyr Pro Asn Lys Thr His Pro Asn Tyr Ile
                115                 120                 125
Ser Ile Ile Asn Glu Asp Gly Asn Glu Ile Phe Asn Thr Ser Leu Phe
                130                 135                 140
```

```
Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
        180                 185                 190

Lys Ile Asn Cys Ser Gly Lys Ile Val Ile Ala Arg Tyr Gly Lys Val
    195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
```

```
                    565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 3
<211> LENGTH: 123
<212> TYPE: PRT
<213> ORGANISM: Homo sapiens

<400> SEQUENCE: 3

Met Lys Ala Val Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
                20                  25                  30

Glu Asp Cys Leu Gln Val Glu Asn Cys Thr Gln Leu Gly Glu Gln Cys
            35                  40                  45

Trp Thr Ala Arg Ile Arg Ala Val Gly Leu Leu Thr Val Ile Ser Lys
        50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
        115                 120

<210> SEQ ID NO 4
<211> LENGTH: 622
<212> TYPE: PRT
<213> ORGANISM: Homo sapiens

<400> SEQUENCE: 4

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
```

-continued

```
            20                  25                  30
Pro Ser Arg Thr Leu Ala Gly Glu Thr Gly Gln Glu Ala Ala Pro Leu
            35                  40                  45
Asp Gly Val Leu Ala Asn Pro Pro Asn Ile Ser Ser Leu Ser Pro Arg
        50                  55                  60
Gln Leu Leu Gly Phe Pro Cys Ala Glu Val Ser Gly Leu Ser Thr Glu
65                  70                  75                  80
Arg Val Arg Glu Leu Ala Val Ala Leu Ala Gln Lys Asn Val Lys Leu
                85                  90                  95
Ser Thr Glu Gln Leu Arg Cys Leu Ala His Arg Leu Ser Glu Pro Pro
                100                 105                 110
Glu Asp Leu Asp Ala Leu Pro Leu Asp Leu Leu Phe Leu Asn Pro
            115                 120                 125
Asp Ala Phe Ser Gly Pro Gln Ala Cys Thr His Phe Phe Ser Arg Ile
            130                 135                 140
Thr Lys Ala Asn Val Asp Leu Leu Pro Arg Gly Ala Pro Glu Arg Gln
145                 150                 155                 160
Arg Leu Leu Pro Ala Ala Leu Ala Cys Trp Gly Val Arg Gly Ser Leu
                165                 170                 175
Leu Ser Glu Ala Asp Val Arg Ala Leu Gly Gly Leu Ala Cys Asp Leu
                180                 185                 190
Pro Gly Arg Phe Val Ala Glu Ser Ala Glu Val Leu Leu Pro Arg Leu
            195                 200                 205
Val Ser Cys Pro Gly Pro Leu Asp Gln Asp Gln Gln Glu Ala Ala Arg
        210                 215                 220
Ala Ala Leu Gln Gly Gly Pro Pro Tyr Gly Pro Pro Ser Thr Trp
225                 230                 235                 240
Ser Val Ser Thr Met Asp Ala Leu Arg Gly Leu Leu Pro Val Leu Gly
                245                 250                 255
Gln Pro Ile Ile Arg Ser Ile Pro Gln Gly Ile Val Ala Ala Trp Arg
                260                 265                 270
Gln Arg Ser Ser Arg Asp Pro Ser Trp Arg Gln Pro Glu Arg Thr Ile
            275                 280                 285
Leu Arg Pro Arg Phe Arg Arg Glu Val Glu Lys Thr Ala Cys Pro Ser
        290                 295                 300
Gly Lys Lys Ala Arg Glu Ile Asp Glu Ser Leu Ile Phe Tyr Lys Lys
305                 310                 315                 320
Trp Glu Leu Glu Ala Cys Val Asp Ala Ala Leu Leu Ala Thr Gln Met
                325                 330                 335
Asp Arg Val Asn Ala Ile Pro Phe Thr Tyr Glu Gln Leu Asp Val Leu
                340                 345                 350
Lys His Lys Leu Asp Glu Leu Tyr Pro Gln Gly Tyr Pro Glu Ser Val
            355                 360                 365
Ile Gln His Leu Gly Tyr Leu Phe Leu Lys Met Ser Pro Glu Asp Ile
        370                 375                 380
Arg Lys Trp Asn Val Thr Ser Leu Glu Thr Leu Lys Ala Leu Leu Glu
385                 390                 395                 400
Val Asn Lys Gly His Glu Met Ser Pro Gln Val Ala Thr Leu Ile Asp
                405                 410                 415
Arg Phe Val Lys Gly Arg Gly Gln Leu Asp Lys Asp Thr Leu Asp Thr
                420                 425                 430
Leu Thr Ala Phe Tyr Pro Gly Tyr Leu Cys Ser Leu Ser Pro Glu Glu
            435                 440                 445
```

```
Leu Ser Ser Val Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
                500                 505                 510

Gln Gln Asn Val Ser Met Asp Leu Ala Thr Phe Met Lys Leu Arg Thr
            515                 520                 525

Asp Ala Val Leu Pro Leu Thr Val Ala Glu Val Gln Lys Leu Leu Gly
            530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
                580                 585                 590

Val Gln Glu Ala Leu Ser Gly Thr Pro Cys Leu Leu Gly Pro Gly Pro
            595                 600                 605

Val Leu Thr Val Leu Ala Leu Leu Ala Ser Thr Leu Ala
    610                 615                 620

<210> SEQ ID NO 5
<211> LENGTH: 556
<212> TYPE: PRT
<213> ORGANISM: Homo sapiens

<400> SEQUENCE: 5

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
```

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
            325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
            405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 6
<211> LENGTH: 297
<212> TYPE: PRT
<213> ORGANISM: Homo sapiens

<400> SEQUENCE: 6

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 7
<211> LENGTH: 937
<212> TYPE: PRT
<213> ORGANISM: Homo sapiens

<400> SEQUENCE: 7

Met His Arg Pro Arg Arg Arg Gly Thr Arg Pro Pro Leu Leu Ala Leu
1               5                   10                  15

Leu Ala Leu Leu Leu Ala Ala Arg Gly Ala Ala Ala Gln Glu Thr
        20                  25                  30

Glu Leu Ser Val Ser Ala Glu Leu Val Pro Thr Ser Ser Trp Asn Ile
    35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

```
Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
            130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
            210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
            275                 280                 285

Glu Ser Pro Glu Ala Ala Asn Cys Ile Arg Ile Gly Ile Pro Met Ala
            290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
            355                 360                 365

Lys Glu Ala Pro Trp Cys Phe Thr Leu Asp Glu Asn Phe Lys Ser Asp
            370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
            435                 440                 445

Gln Asn Val Glu Met Ser Met Leu Asn Ala Tyr Lys Pro Lys Ser Lys
            450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510
```

```
Asn Pro Gln Gln Trp Thr Glu Phe Gln Gln Glu Ala Ser Leu Met Ala
            515                 520                 525

Glu Leu His His Pro Asn Ile Val Cys Leu Leu Gly Ala Val Thr Gln
        530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
        610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
            690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
            770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
```

-continued

```
            930             935
```

<210> SEQ ID NO 8
<211> LENGTH: 168
<212> TYPE: PRT
<213> ORGANISM: Homo sapiens

<400> SEQUENCE: 8

```
Met Gly His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
        35                  40                  45

Tyr Pro Gly Cys Asn Lys Arg Tyr Phe Lys Leu Ser His Leu Gln Met
    50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165
```

<210> SEQ ID NO 9
<211> LENGTH: 32
<212> TYPE: PRT
<213> ORGANISM: Human immunodeficiency virus type 1

<400> SEQUENCE: 9

```
Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30
```

<210> SEQ ID NO 10
<211> LENGTH: 30
<212> TYPE: PRT
<213> ORGANISM: Human immunodeficiency virus type 1

<400> SEQUENCE: 10

```
His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu
            20                  25                  30
```

<210> SEQ ID NO 11
<211> LENGTH: 19
<212> TYPE: PRT
<213> ORGANISM: Human immunodeficiency virus type 1

<400> SEQUENCE: 11

Glu Lys Ile Arg Leu Arg Pro Gly Gly Lys Lys Tyr Lys Leu Lys
1               5                   10                  15

His Ile Val

<210> SEQ ID NO 12
<211> LENGTH: 32
<212> TYPE: PRT
<213> ORGANISM: Human immunodeficiency virus type 1

<400> SEQUENCE: 12

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

<210> SEQ ID NO 13
<211> LENGTH: 31
<212> TYPE: PRT
<213> ORGANISM: Human immunodeficiency virus type 1

<400> SEQUENCE: 13

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: CDRL1 sequence

<400> SEQUENCE: 14

Arg Ala Ser Gln Asp Ile Ser Lys Tyr Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CDRL2 sequence

<400> SEQUENCE: 15

Ser Arg Leu His Ser Gly Val
1               5

<210> SEQ ID NO 16
<211> LENGTH: 9
<212> TYPE: PRT
<213> ORGANISM: Artificial Sequence
<220> FEATURE:
<223> OTHER INFORMATION: CDRL3 sequence

<400> SEQUENCE: 16

Gly Asn Thr Leu Pro Tyr Thr Phe Gly
1               5

<210> SEQ ID NO 17
<211> LENGTH: 5
<212> TYPE: PRT
<213> ORGANISM: Artificial Sequence
<220> FEATURE:
<223> OTHER INFORMATION: CDRH1 sequence

<400> SEQUENCE: 17

Asp Tyr Gly Val Ser
1               5

<210> SEQ ID NO 18
<211> LENGTH: 16
<212> TYPE: PRT
<213> ORGANISM: Artificial Sequence
<220> FEATURE:
<223> OTHER INFORMATION: CDRH2 sequence

<400> SEQUENCE: 18

Val Thr Trp Gly Ser Glu Thr Thr Tyr Tyr Asn Ser Ala Leu Lys Ser
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: CDRH3 sequence

<400> SEQUENCE: 19

Tyr Ala Met Asp Tyr Trp Gly
1               5

<210> SEQ ID NO 20
<211> LENGTH: 734
<212> TYPE: DNA
<213> ORGANISM: Artificial Sequence
<220> FEATURE:
<223> OTHER INFORMATION: Anti-CD19 scFv (VH-VL) FMC63

<400> SEQUENCE: 20

```
gacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
cggtttagcg gcagcggctc cggcaccgac tacagcctga ccatctccaa cctggaacag     240
gaagatatcg ccacctactt ttgccagcag ggcaacacac tgccctacac ctttggcggc     300
ggaacaaagc tggaaatcac cggcagcacc tccggcagcg gcaagcctgg cagcggcgag     360
ggcagcacca agggcgaggt gaagctgcag gaaagcggcc ctggcctggt ggcccccagc     420
cagagcctga gcgtgacctg caccgtgagc ggcgtgagcc tgcccgacta cggcgtgagc     480
tggatccggc agcccccag gaagggcctg gaatggctgg gcgtgatctg gggcagcgag      540
accacctact acaacagcgc cctgaagagc cggctgacca tcatcaagga caacagcaag     600
agccaggtgt tcctgaagat gaacagcctg cagaccgacg acaccgccat ctactactgc     660
gccaagcact actactacgg cggcagctac gccatggact actggggcca gggcaccagc     720
gtgaccgtga gcag                                                       734
```

<210> SEQ ID NO 21
<211> LENGTH: 245
<212> TYPE: PRT
<213> ORGANISM: Artificial Sequence
<220> FEATURE:
<223> OTHER INFORMATION: Anti-CD19 scFv (VH-VL) FMC63

<400> SEQUENCE: 21

Asp Ile Gln Met Thr Gln Thr Thr Ser Ser Leu Ser Ala Ser Leu Gly

```
  1               5                  10                 15
Asp Arg Val Thr Ile Ser Cys Arg Ala Ser Gln Asp Ile Ser Lys Tyr
            20                  25                 30

Leu Asn Trp Tyr Gln Gln Lys Pro Asp Gly Thr Val Lys Leu Leu Ile
            35                  40                 45

Tyr His Thr Ser Arg Leu His Ser Gly Val Pro Ser Arg Phe Ser Gly
            50                  55                 60

Ser Gly Ser Gly Thr Asp Tyr Ser Leu Thr Ile Ser Asn Leu Glu Gln
 65              70                  75                 80

Glu Asp Ile Ala Thr Tyr Phe Cys Gln Gln Gly Asn Thr Leu Pro Tyr
                 85                  90                 95

Thr Phe Gly Gly Gly Thr Lys Leu Glu Ile Thr Gly Ser Thr Ser Gly
                100                 105                110

Ser Gly Lys Pro Gly Ser Gly Glu Gly Ser Thr Lys Gly Glu Val Lys
            115                 120                125

Leu Gln Glu Ser Gly Pro Gly Leu Val Ala Pro Ser Gln Ser Leu Ser
 130                 135                 140

Val Thr Cys Thr Val Ser Gly Val Ser Leu Pro Asp Tyr Gly Val Ser
145                 150                 155                160

Trp Ile Arg Gln Pro Pro Arg Lys Gly Leu Glu Trp Leu Gly Val Ile
                165                 170                175

Trp Gly Ser Glu Thr Thr Tyr Tyr Asn Ser Ala Leu Lys Ser Arg Leu
                180                 185                190

Thr Ile Ile Lys Asp Asn Ser Lys Ser Gln Val Phe Leu Lys Met Asn
            195                 200                205

Ser Leu Gln Thr Asp Asp Thr Ala Ile Tyr Tyr Cys Ala Lys His Tyr
 210                 215                 220

Tyr Tyr Gly Gly Ser Tyr Ala Met Asp Tyr Trp Gly Gln Gly Thr Ser
225                 230                 235                240

Val Thr Val Ser Ser
                245

<210> SEQ ID NO 22
<211> LENGTH: 11
<212> TYPE: PRT
<213> ORGANISM: Artificial Sequence
<220> FEATURE:
<223> OTHER INFORMATION: CDRL1 sequence

<400> SEQUENCE: 22

Ala Ser Gly Phe Asp Phe Ser Ala Tyr Tyr Met
 1               5                  10

<210> SEQ ID NO 23
<211> LENGTH: 7
<212> TYPE: PRT
<213> ORGANISM: Artificial Sequence
<220> FEATURE:
<223> OTHER INFORMATION: CDRL2 sequence

<400> SEQUENCE: 23

Thr Ile Tyr Pro Ser Ser Gly
 1               5

<210> SEQ ID NO 24
<211> LENGTH: 9
<212> TYPE: PRT
<213> ORGANISM: Artificial Sequence
<220> FEATURE:
```

<223> OTHER INFORMATION: CDRL3 sequence

<400> SEQUENCE: 24

Ala Asp Arg Ala Thr Tyr Phe Cys Ala
1               5

<210> SEQ ID NO 25
<211> LENGTH: 6
<212> TYPE: PRT
<213> ORGANISM: Artificial Sequence
<220> FEATURE:
<223> OTHER INFORMATION: CDRH1 sequence

<400> SEQUENCE: 25

Asp Thr Ile Asp Trp Tyr
1               5

<210> SEQ ID NO 26
<211> LENGTH: 16
<212> TYPE: PRT
<213> ORGANISM: Artificial Sequence
<220> FEATURE:
<223> OTHER INFORMATION: CDRH2 sequence

<400> SEQUENCE: 26

Val Gln Ser Asp Gly Ser Tyr Thr Lys Arg Pro Gly Val Pro Asp Arg
1               5                   10                  15

<210> SEQ ID NO 27
<211> LENGTH: 8
<212> TYPE: PRT
<213> ORGANISM: Artificial Sequence
<220> FEATURE:
<223> OTHER INFORMATION: CDRH3 sequence

<400> SEQUENCE: 27

Tyr Ile Gly Gly Tyr Val Phe Gly
1               5

<210> SEQ ID NO 28
<211> LENGTH: 123
<212> TYPE: DNA
<213> ORGANISM: Artificial Sequence
<220> FEATURE:
<223> OTHER INFORMATION: CD28 effector domain

<400> SEQUENCE: 28
cggagcaagc ggagcagagg cggccacagc gactacatga acatgacccc cagacggcct     60
ggccccaccc ggaagcacta ccagccctac gccccaccca gggactttgc cgcctacaga    120
agc                                                                   123

<210> SEQ ID NO 29
<211> LENGTH: 16
<212> TYPE: PRT
<213> ORGANISM: Homo sapiens

<400> SEQUENCE: 29

Ala Ala Val Ala Leu Leu Pro Ala Val Leu Leu Ala Leu Leu Ala Pro
1               5                   10                  15

<210> SEQ ID NO 30
<211> LENGTH: 11
<212> TYPE: PRT
<213> ORGANISM: Artificial Sequence
<220> FEATURE:

```
<223> OTHER INFORMATION: RFGF analogue

<400> SEQUENCE: 30

Ala Ala Leu Leu Pro Val Leu Leu Ala Ala Pro
1               5                   10

<210> SEQ ID NO 31
<211> LENGTH: 16
<212> TYPE: PRT
<213> ORGANISM: Influenza virus

<400> SEQUENCE: 31

Gly Leu Phe Glu Ala Ile Ala Gly Phe Ile Glu Asn Gly Trp Glu Gly
1               5                   10                  15

<210> SEQ ID NO 32
<211> LENGTH: 11
<212> TYPE: PRT
<213> ORGANISM: Human immunodeficiency virus type 1

<400> SEQUENCE: 32

Tyr Gly Arg Lys Lys Arg Arg Gln Arg Arg Arg
1               5                   10

<210> SEQ ID NO 33
<211> LENGTH: 16
<212> TYPE: PRT
<213> ORGANISM: Duck hepatitis B virus

<400> SEQUENCE: 33

Met Ser Gly Thr Phe Gly Gly Ile Leu Ala Gly Leu Ile Gly Leu Leu
1               5                   10                  15

<210> SEQ ID NO 34
<211> LENGTH: 16
<212> TYPE: PRT
<213> ORGANISM: Woodchuck hepatitis B virus

<400> SEQUENCE: 34

Met Ser Pro Ser Ser Leu Leu Gly Leu Leu Ala Gly Leu Gln Val Val
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Synthetic endosomal release agent

<400> SEQUENCE: 35

Gly Leu Phe Glu Ala Leu Leu Glu Leu Leu Glu Ser Leu Trp Glu Leu
1               5                   10                  15

Leu

<210> SEQ ID NO 36
<211> LENGTH: 16
<212> TYPE: PRT
<213> ORGANISM: Artificial Sequence
<220> FEATURE:
<223> OTHER INFORMATION: Synthetic endosomal release agent

<400> SEQUENCE: 36

Leu Lys Lys Leu Leu Lys Lys Leu Leu Lys Lys Leu Leu Lys Lys Leu
1               5                   10                  15
```

<210> SEQ ID NO 37
<211> LENGTH: 16
<212> TYPE: PRT
<213> ORGANISM: Artificial Sequence
<220> FEATURE:
<223> OTHER INFORMATION: Endosomal release agent

<400> SEQUENCE: 37

Arg Gln Ile Lys Ile Trp Phe Gln Asn Arg Arg Met Lys Trp Lys Lys
1               5                   10                  15

<210> SEQ ID NO 38
<211> LENGTH: 14
<212> TYPE: PRT
<213> ORGANISM: Human immunodeficiency virus type 1

<400> SEQUENCE: 38

Gly Arg Lys Lys Arg Arg Gln Arg Arg Arg Pro Pro Gln Cys
1               5                   10

<210> SEQ ID NO 39
<211> LENGTH: 27
<212> TYPE: PRT
<213> ORGANISM: Human immunodeficiency virus type 1

<400> SEQUENCE: 39

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 40
<211> LENGTH: 18
<212> TYPE: PRT
<213> ORGANISM: Mus musculus

<400> SEQUENCE: 40

Leu Leu Ile Ile Leu Arg Arg Arg Ile Arg Lys Gln Ala His Ala His
1               5                   10                  15

Ser Lys

<210> SEQ ID NO 41
<211> LENGTH: 26
<212> TYPE: PRT
<213> ORGANISM: Artificial Sequence
<220> FEATURE:
<223> OTHER INFORMATION: Transportan

<400> SEQUENCE: 41

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 42
<211> LENGTH: 18
<212> TYPE: PRT
<213> ORGANISM: Artificial Sequence
<220> FEATURE:
<223> OTHER INFORMATION: Amphiphilic model peptide

<400> SEQUENCE: 42

Lys Leu Ala Leu Lys Leu Ala Leu Lys Ala Leu Lys Ala Ala Leu Lys
1               5                   10                  15

Leu Ala

<210> SEQ ID NO 43
<211> LENGTH: 9
<212> TYPE: PRT
<213> ORGANISM: Artificial Sequence
<220> FEATURE:
<223> OTHER INFORMATION: Arg9

<400> SEQUENCE: 43

Arg Arg Arg Arg Arg Arg Arg Arg Arg
1               5

<210> SEQ ID NO 44
<211> LENGTH: 37
<212> TYPE: PRT
<213> ORGANISM: Artificial Sequence
<220> FEATURE:
<223> OTHER INFORMATION: LL-37

<400> SEQUENCE: 44

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 45
<211> LENGTH: 31
<212> TYPE: PRT
<213> ORGANISM: Ascaris suum

<400> SEQUENCE: 45

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 46
<211> LENGTH: 30
<212> TYPE: PRT
<213> ORGANISM: Homo sapiens

<400> SEQUENCE: 46

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 47
<211> LENGTH: 36
<212> TYPE: PRT
<213> ORGANISM: Homo sapiens

<400> SEQUENCE: 47

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

```
<210> SEQ ID NO 48
<211> LENGTH: 12
<212> TYPE: PRT
<213> ORGANISM: Artificial Sequence
<220> FEATURE:
<223> OTHER INFORMATION: Bactenecin

<400> SEQUENCE: 48

Arg Lys Cys Arg Ile Val Val Ile Arg Val Cys Arg
1               5                   10

<210> SEQ ID NO 49
<211> LENGTH: 42
<212> TYPE: PRT
<213> ORGANISM: Sus scrofa
<220> FEATURE:
<221> NAME/KEY: MOD_RES
<222> LOCATION: (42)..(42)
<223> OTHER INFORMATION: AMIDATION

<400> SEQUENCE: 49

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 50
<211> LENGTH: 13
<212> TYPE: PRT
<213> ORGANISM: Bos taurus
<220> FEATURE:
<221> NAME/KEY: MOD_RES
<222> LOCATION: (13)..(13)
<223> OTHER INFORMATION: AMIDATION

<400> SEQUENCE: 50

Ile Leu Pro Trp Lys Trp Pro Trp Trp Pro Trp Arg Arg
1               5                   10

<210> SEQ ID NO 51
<211> LENGTH: 7
<212> TYPE: PRT
<213> ORGANISM: Simian virus 40

<400> SEQUENCE: 51

Pro Lys Lys Lys Arg Lys Val
1               5

<210> SEQ ID NO 52
<211> LENGTH: 16
<212> TYPE: PRT
<213> ORGANISM: Artificial Sequence
<220> FEATURE:
<223> OTHER INFORMATION: bipartite NLS consisting of two basic domains
      separated by a variable number of spacer amino acids and
      exemplified by the Xenopus nucleoplasmin NLS
<220> FEATURE:
<221> NAME/KEY: misc_feature
<222> LOCATION: (3)..(12)
<223> OTHER INFORMATION: Xaa can be any naturally occurring amino acid

<400> SEQUENCE: 52

Lys Arg Xaa Xaa Xaa Xaa Xaa Xaa Xaa Xaa Xaa Xaa Lys Lys Lys Leu
1               5                   10                  15
```

```
<210> SEQ ID NO 53
<211> LENGTH: 7
<212> TYPE: PRT
<213> ORGANISM: Simian virus 40

<400> SEQUENCE: 53

Pro Lys Lys Lys Arg Met Val
1               5

<210> SEQ ID NO 54
<211> LENGTH: 10
<212> TYPE: PRT
<213> ORGANISM: Simian virus 40

<400> SEQUENCE: 54

Pro Lys Lys Lys Arg Lys Val Glu Asp Pro
1               5                   10

<210> SEQ ID NO 55
<211> LENGTH: 8
<212> TYPE: PRT
<213> ORGANISM: Simian virus 40

<400> SEQUENCE: 55

Pro Lys Lys Gly Ser Lys Lys Ala
1               5

<210> SEQ ID NO 56
<211> LENGTH: 7
<212> TYPE: PRT
<213> ORGANISM: Simian virus 40

<400> SEQUENCE: 56

Pro Lys Thr Lys Arg Lys Val
1               5

<210> SEQ ID NO 57
<211> LENGTH: 11
<212> TYPE: PRT
<213> ORGANISM: Simian virus 40

<400> SEQUENCE: 57

Cys Gly Gly Pro Lys Lys Lys Arg Lys Val Gly
1               5                   10

<210> SEQ ID NO 58
<211> LENGTH: 7
<212> TYPE: PRT
<213> ORGANISM: Simian virus 40

<400> SEQUENCE: 58

Pro Lys Lys Lys Ile Lys Val
1               5

<210> SEQ ID NO 59
<211> LENGTH: 34
<212> TYPE: PRT
<213> ORGANISM: Simian virus 40

<400> SEQUENCE: 59

Cys Tyr Asp Asp Glu Ala Thr Ala Asp Ser Gln His Ser Thr Pro Pro
1               5                   10                  15

Lys Lys Lys Arg Lys Val Glu Asp Pro Lys Asp Phe Glu Ser Glu Leu
```

```
                        20                  25                  30

Leu Ser

<210> SEQ ID NO 60
<211> LENGTH: 13
<212> TYPE: PRT
<213> ORGANISM: Simian virus 40

<400> SEQUENCE: 60

Cys Gly Tyr Gly Pro Lys Lys Lys Arg Lys Val Gly Gly
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Polyoma large T protein

<400> SEQUENCE: 61

Pro Lys Lys Ala Arg Glu Asp
1               5

<210> SEQ ID NO 62
<211> LENGTH: 13
<212> TYPE: PRT
<213> ORGANISM: Artificial Sequence
<220> FEATURE:
<223> OTHER INFORMATION: Polyoma large T protein

<400> SEQUENCE: 62

Cys Gly Tyr Gly Val Ser Arg Lys Arg Pro Arg Pro Gly
1               5                   10

<210> SEQ ID NO 63
<211> LENGTH: 8
<212> TYPE: PRT
<213> ORGANISM: Simian virus 40

<400> SEQUENCE: 63

Ala Pro Thr Lys Arg Lys Gly Ser
1               5

<210> SEQ ID NO 64
<211> LENGTH: 11
<212> TYPE: PRT
<213> ORGANISM: Artificial Sequence
<220> FEATURE:
<223> OTHER INFORMATION: Polyoma virus major capsid protein VP1

<400> SEQUENCE: 64

Ala Pro Lys Arg Lys Ser Gly Val Ser Lys Cys
1               5                   10

<210> SEQ ID NO 65
<211> LENGTH: 7
<212> TYPE: PRT
<213> ORGANISM: Simian virus 40

<400> SEQUENCE: 65

Pro Asn Lys Lys Lys Arg Lys
1               5

<210> SEQ ID NO 66
<211> LENGTH: 12
```

```
<212> TYPE: PRT
<213> ORGANISM: Artificial Sequence
<220> FEATURE:
<223> OTHER INFORMATION: Polyoma virus capsid protein VP2

<400> SEQUENCE: 66

Glu Glu Asp Gly Pro Gln Lys Lys Lys Arg Arg Leu
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Yeast histone H2B

<400> SEQUENCE: 67

Gly Lys Lys Arg Ser Lys Ala
1               5

<210> SEQ ID NO 68
<211> LENGTH: 5
<212> TYPE: PRT
<213> ORGANISM: Artificial Sequence
<220> FEATURE:
<223> OTHER INFORMATION: Adenovirus E1a

<400> SEQUENCE: 68

Lys Arg Pro Arg Pro
1               5

<210> SEQ ID NO 69
<211> LENGTH: 11
<212> TYPE: PRT
<213> ORGANISM: Artificial Sequence
<220> FEATURE:
<223> OTHER INFORMATION: Adenovirus type 2/5 E1a

<400> SEQUENCE: 69

Cys Gly Gly Leu Ser Ser Lys Arg Pro Arg Pro
1               5                   10

<210> SEQ ID NO 70
<211> LENGTH: 12
<212> TYPE: PRT
<213> ORGANISM: Xenopus laevis

<400> SEQUENCE: 70

Leu Lys Asp Lys Asp Ala Lys Lys Ser Lys Gln Glu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: v-Rel or p59v-rel

<400> SEQUENCE: 71

Gly Asn Lys Ala Lys Arg Gln Arg Ser Thr
1               5                   10

<210> SEQ ID NO 72
<211> LENGTH: 11
<212> TYPE: PRT
<213> ORGANISM: Influenza A virus
```

```
<400> SEQUENCE: 72

Pro Phe Leu Asp Arg Leu Arg Arg Asp Gln Lys
1               5                   10

<210> SEQ ID NO 73
<211> LENGTH: 9
<212> TYPE: PRT
<213> ORGANISM: Homo sapiens

<400> SEQUENCE: 73

Ser Val Thr Lys Lys Arg Lys Leu Glu
1               5

<210> SEQ ID NO 74
<211> LENGTH: 9
<212> TYPE: PRT
<213> ORGANISM: Xenopus laevis

<400> SEQUENCE: 74

Ser Ala Ser Lys Arg Arg Arg Leu Glu
1               5

<210> SEQ ID NO 75
<211> LENGTH: 11
<212> TYPE: PRT
<213> ORGANISM: Human adenovirus type 5

<400> SEQUENCE: 75

Pro Pro Lys Lys Arg Met Arg Arg Arg Ile Glu
1               5                   10

<210> SEQ ID NO 76
<211> LENGTH: 28
<212> TYPE: PRT
<213> ORGANISM: Rattus norvegicus

<400> SEQUENCE: 76

Tyr Arg Lys Cys Leu Gln Ala Gly Met Asn Leu Glu Ala Arg Lys Thr
1               5                   10                  15

Lys Lys Lys Ile Lys Gly Ile Gln Gln Ala Thr Ala
            20                  25

<210> SEQ ID NO 77
<211> LENGTH: 54
<212> TYPE: PRT
<213> ORGANISM: Homo sapiens

<400> SEQUENCE: 77

Arg Lys Asp Arg Arg Gly Gly Arg Met Leu Lys His Lys Arg Gln Arg
1               5                   10                  15

Asp Asp Gly Glu Gly Arg Gly Glu Val Gly Ser Ala Gly Asp Met Arg
            20                  25                  30

Ala Met Ile Asn Ala Cys Ile Asp Asn Leu Trp Pro Ser Pro Leu Met
            35                  40                  45

Ile Lys Arg Ser Lys Lys
        50

<210> SEQ ID NO 78
<211> LENGTH: 8
<212> TYPE: PRT
<213> ORGANISM: Artificial Sequence
<220> FEATURE:
<223> OTHER INFORMATION: Rabbit progesterone receptor
```

```
<400> SEQUENCE: 78

Arg Lys Phe Lys Lys Phe Asn Lys
1               5

<210> SEQ ID NO 79
<211> LENGTH: 8
<212> TYPE: PRT
<213> ORGANISM: Artificial Sequence
<220> FEATURE:
<223> OTHER INFORMATION: c-myb gene product

<400> SEQUENCE: 79

Pro Leu Leu Lys Lys Ile Lys Gln
1               5

<210> SEQ ID NO 80
<211> LENGTH: 8
<212> TYPE: PRT
<213> ORGANISM: Artificial Sequence
<220> FEATURE:
<223> OTHER INFORMATION: N-myc gene produc

<400> SEQUENCE: 80

Pro Pro Gln Lys Lys Ile Lys Ser
1               5

<210> SEQ ID NO 81
<211> LENGTH: 7
<212> TYPE: PRT
<213> ORGANISM: Homo sapiens

<400> SEQUENCE: 81

Pro Gln Pro Lys Lys Lys Pro
1               5

<210> SEQ ID NO 82
<211> LENGTH: 9
<212> TYPE: PRT
<213> ORGANISM: Artificial Sequence
<220> FEATURE:
<223> OTHER INFORMATION: c-erb-A gene product

<400> SEQUENCE: 82

Ser Lys Arg Val Ala Lys Arg Lys Leu
1               5

<210> SEQ ID NO 83
<211> LENGTH: 14
<212> TYPE: PRT
<213> ORGANISM: Artificial Sequence
<220> FEATURE:
<223> OTHER INFORMATION: Yeast ribosomal protein L29

<400> SEQUENCE: 83

Met Thr Gly Ser Lys Thr Arg Lys His Arg Gly Ser Gly Ala
1               5                   10

<210> SEQ ID NO 84
<211> LENGTH: 6
<212> TYPE: PRT
<213> ORGANISM: Artificial Sequence
<220> FEATURE:
<223> OTHER INFORMATION: Yeast ribosomal protein L29

<400> SEQUENCE: 84
```

Arg His Arg Lys His Pro
1               5

<210> SEQ ID NO 85
<211> LENGTH: 6
<212> TYPE: PRT
<213> ORGANISM: Artificial Sequence
<220> FEATURE:
<223> OTHER INFORMATION: Yeast ribosomal protein L29

<400> SEQUENCE: 85

Lys Arg Arg Lys His Pro
1               5

<210> SEQ ID NO 86
<211> LENGTH: 6
<212> TYPE: PRT
<213> ORGANISM: Artificial Sequence
<220> FEATURE:
<223> OTHER INFORMATION: Yeast ribosomal protein L29

<400> SEQUENCE: 86

Lys Tyr Arg Lys His Pro
1               5

<210> SEQ ID NO 87
<211> LENGTH: 6
<212> TYPE: PRT
<213> ORGANISM: Artificial Sequence
<220> FEATURE:
<223> OTHER INFORMATION: Yeast ribosomal protein L29

<400> SEQUENCE: 87

Lys His Arg Arg His Pro
1               5

<210> SEQ ID NO 88
<211> LENGTH: 6
<212> TYPE: PRT
<213> ORGANISM: Artificial Sequence
<220> FEATURE:
<223> OTHER INFORMATION: Yeast ribosomal protein L29

<400> SEQUENCE: 88

Lys His Lys Lys His Pro
1               5

<210> SEQ ID NO 89
<211> LENGTH: 6
<212> TYPE: PRT
<213> ORGANISM: Artificial Sequence
<220> FEATURE:
<223> OTHER INFORMATION: Yeast ribosomal protein L29

<400> SEQUENCE: 89

Arg His Leu Lys His Pro
1               5

<210> SEQ ID NO 90
<211> LENGTH: 33
<212> TYPE: PRT
<213> ORGANISM: Hepatitis B virus

<400> SEQUENCE: 90

Pro Glu Thr Thr Val Val Arg Arg Arg Gly Arg Ser Pro Arg Arg
1               5                   10                  15

```
Thr Pro Ser Pro Arg Arg Arg Ser Pro Arg Arg Arg Ser Gln
            20                  25                  30

Ser

<210> SEQ ID NO 91
<211> LENGTH: 9
<212> TYPE: PRT
<213> ORGANISM: Artificial Sequence
<220> FEATURE:
<223> OTHER INFORMATION: Viral jun

<400> SEQUENCE: 91

Ala Ser Lys Ser Arg Lys Arg Lys Leu
1               5

<210> SEQ ID NO 92
<211> LENGTH: 16
<212> TYPE: PRT
<213> ORGANISM: Human T-cell lymphotropic virus type 1

<400> SEQUENCE: 92

Gly Gly Leu Cys Ser Ala Arg Leu His Arg His Ala Leu Leu Ala Thr
1               5                   10                  15

<210> SEQ ID NO 93
<211> LENGTH: 18
<212> TYPE: PRT
<213> ORGANISM: Mus musculus

<400> SEQUENCE: 93

Asp Thr Arg Glu Lys Lys Lys Phe Leu Lys Arg Arg Leu Leu Arg Leu
1               5                   10                  15

Asp Glu

<210> SEQ ID NO 94
<211> LENGTH: 1476
<212> TYPE: DNA
<213> ORGANISM: Artificial Sequence
<220> FEATURE:
<223> OTHER INFORMATION: P28z CAR

<400> SEQUENCE: 94
atggcctcac cgttgacccg ctttctgtcg ctgaacctgc tgctgctggg tgagtcgatt      60
atcctgggga gtggagaagc tgaggtgcag ctgcagcagt caggacctga actggtgaag     120
cctgggactt cagtgaggat atcctgcaag acttctggat acacattcac tgaatatacc     180
atacactggg tgaagcagag ccatggaaag agccttgagt ggattggaaa catcaatcct     240
aacaatggtg gtaccaccta caatcagaag ttcgaggaca aggccacatt gactgtagac     300
aagtcctcca gtacagccta catggagctc cgcagcctaa catctgagga ttctgcagtc     360
tattattgtg cagctggttg gaactttgac tactggggcc aagggaccac ggtcaccgtc     420
tcctcaggtg gaggtggatc aggtggaggt ggatctggtg gaggtggatc tgacattgtg     480
atgacccagt ctcacaaatt catgtccaca tcagtaggag acagggtcag catcatctgt     540
aaggccagtc aagatgtggg tactgctgta gactggtatc aacagaaacc aggacaatct     600
cctaaactac tgatttattg ggcatccact cggcacactg gagtccctga tcgcttcaca     660
ggcagtggat ctgggacaga cttcactctc accattacta atgttcagtc tgaagacttg     720
gcagattatt tctgtcagca atataacagc tatccctca cgttcggtgc tgggaccatg     780
ctggacctga acgggcggc cgcatctact actaccaagc cagtgctgcg aactccctca    840
```

```
cctgtgcacc ctaccgggac atctcagccc cagagaccag aagattgtcg gccccgtggc    900
tcagtgaagg ggaccggatt ggacttcgcc tgtgatattt acatctgggc acccttggcc    960
ggaatctgcg tggcccttct gctgtccttg atcatcactc tcatctgcta caatagtaga   1020
aggaacagac tccttcaaag tgactacatg aacatgactc cccggaggcc tgggctcact   1080
cgaaagcctt accagcccta cgcccctgcc agagactttg cagcgtaccg ccccagagca   1140
aaattcagca ggagtgcaga gactgctgcc aacctgcagg accccaacca gctctacaat   1200
gagctcaatc tagggcgaag agaggaatat gacgtcttgg agaagaagcg ggctcgggat   1260
ccagagatgg gaggcaaaca gcagaggagg aggaaccccc aggaaggcgt atacaatgca   1320
ctgcagaaag acaagatggc agaagcctac agtgagatcg gcacaaaagg cgagaggcgg   1380
agaggcaagg ggcacgatgg cctttaccag ggtctcagca ctgccaccaa ggacacctat   1440
gatgccctgc atatgcagac cctggcccct cgctaa                             1476
```